(12) United States Patent
Makino et al.

(10) Patent No.: US 11,417,908 B2
(45) Date of Patent: Aug. 16, 2022

(54) SOLID ELECTROLYTE COMPOSITION, SOLID ELECTROLYTE-CONTAINING SHEET AND MANUFACTURING METHOD THEREFOR, ALL-SOLID STATE SECONDARY BATTERY AND MANUFACTURING METHOD THEREFOR, POLYMER AND NON-AQUEOUS SOLVENT DISPERSION THEREOF, AND DIOL COMPOUND

(71) Applicant: FUJIFILM Corporation, Tokyo (JP)

(72) Inventors: Masaomi Makino, Kanagawa (JP); Tomonori Mimura, Kanagawa (JP); Yo Kushida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 16/520,483

(22) Filed: Jul. 24, 2019

(65) Prior Publication Data

US 2019/0348709 A1  Nov. 14, 2019

Related U.S. Application Data

(63) Continuation of application No. PCT/JP2018/001660, filed on Jan. 19, 2018.

(30) Foreign Application Priority Data

Feb. 13, 2017  (JP) .............................. JP2017-024481

(51) Int. Cl.
*H01M 10/0562* (2010.01)
*H01M 4/62* (2006.01)
*H01M 4/13* (2010.01)

(52) U.S. Cl.
CPC ......... *H01M 10/0562* (2013.01); *H01M 4/13* (2013.01); *H01M 4/622* (2013.01);
(Continued)

(58) Field of Classification Search
CPC .... H01M 10/0562; H01M 4/13; H01M 4/622; H01M 2300/0068; H01M 2300/0091
See application file for complete search history.

(56) References Cited

U.S. PATENT DOCUMENTS

| | | |
|---|---|---|
| 5,863,980 A | 1/1999 | Choi et al. |
| 2002/0042001 A1 | 4/2002 | Lee |

(Continued)

FOREIGN PATENT DOCUMENTS

| | | |
|---|---|---|
| CN | 1345897 A | 4/2002 |
| CN | 1664698 A | 9/2005 |

(Continued)

OTHER PUBLICATIONS

JP2009084443 MT (Year: 2009).*
JP2009053632 MT (Year: 2009).*

(Continued)

*Primary Examiner* — Alexander Usyatinsky
(74) *Attorney, Agent, or Firm* — Sughrue Mion, PLLC

(57) ABSTRACT

Provided are a solid electrolyte composition containing an inorganic solid electrolyte having a conductivity of an ion of a metal belonging to Group I or II of the periodic table and a binder having a specific constituent component, a solid electrolyte-containing sheet in which the same solid electrolyte composition is used and a manufacturing method therefor, an all-solid state secondary battery and a manufacturing method therefor, a polymer having a specific constituent component, a non-aqueous solvent dispersion thereof, and a diol compound.

14 Claims, 1 Drawing Sheet

(52) U.S. Cl.
CPC .............. *H01M 2300/0068* (2013.01); *H01M 2300/0091* (2013.01)

(56) References Cited

U.S. PATENT DOCUMENTS

| | | | |
|---|---|---|---|
| 2005/0196698 A1* | 9/2005 | Sugasaki | B41C 1/1008 430/270.1 |
| 2011/0117431 A1* | 5/2011 | Fukui | H01M 4/621 29/623.5 |
| 2012/0225351 A1* | 9/2012 | Kojima | H01M 4/13 429/211 |
| 2013/0260241 A1 | 10/2013 | Sone et al. | |
| 2016/0028108 A1 | 1/2016 | Hashimoto et al. | |
| 2016/0204465 A1* | 7/2016 | Mimura | C08F 220/14 429/162 |
| 2016/0204468 A1* | 7/2016 | Makino | C08G 18/282 429/310 |
| 2016/0336613 A1 | 11/2016 | Mochizuki et al. | |
| 2016/0359195 A1 | 12/2016 | Makino et al. | |
| 2017/0346075 A1 | 11/2017 | Mimura et al. | |

FOREIGN PATENT DOCUMENTS

| | | | |
|---|---|---|---|
| CN | 101997138 A | | 3/2011 |
| CN | 102187500 A | | 9/2011 |
| CN | 105580186 A | | 5/2016 |
| CN | 105602497 A | | 5/2016 |
| CN | 105940457 A | | 9/2016 |
| JP | 2008-56894 A | | 3/2008 |
| JP | 2009-53632 A | | 3/2009 |
| JP | 2009-84443 A | | 4/2009 |
| JP | 2009084443 | * | 4/2009 |
| JP | 2015-88480 A | | 5/2015 |
| JP | 201588480 | * | 5/2015 |
| JP | 2015-167126 A | | 9/2015 |
| JP | 2016-25025 A | | 2/2016 |

| | | | |
|---|---|---|---|
| KR | 10-2016-0051877 A | | 5/2016 |
| WO | 2012/073678 A1 | | 6/2012 |
| WO | WO 2015/046314 | * | 4/2015 |
| WO | 2016/132872 A1 | | 8/2016 |

OTHER PUBLICATIONS

Zhang et al. Chem. Eng. Technol.2011,34, No. 1, 119-126. (Year: 2011).*
The Decision to grant a Patent issued by JPO for Application No. 2018-567343 (Year: 2021).*
The Decision to grant a Patent issued by KIPO for Application No. 10-2019-7019201 (Year: 2021).*
Communication dated Sep. 2, 2020, issued by the Korean Intellectual Property Office in Korean Machine Application No. 10-2019-7019201.
International Preliminary Report dated Aug. 13, 2019, issued by the International Bureau in corresponding application No. PCT/JP2018/001660.
Written Opinion dated Feb. 27, 2018, issued by the International Searching Authority in corresponding application No. PCT/JP2018/001660.
International Search Report dated Feb. 27, 2018, issued by the International Searching Authority in corresponding application No. PCT/JP2018/001660.
Office Action dated Jun. 16, 2020 in Japanese Application No. 2018-567343.
Extended European Search Report dated Oct. 17, 2019 issued by the European Patent Office in counterpart application No. 18751228.0.
First Office Action dated Nov. 22, 2021 from the China National Intellectual Property Administration in CN Application No. 201880010010.X.
Communication dated May 9, 2022 from the European Patent Office in European Application No. 18 751 228.0.
Office Action dated May 10, 2022 issued by the China National Intellectual Property Administration in corresponding Chinese Application No. 201880010010.X.

* cited by examiner

SOLID ELECTROLYTE COMPOSITION, SOLID ELECTROLYTE-CONTAINING SHEET AND MANUFACTURING METHOD THEREFOR, ALL-SOLID STATE SECONDARY BATTERY AND MANUFACTURING METHOD THEREFOR, POLYMER AND NON-AQUEOUS SOLVENT DISPERSION THEREOF, AND DIOL COMPOUND

CROSS-REFERENCE TO RELATED APPLICATIONS

This application is a Continuation of PCT International Application No. PCT/JP2018/001660 filed on Jan. 19, 2018, which claims priority under 35 U.S.C. § 119 (a) to Japanese Patent Application No. JP2017-024481 filed in Japan on Feb. 13, 2017. Each of the above applications is hereby expressly incorporated by reference, in its entirety, into the present application.

BACKGROUND OF THE INVENTION

1. Field of the Invention

The present invention relates to a solid electrolyte composition, a solid electrolyte-containing sheet and a manufacturing method therefor, an all-solid state secondary battery and a manufacturing method therefor, a polymer and a non-aqueous solvent dispersion thereof, and a diol compound.

2. Description of the Background Art

All-solid state secondary batteries such as an all-solid state lithium ion secondary battery are storage batteries which have a negative electrode, a positive electrode, and an inorganic solid electrolyte (SE) sandwiched between the negative electrode and the positive electrode and enable charging and discharging by the reciprocal migration of ions (for example, lithium ions) between both electrodes. In the all-solid state secondary batteries, an inorganic solid electrolyte is used, and thus an organic electrolytic solution becomes unnecessary. As a result, an all-solid state secondary battery can be manufactured by sequentially laminating an electrode layer that forms the negative electrode or the positive electrode and a solid electrolyte layer that forms the inorganic solid electrolyte. In addition, according to this method, it is possible to shape the respective layers provided with an increased area. Therefore, it is possible to realize an increase in the output or capacity of the all-solid state secondary battery.

Regarding all-solid state secondary batteries having the above-described superiority, furthermore, studies are being made to achieve improvement in electrode sheets that serve as the electrode layer or solid electrolyte-containing sheets that serve as the solid electrolyte layer.

For example, a method in which the adhesiveness (bonding property) between a binder and an inorganic solid electrolyte or the like is improved by using a solid electrolyte composition containing an inorganic solid electrolyte or the like and a binder has been proposed. As the above-described binder, JP2016-025025A describes fluorine-containing rubber (VDF-HFP). WO2012/073678A describes a binder composition containing a polymer having a specific structural unit and a specific functional group and a liquid-form medium. In addition, JP2015-088480A describes a polymer having a hard segment and a soft segment.

SUMMARY OF THE INVENTION

The present inventors carried out studies from the viewpoint of the industrial manufacturing of the above-described all-solid state secondary battery in which a solid electrolyte layer is used. As a result, it was found that, in order to improve the yield by enhancing the production aptitude of the all-solid state secondary battery using the above-described method, not only the above-described adhesiveness but also the strong toughness of the solid electrolyte layer are important.

Generally, each sheet is temporarily stored after manufactured. Therefore, there is a demand for a characteristic (scratch resistance) that does not allow the easy generation of defects such as scratches or cracks on the surface of the electrode layer or the solid electrolyte layer even in a case in which the electrode layer or the solid electrolyte layer comes into contact with the rear surface of the sheet. In addition, there is another demand for a characteristic (bend resistance) that does not allow the easy drop of an active material or the inorganic solid electrolyte from the electrode layer or the solid electrolyte layer since there is a case in which the sheet is wound around a winding core at, for example, a high curvature in a manufacturing step or after manufacturing. Particularly, in the case of producing the sheet using a roll-to-roll method in consideration of the productivity, the above-described characteristics become important.

However, in the above-described technique in which a binder is used, in the case of increasing the amount of the binder used for the purpose of improving the above-described characteristics, due to the increase in the amount used, the binder coats the active material or the inorganic solid electrolyte, and the ion conductivity is decreased. As such, in the case of using the binder, regarding the amount used, the above-described characteristics and the ion conductivity are in a trade-off relationship. Even in the case of using the fluorine-containing rubber or the binder composition described in JP2016-025025A or WO2012/073678A, a sufficient improvement effect is not obtained. In addition, the polymer described in JP2015-088480A exhibits a certain degree of an improvement effect, which is not satisfactory.

An object of the present invention is to provide a solid electrolyte composition capable of imparting bend resistance, scratch resistance, and an ion conductivity to a solid electrolyte-containing sheet on a high level by being used for the production of the solid electrolyte-containing sheet that constitutes an all-solid state secondary battery. Another object of the present invention is to provide a polymer and a non-aqueous solvent dispersion which are preferably used in the solid electrolyte composition and a diol compound that is preferable for the synthesis of the polymer.

In addition, still another object of the present invention is to provide a solid electrolyte-containing sheet and an all-solid state secondary battery in which the solid electrolyte composition is used, and manufacturing methods therefor.

As a result of intensive studies, the present inventors found that, in a case in which an active material or an inorganic solid electrolyte and a polymer having a constituent component described below as a binder are combined together, not only does it become possible to improve the productivity in the above-described industrial manufacturing, but also it is possible to impart excellent bend resistance and excellent scratch resistance to a solid electrolyte-containing sheet to be obtained while maintaining a high ion conductivity. In addition, it was found that the use of this solid electrolyte-containing sheet enables the realization of an all-solid state secondary battery which has a high ion conductivity and, furthermore, is capable of suppressing the occurrence of short-circuit. The present invention was completed by further repeating studies on the basis of the above-described finding.

That is, the above-described objects are achieved by the following means.

<1> A solid electrolyte composition comprising: an inorganic solid electrolyte (A) having a conductivity of an ion of a metal belonging to Group I or II of the periodic table; and a binder (B), in which the binder (B) has at least one selected from a constituent component represented by Formula (1) and a constituent component represented by Formula (2).

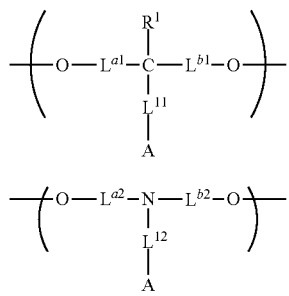

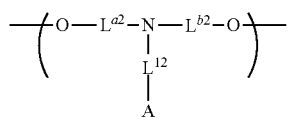

In Formula (1), $R^1$ represents a hydrogen atom, an alkyl group, or an aryl group. $L^{a1}$ and $L^{b1}$ each independently represent a single bond or an alkylene group. $L^{11}$ represents a divalent organic group. A represents a group selected from a group of functional groups below.

In Formula (2), $L^{a2}$ and $L^{b2}$ each independently represent an alkylene group having two or more carbon atoms. $L^{12}$ represents a divalent organic group. A represents a group selected from a group of functional groups below.

<Group of Functional Groups>

A carboxylic acid group, a sulfonic acid group, a phosphoric acid group, a cyano group, and a hydrocarbon ring group in which three or more rings are fused.

<2> The solid electrolyte composition according to <1>, in which one of $L^{a1}$ and $L^{b1}$ is a single bond, a methylene group, or an ethylene group, and the other of $L^{a1}$ and $L^{b1}$ is a methylene group or an ethylene group.

<3> The solid electrolyte composition according to <1>, in which $L^{a2}$ and $L^{b2}$ are all ethylene groups.

<4> The solid electrolyte composition according to any one of <1> to <3>, in which a partial structure $-L^{11}$-A in Formula (1) or a partial structure $-L^{12}$-A in Formula (2) is represented by any of Formulae (3) to (7).

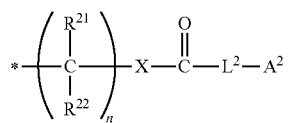

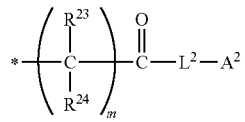

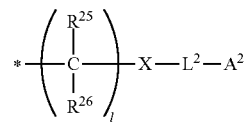

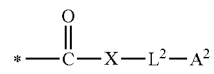

In Formulae (3) to (7), $R^{21}$ to $R^{26}$ each independently represent a hydrogen atom, an alkyl group, or an aryl group. $L^2$ represents an alkylene group having 1 to 18 carbon atoms, an alkenylene group having 2 to 20 carbon atoms or an arylene group having 6 to 16 carbon atoms, or a combination thereof. $A^2$ represents a carboxylic acid group. n, m, and l each independently represent an integer of 0 to 2. X represents —O—, —S—, or —N($R^2$)—, and $R^2$ represents a hydrogen atom, an alkyl group, or an aryl group. * represents a bonding portion with a C atom in Formula (1) or an N atom in Formula (2).

<5> The solid electrolyte composition according to any one of <1> to <4>, in which the binder (B) has a hard segment having at least one bond selected from a urethane bond, a urea bond, an amide bond, and an imide bond and a soft segment which has a number-average molecular weight of 300 or more and has at least one chain selected from a polyalkylene ether chain, a polyester chain, a polycarbonate chain, and a silicone chain.

<6> The solid electrolyte composition according to any one of <1> to <5>, in which the binder (B) has a hydrocarbon polymer segment.

<7> The solid electrolyte composition according to any one of <1> to <6>, in which the binder (B) is a particulate polymer having an average particle diameter of 10 to 1,000 nm.

<8> The solid electrolyte composition according to any one of <1> to <7>, further comprising: a dispersion medium (C).

<9> The solid electrolyte composition according to any one of <1> to <8>, further comprising: an active material (D).

<10> The solid electrolyte composition according to any one of <1> to <9>, further comprising: a conductive auxiliary agent (E).

<11> The solid electrolyte composition according to any one of <1> to <10>, in which the inorganic solid electrolyte (A) is a sulfide-based inorganic solid electrolyte.

<12> A solid electrolyte-containing sheet comprising: an inorganic solid electrolyte (A) having a conductivity of an ion of a metal belonging to Group I or II of the periodic table; and a binder (B), in which the binder (B) has at least one selected from a constituent component represented by Formula (1) and a constituent component represented by Formula (2).

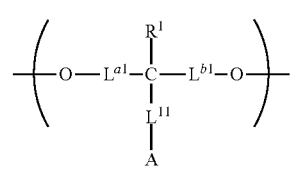

-continued

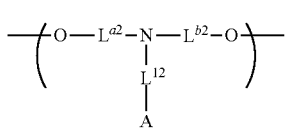
(2)

In Formula (1), $R^1$ represents a hydrogen atom, an alkyl group, or an aryl group. $L^{a1}$ and $L^{b1}$ each independently represent a single bond or an alkylene group. $L^{11}$ represents a divalent organic group. A represents a group selected from a group of functional groups below.

In Formula (2), $L^{a2}$ and $L^{b2}$ each independently represent an alkylene group having two or more carbon atoms. $L^{12}$ represents a divalent organic group. A represents a group selected from a group of functional groups below.

<Group of Functional Groups>

A carboxylic acid group, a sulfonic acid group, a phosphoric acid group, a cyano group, and a hydrocarbon ring group in which three or more rings are fused.

<13> A method for manufacturing the solid electrolyte-containing sheet according to <12>, the method comprising: a step of applying a solid electrolyte composition containing the inorganic solid electrolyte (A), the binder (B), and a dispersion medium (C) onto a base material; and a step of drying the applied solid electrolyte composition.

<14> An all-solid state secondary battery comprising: a positive electrode active material layer; a negative electrode active material layer; and a solid electrolyte layer, in which at least one of the positive electrode active material layer, the negative electrode active material layer, and the solid electrolyte layer contains an inorganic solid electrolyte (A) having a conductivity of an ion of a metal belonging to Group I or II of the periodic table; and a binder (B), and the binder (B) has at least one selected from a constituent component represented by Formula (1) and a constituent component represented by Formula (2).

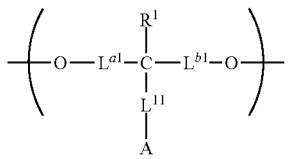
(1)

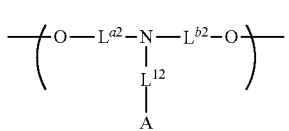
(2)

In Formula (1), $R^1$ represents a hydrogen atom, an alkyl group, or an aryl group. $L^{a1}$ and $L_{b1}$ each independently represent a single bond or an alkylene group. $L^{11}$ represents a divalent organic group. A represents a group selected from a group of functional groups below.

In Formula (2), $L^{a2}$ and $L^{b2}$ each independently represent an alkylene group having two or more carbon atoms. $L^{12}$ represents a divalent organic group. A represents a group selected from a group of functional groups below.

<Group of Functional Groups>

A carboxylic acid group, a sulfonic acid group, a phosphoric acid group, a cyano group, and a hydrocarbon ring group in which three or more rings are fused.

<15> A method for manufacturing an all-solid state secondary battery, in which an all-solid state secondary battery is manufactured using the method for manufacturing a solid electrolyte-containing sheet according to <13>.

<16> A polymer having at least one bond selected from a urethane bond, a urea bond, an amide bond, an imide bond, and an ester bond and having at least one constituent component selected from a constituent component represented by Formula (1) and a constituent component represented by Formula (2).

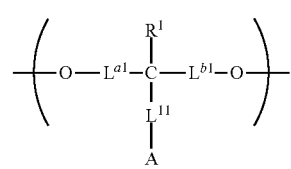
(1)

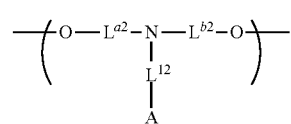
(2)

In Formula (1), $R^1$ represents a hydrogen atom, an alkyl group, or an aryl group. $L^{a1}$ and $L^{b1}$ each independently represent a single bond or an alkylene group. $-L^{11}$-A represents a partial structure represented by any of Formulae (3) to (7).

In Formula (2), $L^{a1}$ and $L^{b2}$ each independently represent an alkylene group having two or more carbon atoms. $-L^{12}$-A represents a partial structure represented by any of Formulae (3) to (7).

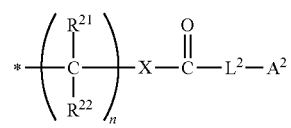
(3)

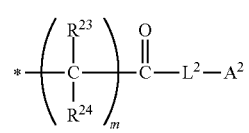
(4)

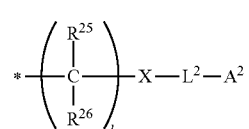
(5)

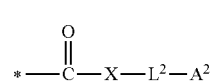
(6)

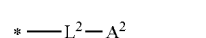
(7)

In Formulae (3) to (7), $R^{21}$ to $R^{26}$ each independently represent a hydrogen atom, an alkyl group, or an aryl group. $L^2$ represents an alkylene group having 1 to 18 carbon atoms, an alkenylene group having 2 to 20 carbon atoms or an arylene group having 6 to 16 carbon atoms, or a combination thereof. $A^2$ represents a carboxylic acid group. n, m, and l each independently represent an integer of 0 to 2. X represents —O—, —S—, or —N($R^2$)—, and $R^2$ represents a hydrogen atom, an alkyl group, or an aryl group. * represents a bonding portion with a C atom in Formula (1) or an N atom in Formula (2).

<17> A non-aqueous solvent dispersion of the polymer according to <16>.

<18> A diol compound for the polymer according to <16> which is represented by Formula (1M).

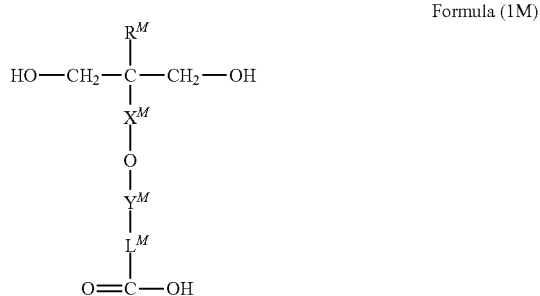

Formula (1M)

In Formula (1M), $R^M$ represents a methyl group or an ethyl group.

$X^M$ represents a methylene group or a carbonyl group, and $Y^M$ represents a single bond or a carbonyl group. Here, there is no case in which both $X^M$ and $Y^M$ are carbonyl groups.

$L^M$ is an alkylene group having 1 to 18 carbon atoms or an arylene group having 6 to 16 carbon atoms.

The present invention is capable of providing a solid electrolyte composition capable of imparting bend resistance, scratch resistance, and an ion conductivity to a solid electrolyte-containing sheet on a high level. The present invention is capable of providing a polymer and a non-aqueous solvent dispersion which are preferably used in the solid electrolyte composition and a diol compound that is preferable for the synthesis of the polymer.

In addition, the present invention is capable of providing a solid electrolyte-containing sheet and an all-solid state secondary battery in which the solid electrolyte composition is used, and manufacturing methods therefor.

The above-described and other characteristics and advantages of the present invention will be further clarified by the following description with appropriate reference to the accompanying drawings.

DESCRIPTION OF THE PREFERRED EMBODIMENTS

Figure 1:
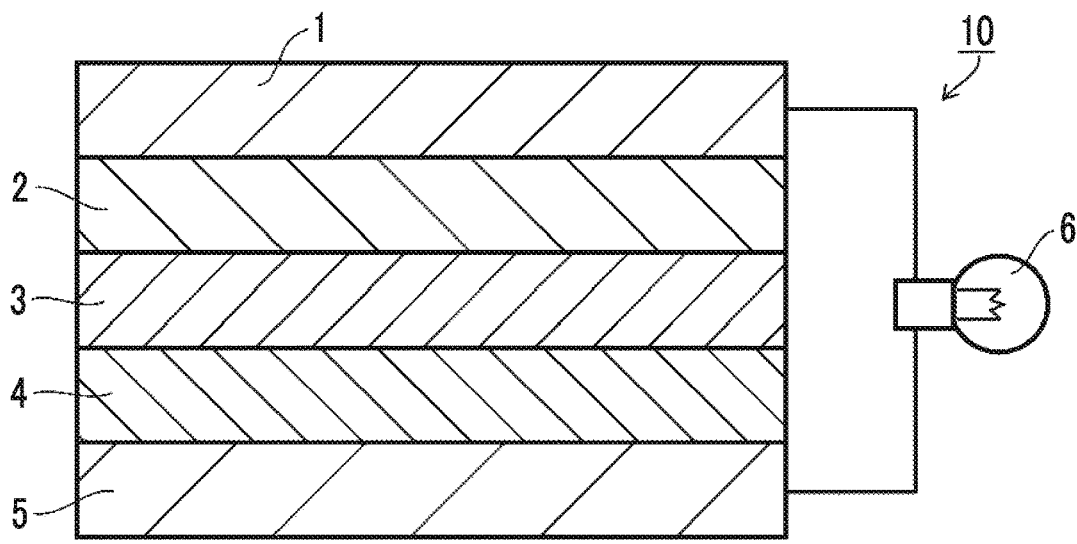
FIG. 1 is a vertical cross-sectional view schematically illustrating an all-solid state secondary battery according to a preferred embodiment of the present invention.

In the present specification, numerical ranges expressed using "to" include numerical values before and after the "to" as the lower limit value and the upper limit value.

In the present specification, "acrylic" or "(meth)acrylic" that is simply expressed is used to refer to acrylic and/or methacrylic. In addition, "acryloyl" or "(meth)acryloyl" that is simply expressed is used to refer to acryloyl and/or methacryloyl.

In the present specification, an expression of a compound (for example, in the case of referring to a substance with an expression "compound" at the end) is used to indicate the compound itself, a salt thereof, and an ion thereof.

In the present specification, a mass-average molecular weight (Mw) and a number-average molecular weight (Mn) can be measured as a polystyrene-equivalent molecular weight by means of gel permeation chromatography (GPC) unless particularly otherwise described. At this time, a GPC apparatus "HLC-8220" (trade name, manufactured by Tosoh Corporation) is used, G3000HXL+G2000HXL (all trade names, manufactured by Tosoh Corporation) is used as columns, and the molecular weight is detected using a differential refractometer (RI detector) at a measurement temperature of 23° C. and a flow rate of 1 mL/min. An eluent can be selected from tetrahydrofuran (THF), chloroform, N-methyl-2-pyrrolidone (NMP), and a m-cresol/chloroform liquid mixture (manufactured by Shonanwako Junyaku KK). In a case in which a measurement specimen is soluble, THF is used.

[Solid Electrolyte Composition]

A solid electrolyte composition of an embodiment of the present invention contains an inorganic solid electrolyte (A) having a conductivity of an ion of a metal belonging to Group I or II of the periodic table and a binder (B).

As described below, in the solid electrolyte composition, the inorganic solid electrolyte (A) and the binder (B) may be liberated (dispersed) from each other; however, generally, a functional group or the like in the binder (B) and the inorganic solid electrolyte (A) interact with each other, and the binder (B) and the inorganic solid electrolyte (A) adhere to each other. Particularly, in a solid electrolyte layer or the like that forms a solid electrolyte-containing sheet of an embodiment of the present invention and an all-solid state secondary battery of an embodiment of the present invention described below, the inorganic solid electrolyte (A) and the binder (B) adhere to each other. In an electrode sheet for an all-solid state secondary battery and an active substance layer, the binder (B) preferably also adheres to an active material, a conductive auxiliary agent, or the like in addition to the inorganic solid electrolyte (A).

In a case in which the binder (B) adheres to the inorganic solid electrolyte (A) or the like, the functional group in the binder (B) may remain (chemically or physically) unchanged depending on the type of the interaction with the inorganic solid electrolyte (A) or the like or may change. As a chemically or physically changed functional group, for example, an anion from which an active hydrogen is separated, a salt obtained by the exchange between active hydrogen and a cation, and the like are exemplified. The interaction or the like for the adhesion between the inorganic solid electrolyte (A) or the like and the binder (B) will be described below.

In the solid electrolyte composition of the embodiment of the present invention, it is considered that, as described above, the inorganic solid electrolyte (A) or the like and the binder (B) adhere to each other (are integrated together) due to the interaction, and a predetermined action effect described below is exhibited.

Hereinafter, a preferred embodiment will be described.

<(A) Inorganic Solid Electrolyte>

The inorganic solid electrolyte is an inorganic solid electrolyte, and the solid electrolyte refers to a solid-form electrolyte capable of migrating ions therein. The inorganic solid electrolyte is clearly differentiated from organic solid electrolytes (high-molecular-weight electrolytes represented by polyethylene oxide (PEO) or the like and organic electrolyte salts represented by lithium bis(trifluoromethanesulfonyl)imide (LiTFSI)) since the inorganic solid electrolyte does not include any organic substances as a principal ion-conductive material. In addition, the inorganic solid electrolyte is a solid in a static state and is thus, generally, not disassociated or liberated into cations and anions. Due to this fact, the inorganic solid electrolyte is also clearly differentiated from inorganic electrolyte salts of which cations and anions are disassociated or liberated in electrolytic solutions or polymers ($LiPF_6$, $LiBF_4$, LiFSI, LiCl, and the like). The inorganic solid electrolyte is not particularly limited as long as the inorganic solid electrolyte has conductivity of ions of metals belonging to Group I or II of the periodic table and is generally a substance not having electron conductivity.

In the present invention, the inorganic solid electrolyte has conductivity of ions of metals belonging to Group I or II of the periodic table. In a case in which the all-solid state secondary battery of the embodiment of the present invention is an all-solid state lithium ion secondary battery, the inorganic solid electrolyte preferably has an ion conductivity of a lithium ion.

As the inorganic solid electrolyte, it is possible to appropriately select and use solid electrolyte materials that are applied to this kind of products. Typical examples of the inorganic solid electrolyte include (i) sulfide-based inorganic solid electrolytes and (ii) oxide-based inorganic solid electrolytes. In the present invention, the sulfide-based inorganic solid electrolytes are preferably used since it is possible to form a more favorable interface between the active material and the inorganic solid electrolyte.

((i) Sulfide-Based Inorganic Solid Electrolytes)

Sulfide-based inorganic solid electrolytes are preferably inorganic solid electrolytes which contain sulfur atoms (S), have ion conductivity of metals belonging to Group I or II of the periodic table, and have electron-insulating properties. The sulfide-based inorganic solid electrolytes are preferably inorganic solid electrolytes which, as elements, contain at least Li, S, and P and have a lithium ion conductivity, but the sulfide-based inorganic solid electrolytes may also include elements other than Li, S, and P depending on the purposes or cases.

The ion conductivity of the sulfide-based inorganic solid electrolyte is preferably $1\times10^{-6}$ S/cm or more, more preferably $5\times10^{-6}$ S/cm or more, and particularly preferably $1\times10^{-5}$ S/cm or more. The upper limit is not particularly limited, but is realistically $1\times10^{-1}$ S/cm or less.

As the sulfide-based inorganic solid electrolyte, for example, lithium ion-conductive inorganic solid electrolytes satisfying a composition represented by Formula (I) are exemplified.

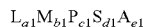

Formula (I)

In the formula, L represents an element selected from Li, Na, and K and is preferably Li. M represents an element selected from B, Zn, Sn, Si, Cu, Ga, Sb, Al, and Ge. A represents an element selected from I, Br, Cl, and F. a1 to e1 represent the compositional ratios among the respective elements, and a1:b1:c1:d1:e1 satisfies 1 to 12:0 to 5:1:2 to 12:0 to 10. a1 is preferably 1 to 9 and more preferably 1.5 to 7.5. b1 is preferably 0 to 3. d1 is preferably 2.5 to 10 and more preferably 3.0 to 8.5. Furthermore, e1 is preferably 0 to 5 and more preferably 0 to 3.

The compositional ratios among the respective elements can be controlled by adjusting the amounts of raw material compounds blended to manufacture the sulfide-based inorganic solid electrolyte as described below.

The sulfide-based inorganic solid electrolytes may be non-crystalline (glass) or crystallized (made into glass ceramic) or may be only partially crystallized. For example, it is possible to use Li—P—S-based glass containing Li, P, and S or Li—P—S-based glass ceramic containing Li, P, and S.

The sulfide-based inorganic solid electrolytes can be manufactured by a reaction of at least two raw materials of, for example, lithium sulfide ($Li_2S$), phosphorus sulfide (for example, diphosphorus pentasulfide ($P_2S_5$)), a phosphorus single body, a sulfur single body, sodium sulfide, hydrogen sulfide, lithium halides (for example, LiI, LiBr, and, LiCl), or sulfides of an element represented by M (for example, $SiS_2$, SnS, and $GeS_2$).

The ratio between $Li_2S$ and $P_7S_5$ in Li—P—S-based glass and Li—P—S-based glass ceramic is preferably 60:40 to 90:10 and more preferably 68:32 to 78:22 in terms of the molar ratio between $Li_2S:P_2S_5$. In a case in which the ratio between $Li_2S$ and $P_2S_5$ is set in the above-described range, it is possible to increase the lithium ion conductivity. Specifically, the lithium ion conductivity can be preferably set to $1\times10^{-4}$ S/cm or more and more preferably set to $1\times10^{-3}$ S/cm or more. The upper limit is not particularly limited, but realistically $1\times10^{-1}$ S/cm or less.

As specific examples of the sulfide-based inorganic solid electrolytes, combination examples of raw materials will be described below. Examples thereof include $Li_2S$—$P_2S_5$, $Li_2S$—$P_2S_5$—LiCl, $Li_2S$—$P_2S_5$—$H_2S$, $Li_2S$—$P_2S_5$—$H_2S$—LiCl, $Li_2S$—LiI—$P_2S_5$, $Li_2S$—LiI—$Li_2O$—$P_2S_5$, $Li_2S$—LiBr—$P_2S_5$, $Li_2S$—$Li_2O$—$P_2S_5$, $Li_2S$—$Li_3PO_4$—$P_2S_5$, $Li_2S$—$P_2S_5$—$P_2O_5$, $Li_2S$—$P_2S_5$—$SiS_2$, $Li_2S$—$P_2S_5$—$SiS_2$—LiCl, $Li_2S$—$P_2S_5$—SnS, $Li_2S$—$P_2S_5$—$Al_2S_3$, $Li_2S$—$GeS_2$, $Li_2S$—$GeS_2$—ZnS, $Li_2S$—$Ga_2S_3$, $Li_2S$—$GeS_2$—$Ga_2S_3$, $Li_2S$—$GeS_2$—$P_2S_5$, $Li_2S$—$GeS_2$—$Sb_2S_5$, $Li_2S$—$GeS_2$—$Al_2S_3$, $Li_2S$—$SiS_2$, $Li_2S$—$Al_2S_3$, $Li_2S$—$SiS_2$—$Al_2S_3$, $Li_2S$—$SiS_2$—$P_2S_5$, $Li_2S$—$SiS_2$—$P_2S_5$—LiI, $Li_2S$—$SiS_2$—LiI, $Li_2S$—$SiS_2$—$Li_4SiO_4$, $Li_2S$—$SiS_2$—$Li_3PO_4$, $Li_{10}GeP_2S_{12}$, and the like. Mixing ratios of the respective raw materials do not matter. Examples of a method for synthesizing sulfide-based inorganic solid electrolyte materials using the above-described raw material compositions include an amorphization method. Examples of the amorphization method include a mechanical milling method, a solution method, and a melting quenching method. This is because treatments at a normal temperature become possible, and it is possible to simplify manufacturing steps.

((ii) Oxide-Based Inorganic Solid Electrolytes)

Oxide-based inorganic solid electrolytes are preferably compounds which contain oxygen atoms (O), have an ion conductivity of metals belonging to Group I or II of the periodic table, and have electron-insulating properties.

The ion conductivity of the oxide-based inorganic solid electrolyte is preferably $1\times10^{-6}$ S/cm or more, more preferably $5\times10^{-6}$ S/cm or more, and particularly preferably $1\times10^{-5}$ S/cm or more. The upper limit is not particularly limited, but is realistically $1\times10^{-1}$ S/cm or less.

Specific examples of the compounds include $Li_{xa}La_{ya}TiO_3$ [xa=0.3 to 0.7 and ya=0.3 to 0.7] (LLT), $Li_{xb}La_{yb}Zr_{zb}M^{bb}_{mb}O_{nb}$ ($M^{bb}$ is at least one element of Al, Mg, Ca, Sr, V, Nb, Ta, Ti, Ge, In or Sn, xb satisfies 5≤xb≤10, yb satisfies 1≤yb≤4, zb satisfies 1≤zb≤4, mb satisfies 0≤mb≤2, and nb satisfies 5≤nb≤20), $Li_{xc}B_{yc}M^{cc}_{zc}O_{nc}$ ($M^{cc}$ is at least one element of C, S, Al, Si, Ga, Ge, In, or Sn, xc satisfies $0 \leq xc \leq 5$, yc satisfies $0 \leq yc \leq 1$, zc satisfies $0 \leq zc \leq 1$, and nc satisfies $0 \leq nc \leq 6$), $Li_{xd}(Al, Ga)_{yd}(Ti, Ge)_{zd}Si_{ad}P_{md}O_{nd}$ ($1 \leq xd \leq 3$, $0 \leq yd \leq 1$, $0 \leq zd \leq 2$, $0 \leq ad \leq 1$, $1 \leq md \leq 7$, $3 \leq nd \leq 13$), $Li_{(3-2xe)}M^{ee}_{xe}D^{ee}O$ (xe represents a number of 0 or more and 0.1 or less, and $M^{ee}$ represents a divalent metal atom. $D^{ee}$ represents a halogen atom or a combination of two or more halogen atoms), $Li_{xf}Si_{yf}O_{zf}$ ($1 \leq xf \leq 5$, $0 < yf \leq 3$, $1 \leq zf \leq 10$), $Li_{xg}S_{yg}O_{zg}$ ($1 \leq xg \leq 3$, $0 < yg \leq 2$, $1 \leq zg \leq 10$), $Li_3BO_3$—$Li_2SO_4$, $Li_2O$—$B_2O_3$—$P_2O_5$, $Li_2O$—$SiO_2$, $Li_6BaLa_2Ta_2O_{12}$, $Li_3PO_{(4-3/2w)}N_w$ (w satisfies w<1), $Li_{3.5}Zn_{0.25}GeO_4$ having a lithium super ionic conductor (LISICON)-type crystal structure, $La_{0.55}Li_{0.35}TiO_3$ having a perovskite-type crystal structure, $LiTi_2P_3O_{12}$ having a natrium super ionic conductor (NASICON)-type crystal structure, $Li_{1+xh+yh}(Al, Ga)_{xh}(Ti, Ge)_{2-xh}Si_{yh}P_{3-yh}O_{12}$ ($0 \leq xh \leq 1$, $0 \leq y \leq 1$), $Li_7La_3Zr_2O_{12}$ (LLZ) having a garnet-type crystal structure.

In addition, phosphorus compounds containing Li, P and O are also desirable. Examples thereof include lithium phosphate ($Li_3PO_4$), LiPON in which some of oxygen atoms in lithium phosphate are substituted with nitrogen, $LiPOD^1$ ($D^1$ is at least one element selected from Ti, V, Cr, Mn, Fe, Co, Ni, Cu, Zr, Nb, Mo, Ru, Ag, Ta, W, Pt, Au, or the like), and the like.

Furthermore, it is also possible to preferably use $LiA^1ON$ ($A^1$ represents at least one element selected from Si, B, Ge, Al, C, Ga, or the like) and the like.

The inorganic solid electrolyte is preferably particles. The volume-average particle diameter of the particulate inorganic solid electrolyte is not particularly limited, but is preferably 0.01 μm or more and more preferably 0.1 μm or more. The upper limit is preferably 100 μm or less and more preferably 50 μm or less. Meanwhile, the average particle diameter of the inorganic solid electrolyte particles is measured in the following order. One percent by mass of a dispersion liquid is diluted and prepared using the inorganic solid electrolyte particles and water (heptane in a case in which the inorganic solid electrolyte is unstable in water) in a 20 ml sample bottle. The diluted dispersion liquid specimen is irradiated with 1 kHz ultrasonic waves for 10 minutes and is then immediately used for testing. Data capturing is carried out 50 times using this dispersion liquid specimen, a laser diffraction/scattering-type particle size distribution measurement instrument LA-920 (manufactured by Horiba Ltd), and a silica cell for measurement at a temperature of 25° C., thereby obtaining the volume-average particle diameter. Regarding other detailed conditions and the like, the description of HS Z8828:2013 "Particle size analysis-Dynamic light scattering method" is referred to as necessary. Five specimens are produced and measured per level, and the average values thereof are employed.

The inorganic solid electrolyte may be used singly or two or more inorganic solid electrolytes may be used in combination.

In a case in which a decrease in the interface resistance and the maintenance of the decreased interface resistance in the case of being used in the all-solid state secondary battery are taken into account, the content of the inorganic solid electrolyte in the solid component of the solid electrolyte composition is preferably 5% by mass or more, more preferably 10% by mass or more, and particularly preferably 20% by mass or more with respect to 100% by mass of the solid components. From the same viewpoint, the upper limit is preferably 99.9% by mass or less, more preferably 99.5% by mass or less, and particularly preferably 99% by mass or less.

Here, in a case in which the solid electrolyte composition contains an active material described below, regarding the content of the inorganic solid electrolyte in the solid electrolyte composition, the total content of the active material and the inorganic solid electrolyte is preferably in the above-described range.

The solid component (solid content) in the present specification refers to a component that does not volatilize or evaporate and thus disappear in the case of being subjected to a drying treatment in a nitrogen atmosphere at 170° C. for six hours. Typically, the solid content refers to a component other than a dispersion medium described below.

<(B) Binder>

The solid electrolyte composition of the embodiment of the invention contains the binder (B).

The binder (B) that is used in the present invention is made of a polymer having at least one constituent component selected from a constituent component represented by Formula (1) and a constituent component represented by Formula (2). The constituent component that the binder has may be any of at least one type of constituent component represented by Formula (1), at least one type of constituent component represented by Formula (2), or a combination of at least one type of constituent component represented by Formula (1) and at least one type of constituent component represented by Formula (2). The number of types of each of the constituent components represented by the respective formulae that the binder has is preferably one to five.

The binder (B) needs to have the above-described constituent component in the molecular structure of the polymer and may have the constituent component in any of the main chain or a branched chain. From the viewpoint of the bonding property with an active material or the inorganic solid electrolyte (both are also collectively referred to as inorganic particles), the binder preferably contains the constituent component in the main chain of the polymer.

In the present specification, the "main chain" refers to a linear molecular chain for which all of the molecular chains other than the main chain in all of the molecular chains in the polymer can be regarded as pendants with respect to the main chain. Typically, the longest chain of molecular chains that constitute a polymer is the main chain. However, a functional group that a polymer terminal has is not regarded as the main chain.

In a case in which the binder (B) is a condensation polymerization polymer or a polyaddition polymer, the above-described constituent component is contained as one constituent component that forms a repeating unit.

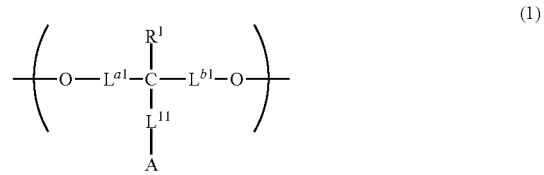

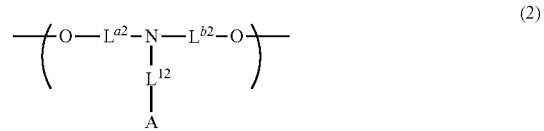

(Constituent Component Represented by Formula (1))

In Formula (1), $R^1$ represents a hydrogen atom, an alkyl group, or an aryl group.

The alkyl group that can be employed as $R^1$ may be any of a linear alkyl group, a branched alkyl group, or a cyclic alkyl group and is preferably a linear alkyl group or a branched alkyl group and more preferably a linear alkyl group. The number of carbon atoms in the alkyl group is not particularly limited, but is, for example, preferably 1 to 20, more preferably 1 to 12, and still more preferably 1 to 6.

The aryl group that can be employed as $R^1$ is not particularly limited and may be a monocyclic aryl group or an aryl group of a fused ring and may be an aryl group made of a hydrocarbon ring or an aryl group made of a hetero ring. An aryl group made of a monocyclic hydrocarbon ring, that is, a phenyl group is preferred. The number of carbon atoms in the aryl group is not particularly limited, but is preferably 6 to 18, more preferably 6 to 12, and still more preferably 6 to 10.

$R^1$ is preferably a hydrogen atom or an alkyl group and more preferably an alkyl group.

In Formula (1), $L^{a1}$ and $L^{b1}$ each independently represent a single bond or an alkylene group.

The alkylene group that can be employed as $L^{a1}$ and $L^{b1}$ may be any of a linear alkylene group, a branched alkylene group, or a cyclic alkylene group and is preferably a linear alkylene group or a branched alkylene group and more preferably a linear alkylene group.

The number of carbon atoms in the alkylene group is not particularly limited, but is, for example, preferably 1 to 18, more preferably 1 to 12, and still more preferably 1 to 6. The total number of carbon atoms of $L^{a1}$ and $L^{b1}$ is appropriately set depending on an aspect of $L^{a1}$ and $L^{b1}$ being combined into the binder (B) so as to preferably fall in the above-described range. For example, in the case of having the constituent component represented by Formula (1) as a hard segment, the total number of carbon atoms of $L^{a1}$ and $L^{b1}$ is set so as to be adequate for a hard segment described below. In this case, the total number of carbon atoms of $L^{a1}$ and $L^{b1}$ is preferably 1 to 6, more preferably 1 to 4, and still more preferably 1 or 2.

The alkylene group that can be employed as $L^{a1}$ and $L^{b1}$ is preferably a linear alkylene group not having any substituent. That is, the minimum number of carbon atoms that bond oxygen atoms in the respective formulae and carbon atoms to which $L^{11}$ bonds in the shortest distance is preferably identical to the above-described number of carbon atoms.

$L^{a1}$ and $L^{b1}$ each are selected from a single bond and the alkylene groups, and a combination thereof is not particularly limited. From the viewpoint of the easiness in synthesis, it is preferable that one of $L^{a1}$ and $L^{b1}$ is selected from a single bond and the alkylene group and the other of $L^{a1}$ and $L^{b1}$ is selected from the alkylene group. It is more preferable that one of $L^{a1}$ and $L^{b1}$ is selected from a single bond, methylene, and ethylene and the other of $L^{a1}$ and $L^{b1}$ is selected from methylene and ethylene.

$L^{a1}$ and $L^{b1}$ may be groups that are identical to or different from each other.

In Formula (1), $L^{11}$ represents a divalent organic group. The divalent organic group is not particularly limited, but is preferably an alkylene group (the number of carbon atoms is more preferably 1 to 18 and still more preferably 1 to 10), an alkenylene group (the number of carbon atoms is, preferably 2 to 20, more preferably 2 to 18, and still more preferably 2 to 10), an arylene group (the number of carbon atoms is more preferably 6 to 16 and still more preferably 6 to 14), a heteroarylene group (the number of carbon atoms is preferably 2 to 20), —O—, —S—, —N($R^2$)—, —C(=O)—, or a group formed of a combination thereof.

More preferred is the alkylene group, the alkenylene group, the arylene group, —O—, —S—, —N($R^2$)—, —C(=O)—, or a group formed of a combination thereof. Particularly preferred is a group from which "$A^2$" in partial structures represented by Formulae (3) to (7) illustrated below is removed.

Examples of the alkylene group that forms the divalent organic group include, in addition to a linear alkylene group and a branched alkylene group, a cyclic alkylene group (for example, a cycloalkylidene group (cyclopropylidene, cyclopentylidene, cyclohexylidene, or the like)), furthermore, a group obtained by combining a linear alkylene group or a branched alkylene group with a cyclic alkylene group. Here, the number of carbon atoms in the cyclic alkylene group is preferably 3 or more. In addition, the cyclic alkylene group may have an unsaturated bond in the ring.

Examples of the alkenylene group that forms the divalent organic group include not only groups that serve as a bonding portion of two carbon atoms that form a carbon-carbon unsaturated bond but also groups in which at least one of carbon atoms that form a carbon-carbon unsaturated bond serves as a bonding portion. Examples of such groups include alkylene groups to which a carboxy group bonds in exemplary compounds b-29 and b-30 described below.

The arylene group that forms the divalent organic group is not particularly limited, and groups obtained by removing one hydrogen atom from the aryl group that can be employed as $R^1$ are exemplified.

The heteroarylene group that forms the divalent organic group is not particularly limited, but is preferably a heteroarylene group of a five-membered ring or a six-membered ring having at least any one of an oxygen atom, a sulfur atom, or a nitrogen atom as a ring-constituting atom. The heteroarylene group may be fused, and the fused ring is preferably a benzene ring. A heteroarylene ring that forms the heteroarylene group includes an aromatic ring.

$R^2$ represents a hydrogen atom, an alkyl group (the number of carbon atoms is preferably 1 to 8), or an aryl group (the number of carbon atoms is preferably 6 to 12).

In Formula (1), A represents a group selected from a group of functional groups below.

The functional group selected from the following group of functional groups chemically or physically interacts with the surface of the inorganic solid electrolyte in the solid electrolyte composition and an active material or a conductive auxiliary agent that coexists as desired. This interaction is not particularly limited, and examples thereof include an interaction by a hydrogen bond, an interaction by an ionic bond of an acid-base group, an interaction by a covalent bond, an interaction by a π-π interaction of an aromatic ring, an interaction by a hydrophobic-hydrophobic interaction, and the like. In a case in which the functional group interacts, the chemical structure of the functional group may or may not change as described above. For example, in the π-π interaction or the like, generally, the functional group does not change and maintains the intrinsic structure. On the other hand, in the interaction by a covalent bond or the like, the functional group turns into an anion from which active hydrogen in a carboxylic acid group or the like is separated (the functional group changes) and bonds to a solid electrolyte. Due to this interaction, the functional group contributes to the adsorption of the binder (B) to the particles of the inorganic solid electrolyte or the like at the time of or during the preparation of the solid electrolyte composition. It is considered that these functional groups are separated from the main chain of the binder (B), that is, bond together through the linking group (spacer) $L_{11}$ or $L_{12}$, whereby the molecular mobility of a functional group A is enhanced, the contact frequency with particle interfaces improves, and an interaction to be formed also becomes strong. The functional group A also interacts with the surface of a collector.

<Group of Functional Groups>

A carboxylic acid group (—COOH), a sulfonic acid group (sulfo group: —SO$_3$H), phosphoric acid group (phosphor group: —OPO(OH))$_2$ or the like, a cyano group, and a hydrocarbon ring group in which three or more rings are fused.

The carboxylic acid group, the sulfonic acid group, and the phosphoric acid group each may be a salt thereof or may be an ester. As the salt, for example, a sodium salt, a calcium salt, and the like are exemplified. As the ester, an alkyl ester, an aryl ester, and the like are exemplified. In the case of the ester, the number of carbon atoms is preferably 1 to 24, more preferably 1 to 12, and particularly preferably 1 to 6.

The hydrocarbon ring group in which three or more rings are fused is not particularly limited as long as a hydrocarbon ring is a ring group in which three or more rings are fused. As the hydrocarbon ring that is fused, a saturated aliphatic hydrocarbon ring, an unsaturated aliphatic hydrocarbon ring, and an aromatic hydrocarbon ring (benzene ring) are exemplified. The hydrocarbon ring is preferably a five-membered ring or a six-membered ring.

The hydrocarbon ring group in which three or more rings are fused is preferably a ring group in which three or more rings are fused which includes at least one aromatic hydrocarbon ring or a ring group in which three or more saturated aliphatic hydrocarbon rings or unsaturated aliphatic hydrocarbon rings are fused.

The number of rings that are fused is not particularly limited, but is preferably 3 to 8 and more preferably 3 to 5.

The ring group in which three or more rings are fused which includes at least one aromatic hydrocarbon ring is not particularly limited, and examples thereof include ring groups made of anthracene, phenanthracene, pyrene, tetracene, tetraphene, chrysene, triphenylene, pentacene, pentaphene, perylene, benzo[a]pyrene, coronene, antanthrene, corannulene, ovalene, graphene, cycloparaphenylene, polyparaphenylene, or cyclophen.

The ring group in which three or more saturated aliphatic hydrocarbon rings or unsaturated aliphatic hydrocarbon rings are fused is not particularly limited, and, for example, ring groups made of a compound having a steroid skeleton are exemplified. As the compound having a steroid skeleton, for example, ring groups made of a compound of cholesterol, ergosterol, testosterone, estradiol, aldosterone, hydrocortisone, stigmasterol, thymosterol, lanosterol, 7-dehydrodesmosterol, 7-dehydrocholesterol, cholanic acid, cholic acid, lithocholic acid, deoxycholic acid, sodium deoxycholate, lithium deoxycholate, hydrodeoxycholic acid, chenodeoxycholic acid, ursodeoxycholic acid, dehydrocholic acid, hocochoic acid, or hyocholic acid are exemplified.

As the hydrocarbon ring group in which three or more rings are fused, among the above-described ring groups, the ring group made of a compound having a cholesterol ring structure or a vinylene group is more preferred.

The functional group is appropriately selected from the above-described functional groups, and, from the viewpoint of the bonding property with an active material, in a case in which the solid electrolyte composition contains a positive electrode active material, the carboxylic acid group, the sulfonic acid group, the phosphoric acid group, or the cyano group is preferred, and, in a case in which the solid electrolyte composition contains a negative electrode active material, the hydrocarbon ring group in which three or more rings are fused is preferred.

As the functional group, from the viewpoint of exhibiting a strong bonding property regardless of the active material, the carboxylic acid group, the sulfonic acid group, or the phosphoric acid group is preferred, and the carboxylic acid group is more preferred.

The functional group interacts with the inorganic particles and exhibits a function of adsorbing the particles and the binder (B).

(Constituent Component Represented by Formula (2))

In Formula (2), $L^{a2}$ and $L^{b2}$ each independently represent an alkylene group having two or more carbon atoms.

The alkylene group that can be employed as $L^{a2}$ and $L^{b2}$ is identical to the alkylene group that can be employed as $L_{a1}$ and $L^{b1}$ except for the fact that the number of carbon atoms is two or more, and a preferred range is also identical thereto. However, the total number of carbon atoms of $L^{a2}$ and $L^{b2}$ is preferably 4 to 12, more preferably 4 to 8, and still more preferably 4. The alkylene group that can be employed as $L^{a2}$ and $L^{b2}$ is preferably a linear alkylene group not having any substituent.

The combination of the alkylene groups that can be employed as $L^{a2}$ and $L^{b2}$ is not particularly limited, the alkylene groups may be groups that are identical to or different from each other. The groups combined together as the alkylene groups that can be employed as $L^{a2}$ and $L^{b2}$ are all preferably ethylene.

In Formula (2), $L^{12}$ represents a divalent organic group. The divalent organic group that can be employed as $L^{12}$ is identical to the divalent organic group that can be employed as $L^{11}$, and a preferred range is also identical thereto. Here, in the divalent organic group that can be employed as $L^{12}$, the number of atoms that bond the nitrogen atoms in Formula (2) and the functional group A in the shortest distance is preferably two or more. For example, in a case in which an alkylene group is employed as $L^{12}$, the number of carbon atoms in the alkylene group is preferably two or more.

In Formula (2), A represents a group selected from the group of functional groups and is identical to A in Formula (1), and a preferred range thereof is also identical thereto.

In the constituent component represented by Formula (1) and the constituent component represented by Formula (2), a partial structure -$L^{11}$-A in Formula (1) or a partial structure -$L^{12}$-A in Formula (2) is preferably the partial structure represented by any of Formulae (3) to (7).

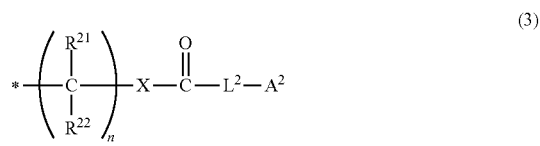

(3)

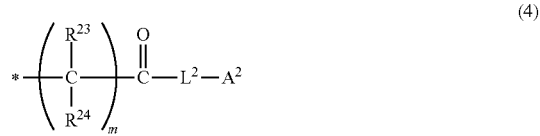

(4)

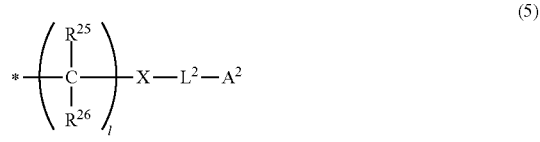

(5)

-continued

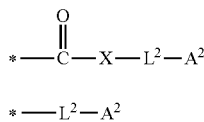
(6)

*—L²—A² (7)

In Formulae (3) to (7), $R^{21}$ to $R^{26}$ each independently represent a hydrogen atom, an alkyl group, or an aryl group. $R^{21}$ to $R^{26}$ are preferably hydrogen atoms or alkyl groups (particularly, alkyl groups having 1 to 4 carbon atoms) and more preferably hydrogen atoms.

In Formulae (3) to (7), $L^2$ represents an alkylene group having 1 to 18 carbon atoms, an alkenylene group having 2 to 20 carbon atoms or an arylene group having 6 to 16 carbon atoms, or a combination thereof. The alkylene group, the alkenylene group, and the arylene group that can be employed as $L^2$ each are identical to the alkylene group, the alkenylene group, and the arylene group that can be employed as $L^{11}$, and preferred ranges thereof are also identical thereto.

However, the alkylene group and the alkenylene group that can be employed as $L^2$ in Formula (3) to Formula (7) each are different from the alkylene group and the alkenylene group that can be employed as $L^{11}$ in the fact that the alkylene group and the alkenylene group may include a hetero atom or a group including a hetero atom in the carbon chain. The hetero atom and the hetero atom in the group including a hetero atom are not particularly limited, and an oxygen atom, a sulfur atom, or a nitrogen atom is exemplified. The group including a hetero atom is not particularly limited as long as the group has at least one hetero atom described above, and examples thereof include —N(R²)—, —C(=O)—, —C(=O)—O—, or —C(=O)N(R²)—. $R^2$ is as described above.

In Formulae (3) to (7), $A_2$ represents a carboxylic acid group.

In Formulae (3) to (5), n, m, and l each are integers of 0 to 2.

n is preferably one. m is preferably zero. l is preferably zero or one.

In Formulae (3) to (6), X represents —O—, —S—, or —N(R²)—.

X in Formula (3) is preferably —O—. X in Formula (5) is preferably —O— or —S— and more preferably —S—. X in Formula (6) is preferably —O—.

$R^2$ represents a hydrogen atom, an alkyl group, or an aryl group and is as described above.

In Formulae (3) to (7), * represents a bonding portion with a carbon atom to which bonds in Formula (1) or a nitrogen atom to which $L^{12}$ bonds in Formula (2).

Specific examples of the constituent component represented by Formula (1) and the constituent component represented by Formula (2) will be illustrated below as diol compounds (compounds in which hydrogen atoms bond to binding sites in the respective formulae) that are precursors thereof. In the present invention, the constituent component represented by Formula (1) and the constituent component represented by Formula (2) are not limited to constituent components derived from exemplary compounds illustrated below.

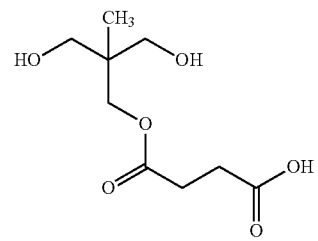
(b-1)

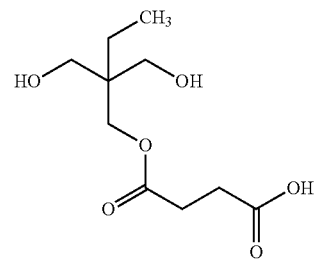
(b-2)

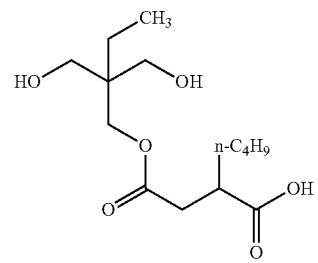
(b-3)

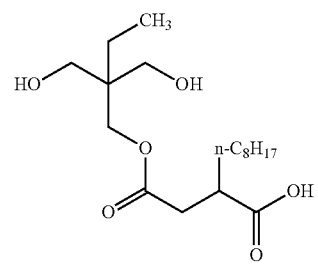
(b-4)

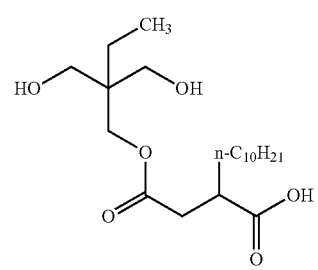
(b-5)

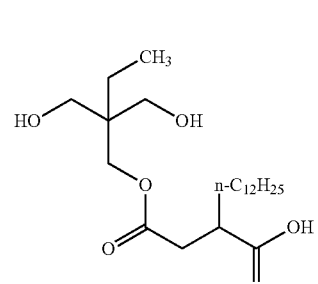
(b-6)

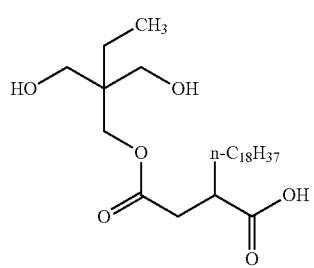
(b-7)
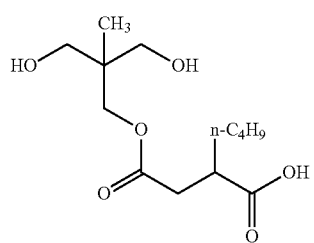
(b-8)
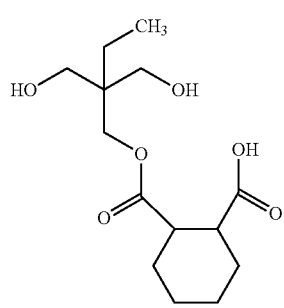
(b-9)
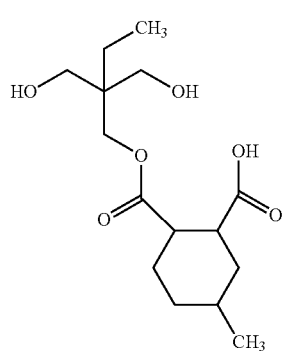
(b-10)
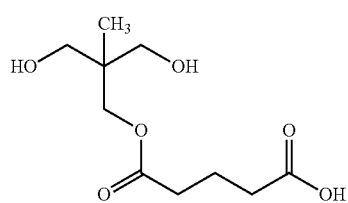
(b-11)
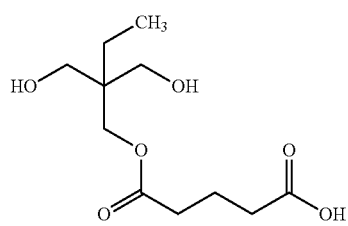
(b-12)
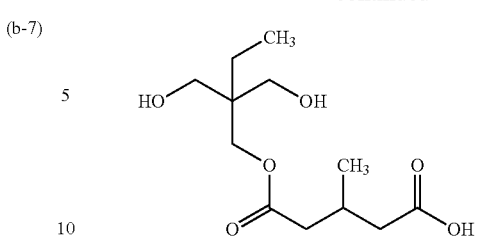
(b-13)
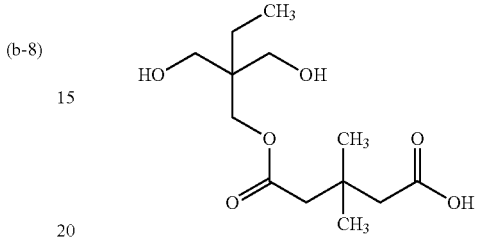
(b-14)
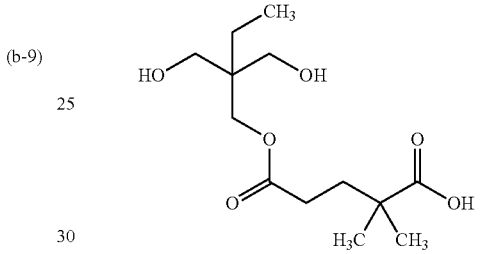
(b-15)
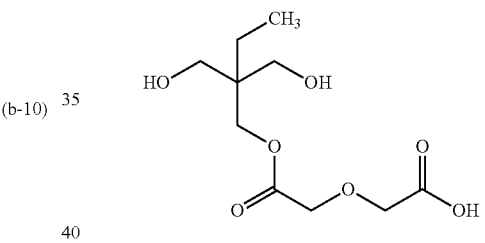
(b-16)
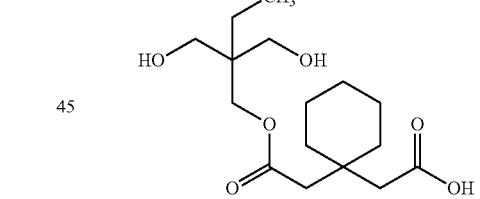
(b-17)
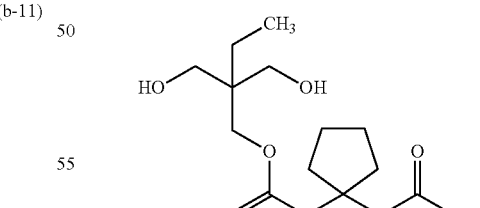
(b-18)
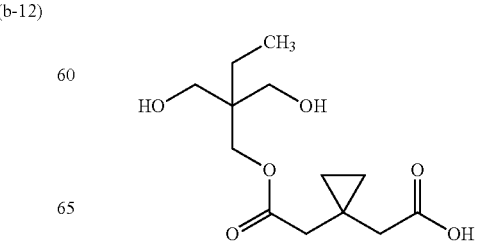
(b-19)

(b-20) 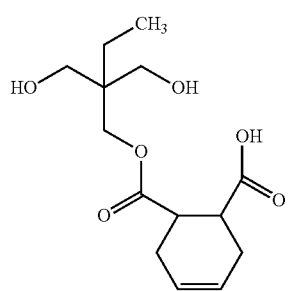
(b-21) 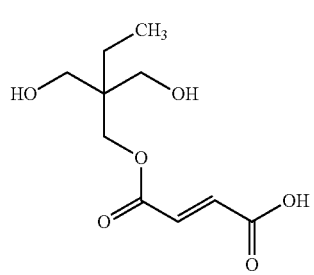
(b-22) 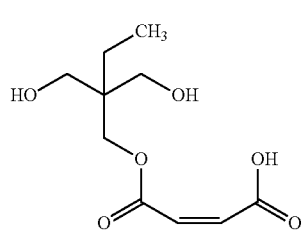
(b-23) 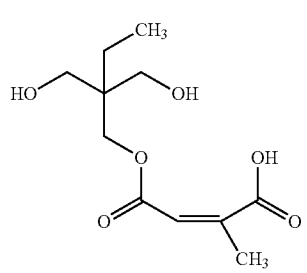
(b-24) 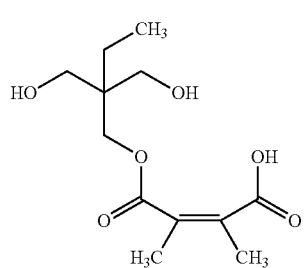
(b-25) 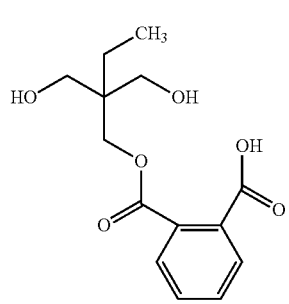
(b-26) 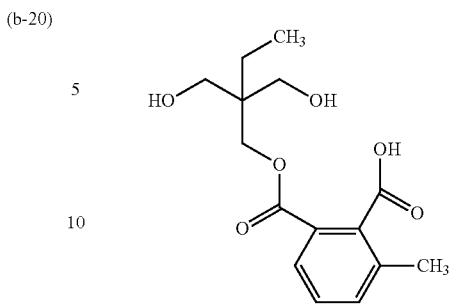
(b-27) 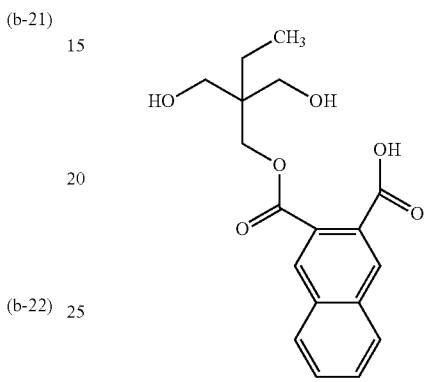
(b-28) 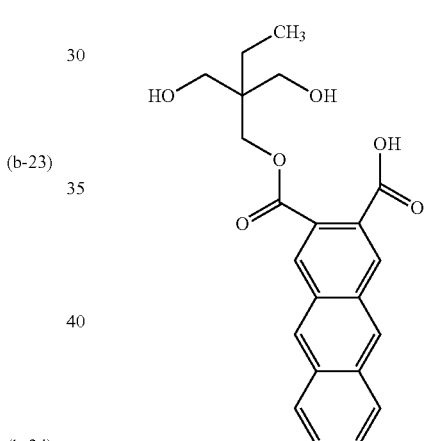
(b-29) 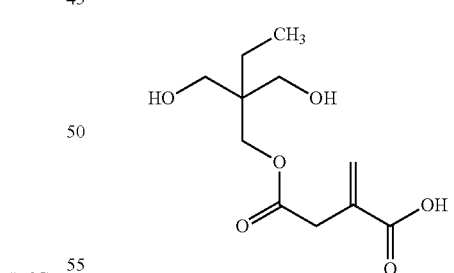
(b-30) 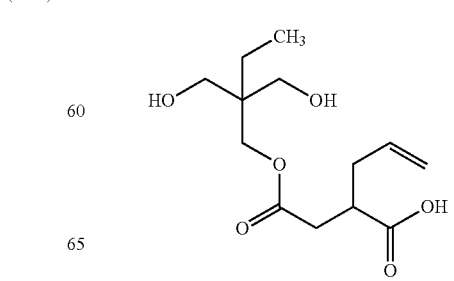

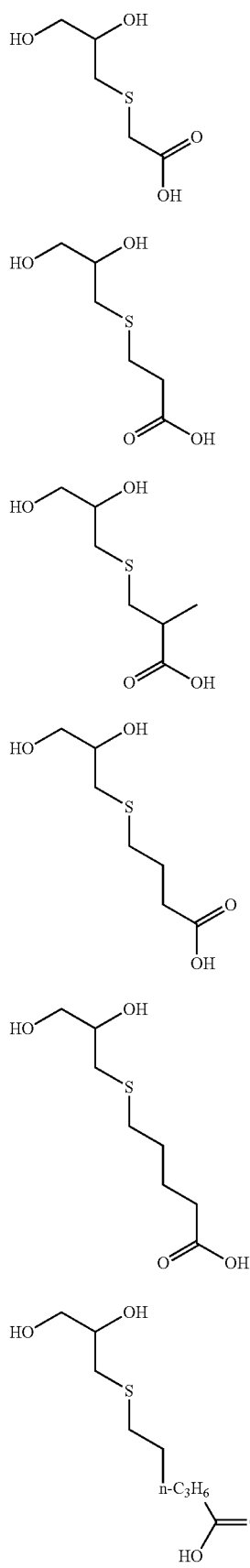
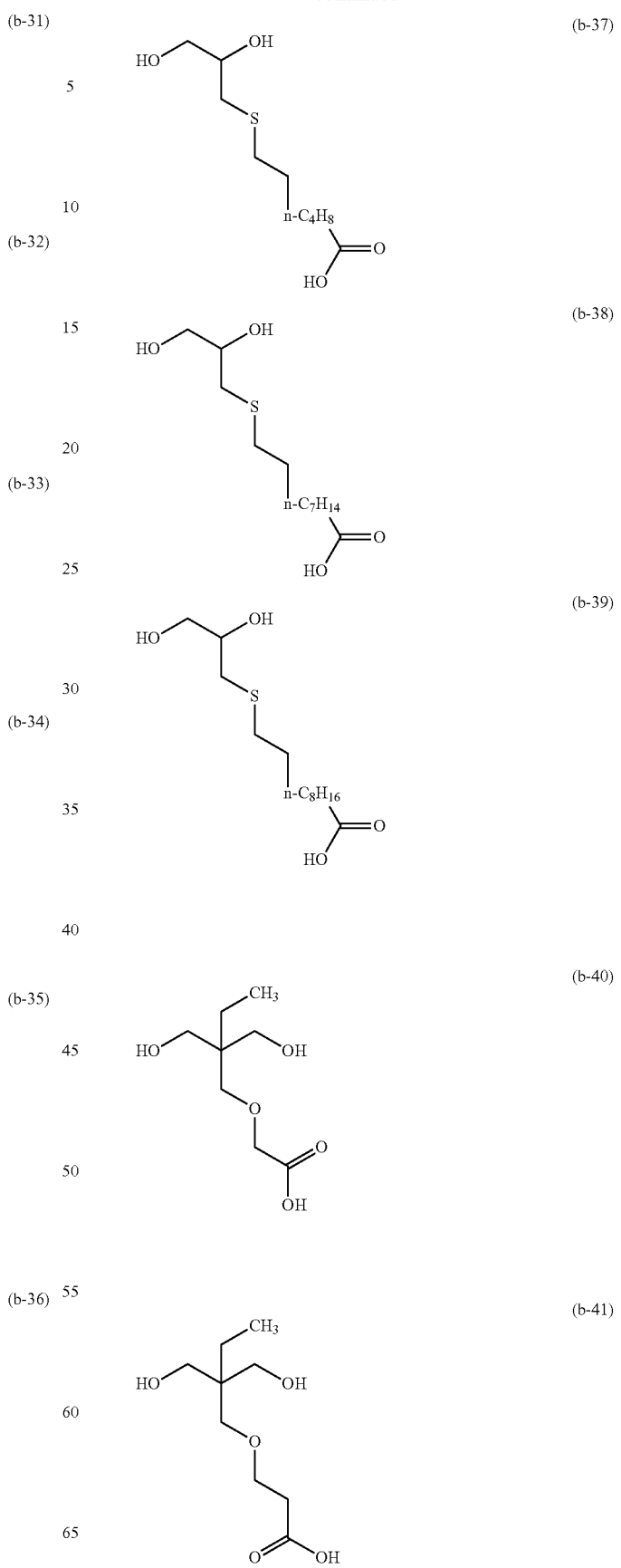

(b-42)
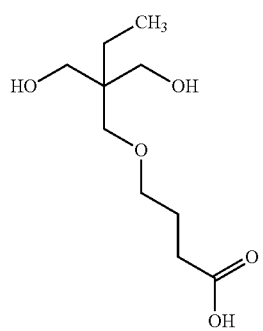
(b-43)
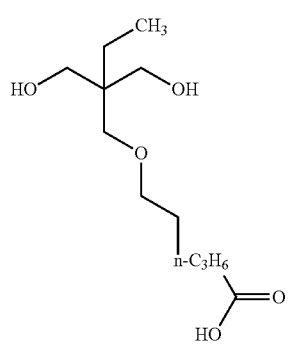
(b-44)
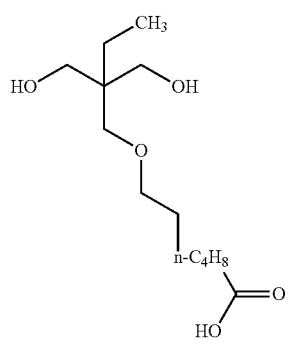
(b-45)
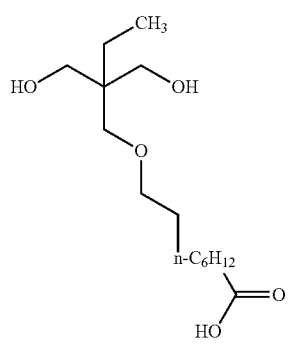
(b-46)
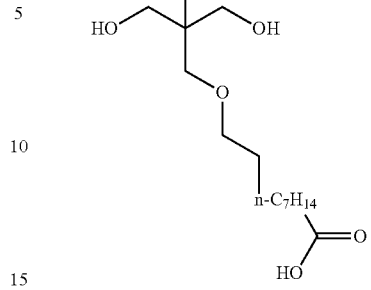
(b-47)
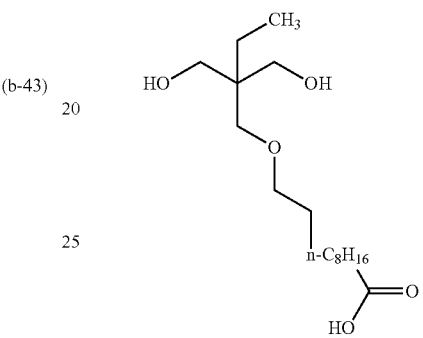
(b-48)
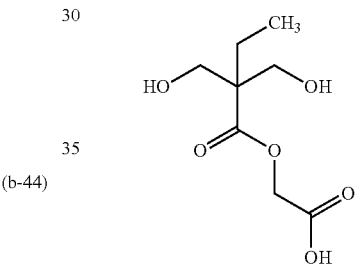
(b-49)
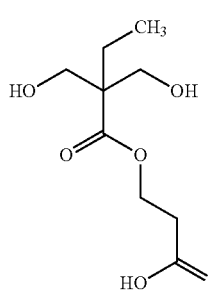
(b-50)
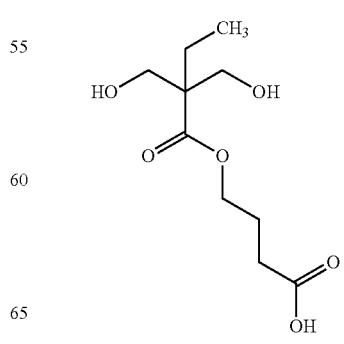

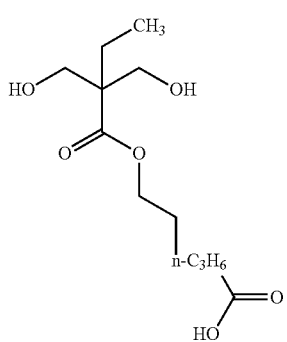
(b-51)
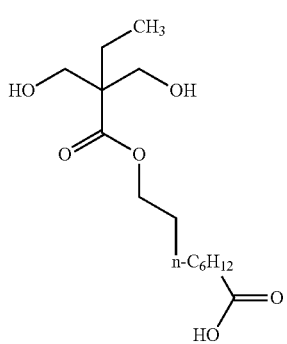
(b-52)
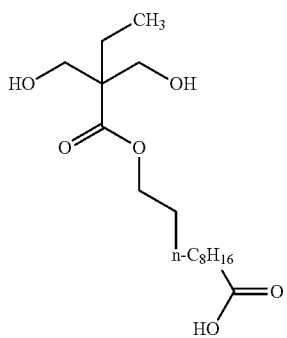
(b-53)
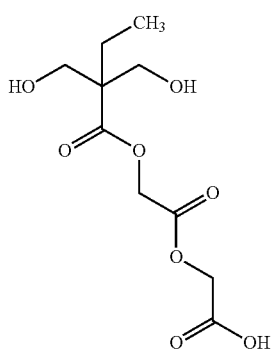
(b-54)
(b-55)
(b-56)
(b-57)
(b-58)
(b-59)
(b-60)
(b-61)

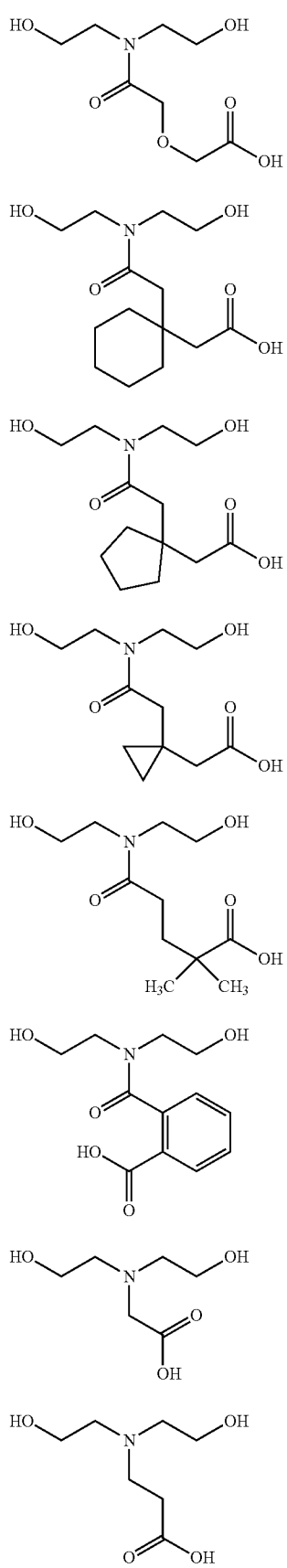
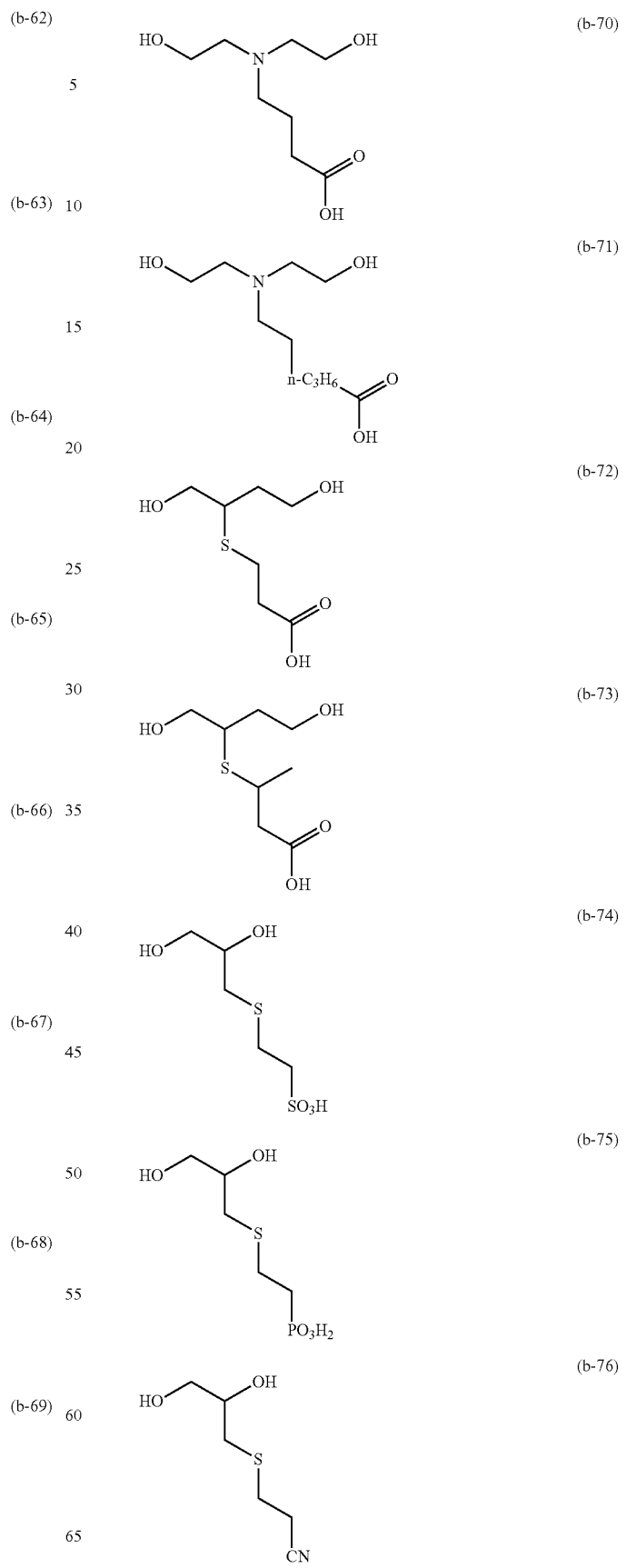

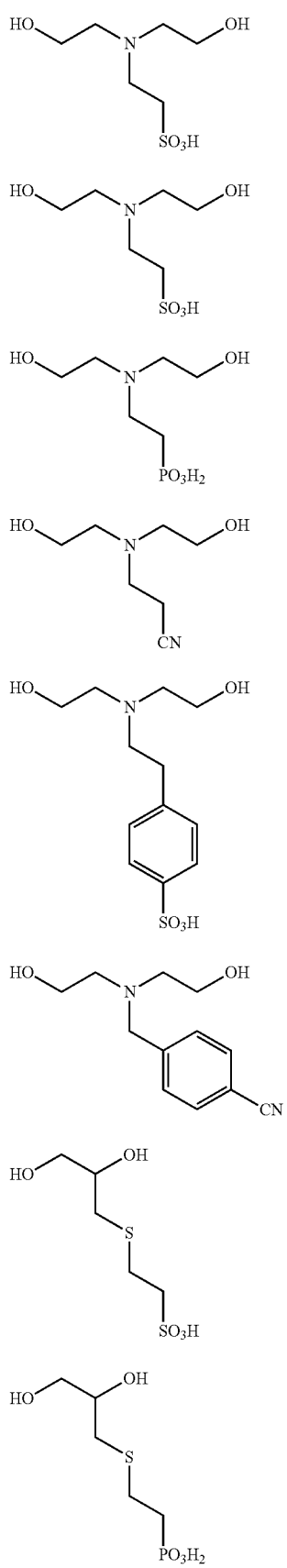
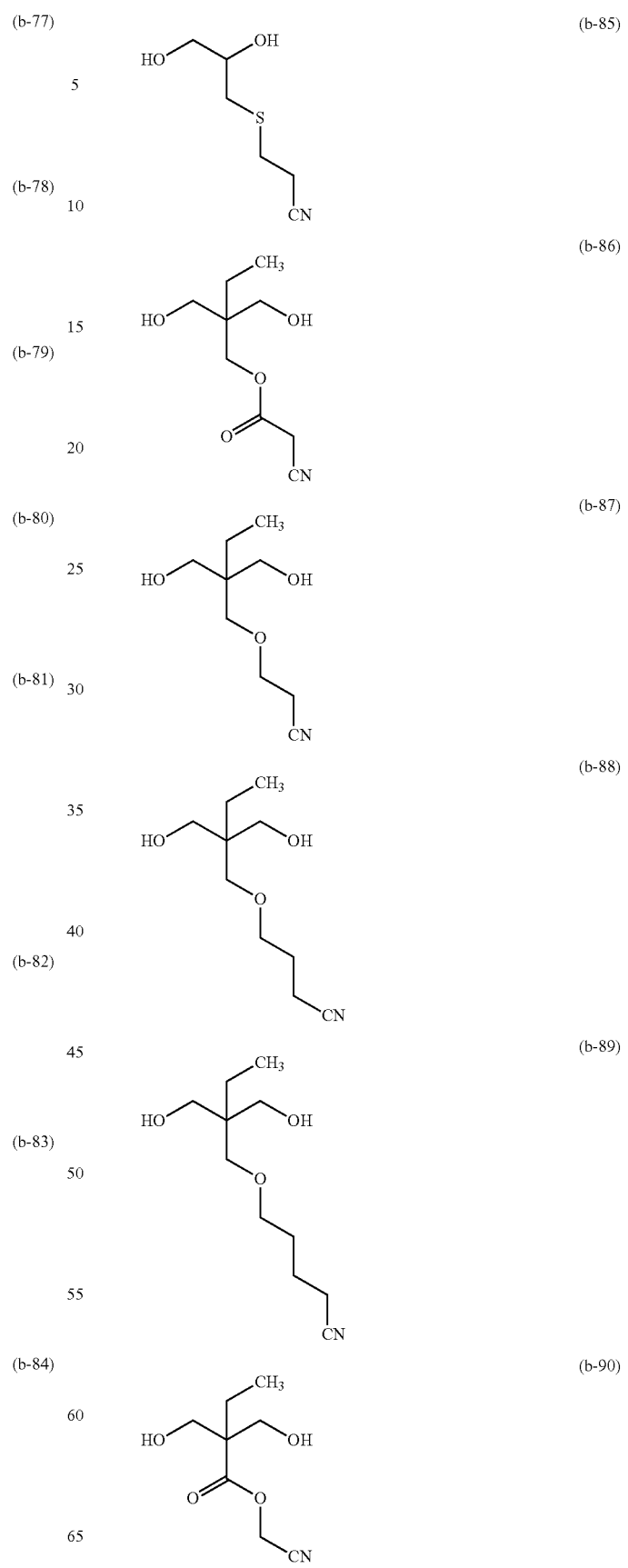

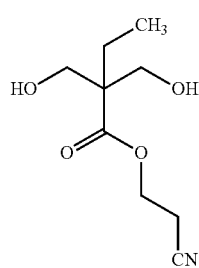
(b-91)
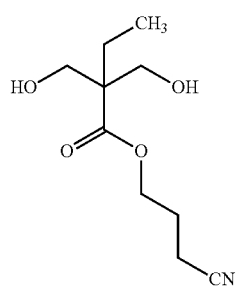
(b-92)
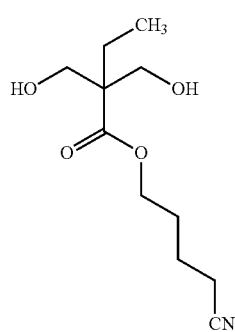
(b-93)
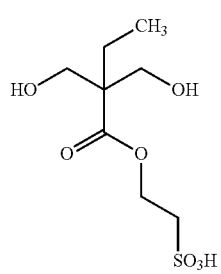
(b-94)
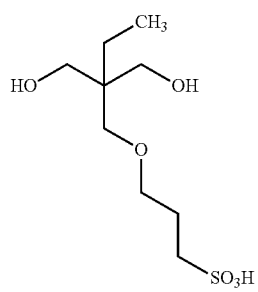
(b-95)
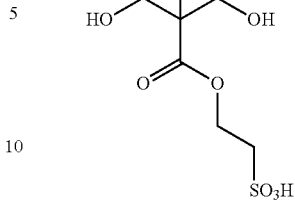
(b-96)
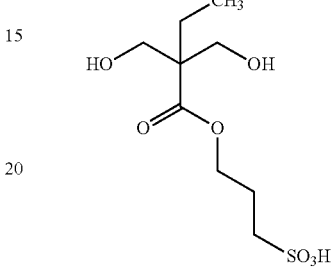
(b-97)
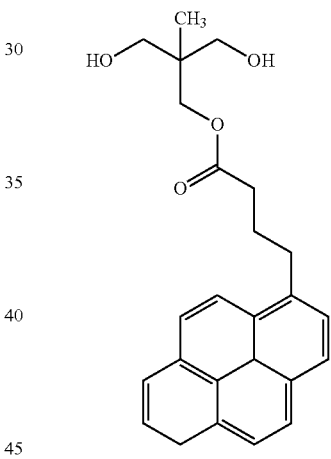
(b-98)
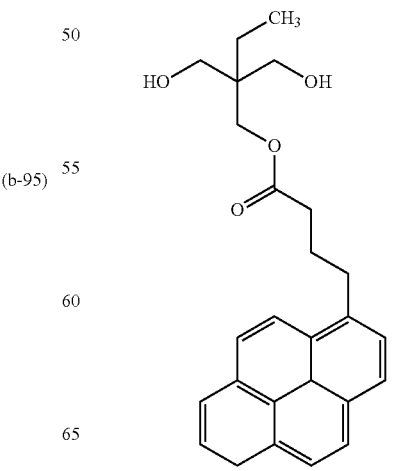
(b-99)

(b-100)
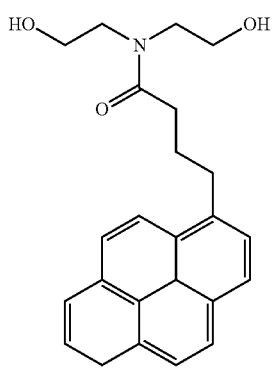
(b-103)
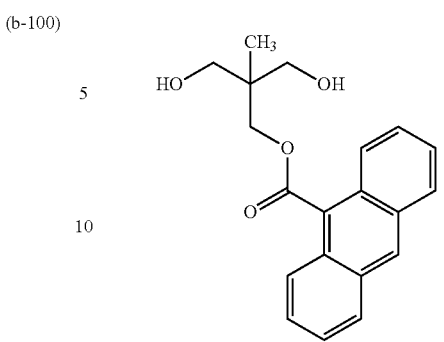
(b-101)
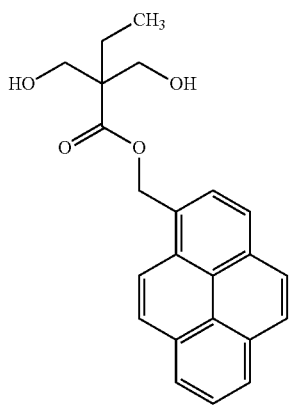
(b-104)
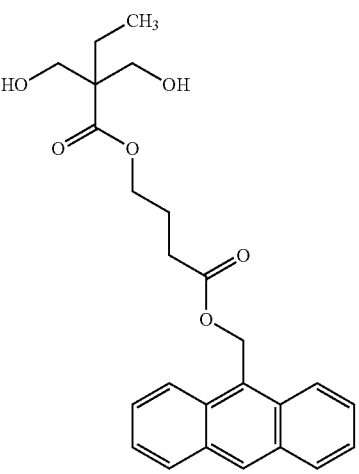
(b-102)
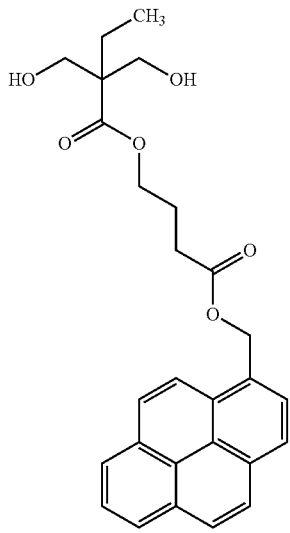
(b-105)
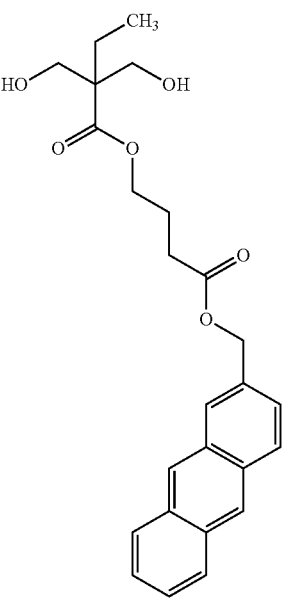

-continued

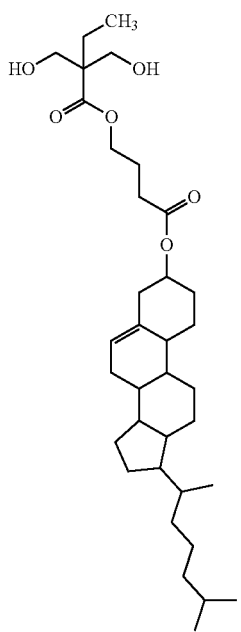

(b-106)

The binder (B) is not particularly limited as long as the binder has at least one of the above-described constituent components. The binder (B) preferably has the above-described constituent component and at least one bond of a urethane bond, a urea bond, an amide bond, and an imide bond. The number of bonds that the binder has is preferably one to five.

The bond is not particularly limited as long as the bond is included in the main chain of the polymer and may be any of an aspect in which the bond is included in a repeating unit as a bond that bonds a constituent component that forms the repeating unit and/or an aspect in which the bond is included as a bond that bonds different repeating units. However, the above-described bond is not included in the main chain of a hydrocarbon polymer segment described below.

The binder (B) more preferably has a hard segment and a soft segment.

(Hard Segment)

The hard segment refers to a segment having an aromatic group or a heteroaromatic group, a rigid group such as an aliphatic alicyclic group, or a bond portion enabling the intermolecular packing by an intermolecular hydrogen bond or a π-π interaction in the main chain of the segment and is generally a segment having rigidity, a strong cohesive force, and a fibrous form. In addition, a segment which is a linear or branched aliphatic hydrocarbon group and satisfies the following molecular weight is also classified as the hard segment even in the case of not having the above-described rigid group or the like. A compound that forms the hard segment is referred to as a short-chain compound (for example, a short-chain diol). The hard segment refers to a segment having a molecular weight of less than 300 in the case of paying attention to the molecular weight of a compound having a partial structure that forms the hard segment.

The hard segment is not particularly limited as long as the hard segment has the above-described characteristics, but preferably has at least one selected from a urethane bond, a urea bond, an amide bond, and an imide bond.

The hard segment is more preferably a segment (group) selected from a group I below. In the following formula, * represents a bonding portion.

<Group I>

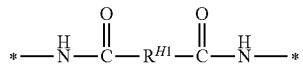

Formula (I-1)

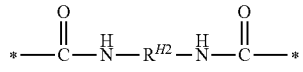

Formula (I-2)

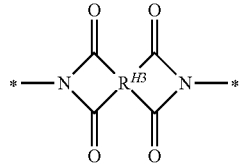

Formula (I-3)

In Formulae (I-1) and (I-2), $R^{H1}$ and $R^{H2}$ each independently represent an alkylene group (the number of carbon atoms is preferably 1 to 18, more preferably 2 to 18, and still more preferably 4 to 13), an arylene group (the number of carbon atoms is preferably 6 to 16 and more preferably 6 to 10), or a combination thereof. Meanwhile, in the case of being linked to an oxygen atom or an imino group ($>NR^N$), Formula (I-2) turns into a urethane group or a urea group. $R^N$ represents a hydrogen atom or an alkyl group (the number of carbon atoms is preferably 1 to 12, more preferably 1 to 6, and still more preferably 1 to 3).

In Formula (I-3), $R^{H3}$ represents an aromatic or aliphatic tetravalent linking group. $R^{H3}$ is preferably a linking group represented by any of Formulae (i) to (iix).

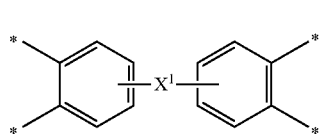

(i)

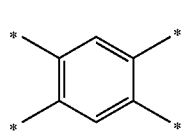

(ii)

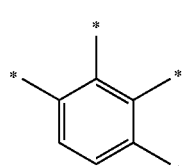

(iii)

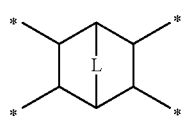

(iv)

-continued (v)
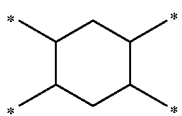

(vi)
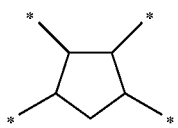

(vii)
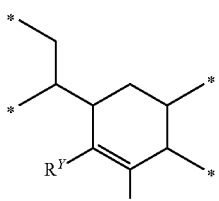

(iix)
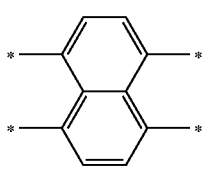

In Formulae (i) to (iix), $X^1$ represents a single bond or a divalent linking group. The divalent linking group is preferably an alkylene group having 1 to 6 carbon atoms (for example, methylene, ethylene, or propylene). As the propylene, 1,3-hexafluoro-2,2-propandiyl is preferred. L represents —CH$_2$=CH$_2$— or —CH$_2$—. $R^X$ and $R^Y$ each independently represent a hydrogen atom or a substituent. In the following formulae, * represents a bonding portion with a carbonyl group.

As the substituent that can be employed as $R^X$ and $R^Y$, an alkyl group (the number of carbon atoms is preferably 1 to 12, more preferably 1 to 6, and still more preferably 1 to 3) or an aryl group (the number of carbon atoms is preferably 6 to 22, more preferably 6 to 14, and still more preferably 6 to 10) is exemplified.

(Soft Segment)

The soft segment refers to a segment having a long-chain linear group or a long-chain branched group in the main chain and is generally a segment that is soft and stretchable. The soft segment is not particularly limited as long as the soft segment has the above-described characteristics, but preferably contains at least one chain of a polyalkylene oxide chain (also referred to as a polyalkylene ether chain, a polyethylene oxide chain or a polypropylene oxide chain is preferred), a polycarbonate chain, a polyester chain, or a silicone chain which has a number-average molecular weight of 300 or more. The soft segment is more preferably a group selected from a group II below. In the following formula, * represents a bonding portion.

<Group II>

Formula (II-1)
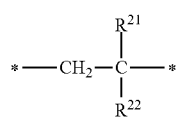

$$*—O—R^{23}—O—*$$ Formula (II-2)

$$*—\overset{O}{\underset{\|}{C}}—R^{23}—\overset{O}{\underset{\|}{C}}—*$$ Formula (II-3)

$$*—HN—R^{23}—NH—*$$ Formula (II-4)

Formula (II-5)

In Formulae (II-1) and (II-5), $R^{21}$ represents a hydrogen atom or an alkyl group (the number of carbon atoms is preferably 1 to 12, more preferably 1 to 6, and still more preferably 1 to 3).

$R^{22}$ represents a substituent which contains a polyalkylene oxide chain (a polyethylene oxide chain or a polypropylene oxide chain is preferred), a polycarbonate chain, a polyester chain, or a silicone chain and has a number-average molecular weight of 300 or more and 200,000 or less. The number-average molecular weight is preferably 500 or more, more preferably 700 or more, and still more preferably 1,000 or more. The upper limit is preferably 100,000 or less and more preferably 10,000 or less.

$R^{22}$ preferably has an alkyl group (the number of carbon atoms is preferably 1 to 12 and more preferably 1 to 6) at the terminal. In addition, $R^{22}$ may have an ether group (—O—), a thioether group (—S—), a carbonyl group (>C=O), an imino group (>NR$^N$) in the alkyl group. $R^N$ is as described above.

In addition, $R^{22}$ may have a heteroatom-containing group or a carbon-carbon unsaturated group described below.

The heteroatom-containing group is preferably at least any of an alcoholic hydroxyl group (hydroxyalkyl group: the number of carbon atoms is preferably 1 to 6 and more preferably 1 to 3), a phenolic hydroxyl group (hydroxyphenyl group), a mercapto group, a carboxy group, a sulfo group, a sulfonamido group, a phosphoric acid group, a cyano group, an amino group, a zwitterion-containing group, a metal hydroxide group, or a metal alkoxide group. Here, the amino group is represented by —N(R$^N$)$_2$, and $R^N$ is as described above. The zwitterion-containing group is specifically a betaine structure (the number of carbon atoms is preferably 1 to 12 and more preferably 1 to 6), as a cation portion, quaternary ammonium, sulfonium, and phosphonium are exemplified, and, as an anion portion, carboxylate and sulfonate are exemplified. The metal hydroxide is specifically a hydroxylsilyl group or a hydroxyl titanyl group. The metal alkoxide is specifically an alkoxysilyl group (the number of carbon atoms is preferably 1 to 12 and more preferably 1 to 6) or an alkoxy titanyl group (the number of carbon atoms is preferably 1 to 12 and more preferably 1 to 6) and more specifically a trimethoxysilyl group, a methyl dimethoxysilyl group, a triethoxysilyl group, a methyl diethoxysilyl group, or a trimethoxy titanyl group.

As the carbon-carbon unsaturated group, a carbon-carbon double bond or a carbon-carbon triple bond is exemplified. As the group including a carbon-carbon double bond, specifically, an acryl group, a methacryl group, a vinyl group, an allyl group, a maleimide group, and the like are exemplified. As the carbon-carbon triple bond, specifically, an ethynyl group, a propargyl group, and the like are exemplified.

$R^{23}$ is a linking group which contains a polyalkylene oxide chain (a polyethylene oxide chain or a polypropylene oxide chain is preferred), a polycarbonate chain, a polyester chain, or a silicone chain and has a number-average molecular weight of 300 or more and 200,000 or less. The number-average molecular weight is preferably 500 or more, more preferably 700 or more, and still more preferably 1,000 or more. The upper limit is preferably 100,000 or less and more preferably 10,000 or less.

$R^{23}$ preferably has an alkyl group (the number of carbon atoms is preferably 1 to 12 and more preferably 1 to 6) at the terminal. In addition, $R^{23}$ may have an ether group (—O—), a thioether group (—S—), a carbonyl group (>C=O), an imino group (>$NR^N$) in the alkyl group. $R^N$ is as described above. In addition, $R^{23}$ may have the above-described heteroatom-containing group or carbon-carbon unsaturated group.

Meanwhile, the number-average molecular weights of $R^{22}$ and $R^{23}$ can be obtained as a polystyrene-equivalent number-average molecular weight in GPC regarding a monomer that is to be combined into a polymer.

The combination of the hard segment and the soft segment that the binder (B) has is not particularly limited, and a combination of at least one hard segment having a urethane bond, a urea bond, an amide bond, or an imide bond and at least one soft segment having the above-described polyalkylene ether chain, polyester chain, polycarbonate chain, or silicone chain is exemplified.

(Hydrocarbon Polymer Segment)

The binder (B) also preferably has a hydrocarbon polymer segment in the main chain.

The hydrocarbon polymer segment refers to a segment made of an oligomer or polymer of a hydrocarbon constituted of a carbon atom and a hydrogen atom (hereinafter, also referred to as the hydrocarbon polymer) and, strictly speaking, refers to a structure in which at least two atoms (for example, hydrogen atoms) or groups (for example, methyl groups) of a polymer constituted of a carbon atom and a hydrogen atom are desorbed.

In the hydrocarbon polymer segment, a functional group for the bond with the hard or soft segment or the like that can be present in the polymer terminal in order is not considered to be included in the hydrocarbon polymer segment.

A hydrocarbon polymer refers to a polymer having a structure in which at least two repeating units are connected together. In addition, the hydrocarbon polymer is preferably constituted of at least 50 carbon atoms.

The hydrocarbon polymer segment is classified as both the hard segment and the soft segment depending on the (number-average) molecular weight or the like; however, in the present invention, is differentiated from the respective segments described above since the segment is made of an oligomer or a polymer.

The number-average molecular weight of the hydrocarbon polymer segment is preferably 1,000 or more and less than 1,000,000, more preferably 1,000 or more and less than 100,000, and still more preferably 1,000 or more and less than 10,000 from the viewpoint of improving the particle dispersibility of the binder (B) and obtaining fine particles.

As the hydrocarbon polymer, the polymer may have a carbon-carbon unsaturated bond or may have a ring structure of an aliphatic ring and/or an aromatic ring. That is, the hydrocarbon polymer needs to be a hydrocarbon polymer constituted of a hydrocarbon selected from an aliphatic hydrocarbon and an aromatic hydrocarbon. A hydrocarbon polymer constituted of an aliphatic hydrocarbon is preferred since the hydrocarbon polymer is flexible and exhibits a steric repulsion effect in the case of being present as polymer particles. This hydrocarbon polymer preferably does not have any ring structure in the main chain and is more preferably an oligomer or polymer of a linear or branched aliphatic hydrocarbon.

The hydrocarbon polymer is preferably an elastomer, and specific examples thereof include a diene-based elastomer having a double bond in the main chain and a non-diene-based elastomer having no double bond in the main chain. Examples of the diene-based elastomer include styrene-butadiene rubber (SBR), styrene-ethylene-butadiene rubber (SEBR), butyl rubber (UR), butadiene rubber (BR), isoprene rubber (IR) ethylene-propylene-diene rubber, and the like. Examples of the non-diene-based elastomer include olefin-based elastomers such as ethylene-propylene rubber and styrene-ethyl ene-butylene rubber, and hydrogen-reduced elastomers of the diene-based elastomer.

From the viewpoint of synthesizing the binder (B), the hydrocarbon polymer preferably has a functional group for the bond with the above-described segment or the like at the polymer terminal and more preferably has a condensation-polymerizable or polyadditionable functional group. As the condensation-polymerizable functional group, a hydroxy group, a carboxy group, an amino group, a sulfanyl group, an acid anhydride, and the like are exemplified, and, among these, a hydroxy group is preferred.

As the hydrocarbon polymer having the condensation-polymerizable functional group at the polymer terminal, for example, NISSO-PB series (manufactured by Nippon Soda Co., Ltd), KRASOL series (manufactured by Tomoe Engineering Co., Ltd.), PolyVEST-HT series (manufactured by Evonik Japan), poly-bd series (manufactured by Idemitsu Kosan Co., Ltd.), poly-ip series (manufactured by Idemitsu Kosan Co., Ltd.), EPOL (manufactured by Idemitsu Kosan Co., Ltd.), POLY TAIL series (manufactured by Mitsubishi Chemical Corporation), which are all trade names, and the like are preferably used.

The content of the soft segment in the binder (B) is preferably 10% by mass or more, more preferably 20% by mass or more, and still more preferably 30% by mass or more of the total mass of the polymer. The upper limit is preferably 90% by mass or less, more preferably 80% by mass or less, and still more preferably 70% by mass or less.

The content of the soft segment in the binder (B) is preferably 1 mol % or more, more preferably 2 mol % or more, and still more preferably 5 mol % or more of the total molar number of the polymer. The upper limit is preferably 50 mol % or less, more preferably 30 mol % or less, and still more preferably 20 mol % or less.

The content of the hard segment in the binder (B) is preferably 5% by mass or more, more preferably 10% by mass or more, and still more preferably 15% by mass or more of the total mass of the polymer. The upper limit is preferably 60% by mass or less, more preferably 50% by mass or less, and still more preferably 40% by mass or less.

The content of the hard segment in the binder (B) is preferably 50 mol % or more, more preferably 60 mol % or more, and still more preferably 70 mol % or more of the total molar number of the polymer. The upper limit is preferably 99 mol % or less, more preferably 90 mol % or less, and still more preferably 80 mol % or less.

The content of the hydrocarbon polymer segment in the binder (B) is preferably 0% by mass or more, more preferably 5% by mass or more, still more preferably 10% by mass or more, and particularly preferably 20% by mass or more of the total mass of the polymer. The upper limit is preferably 80% by mass or less, more preferably 50% by mass or less, still more preferably 40% by mass or less, and particularly preferably 30% by mass or less.

The content of the hydrocarbon polymer segment in the binder (B) is preferably 0 mol % or more, more preferably 0.05 mol % or more, still more preferably 0.1 mol % or more, and particularly preferably 0.2 mol % or more of the total molar number of the polymer. The upper limit is preferably 10 mol % or less, more preferably 5 mol % or less, and still more preferably 3 mol % or less.

In a case in which the respective segments are adjusted to be in the above-described ranges, the mechanical properties of the polymer that satisfy the scratch resistance and the bend resistance in the present invention are imparted, and, furthermore, an effect of obtaining the uniform dispersibility of the binder in the solid electrolyte composition, the solid electrolyte-containing sheet, or the all-solid state secondary battery, which is preferable.

In the binder (B), the content of the constituent component represented by Formula (1) or Formula (2) is preferably 1% by mass or more, more preferably 2% by mass or more, and still more preferably 3% by mass or more of the total mass of the polymer from the viewpoint of the effects of the present invention. The upper limit is preferably 30% by mass or less, more preferably 20% by mass or less, and still more preferably 10% by mass or less.

In the binder (B), the content of the constituent component represented by Formula (1) or Formula (2) is preferably 5 mol % or more, more preferably 10 mol % or more, and still more preferably 15 mol % or more of the total molar number of the polymer from the viewpoint of the effects of the present invention. The upper limit is preferably 50 mol % or less, more preferably 40 mol % or less, and still more preferably 30 mol % or less.

In the binder (B), in a case in which the constituent component represented by Formula (1) or Formula (2) corresponds to the hard segment, the content of the constituent component represented by Formula (1) or Formula (2) is preferably 5% by mass or more, more preferably 7% by mass or more, and still more preferably 10% by mass or more of the total mass of the hard segment from the viewpoint of the effects of the present invention. The upper limit is preferably 50% by mass or less, more preferably 40% by mass or less, and still more preferably 30% by mass or less.

In the binder (B), in a case in which the constituent component represented by Formula (1) or Formula (2) corresponds to the hard segment, the content of the constituent component represented by Formula (1) or Formula (2) is preferably 7 mol % or more, more preferably 13 mol % or more, and still more preferably 20 mol % or more of the total molar number of the hard segment from the viewpoint of the effects of the present invention. The upper limit is preferably 70 mol % or less, more preferably 60 mol % or less, and still more preferably 50 mol % or less.

The binder (B) is preferably a binder (B) which includes the constituent component represented by Formula (1) or the constituent component represented by Formula (2) and has at least one bond selected from a urethane bond; a urea bond, an amide bond, an imide bond, and an ester bond (hereinafter, referred to as the polymer of the present invention).

The number of each of the constituent components represented by the respective formulae described above that the polymer of the present invention contains needs to be at least one, and the partial structure -$L_{11}$-A and the partial structure -$L_{12}$-A in the respective constituent components each are preferably the partial structure represented by any of Formulae (3) to (7).

In addition, at least one bond selected from a urethane bond, a urea bond, an amide bond, an imide bond, and an ester bond is preferably included in each of the hard segment and the soft segment.

(Adsorptive Functional Group)

The binder (B) preferably has an adsorptive functional group. The adsorptive functional group may be present in a main chain of the polymer other than the constituent components represented by Formula (1) and Formula (2). The adsorptive functional group is capable of enhancing the bonding property by interacting with the inorganic particles of the inorganic solid electrolyte, the active material, the conductive auxiliary agent, or the like. As such a functional group, a "heteroatom-containing group" in a "third component" described in Paragraph [0059] of JP2015-088480A is exemplified.

(Crosslinking Functional Group)

The binder (B) that is used in the present invention preferably has a functional group capable of forming a crosslinking structure by a radical polymerization reaction, a cationic polymerization reaction, or an anionic polymerization reaction (hereinafter, also referred to as the crosslinking functional group). In a case in which the crosslinking functional groups react with each other to form a bond, the binder (B) that is used in the present invention generates a structure crosslinked in polymer particles or between the polymer particles and is capable of improving the strength.

The crosslinking functional group is preferably a group having a carbon-carbon unsaturated bond and/or a cyclic ether group. The group having a carbon-carbon unsaturated bond needs to be a group capable of forming a crosslinking structure by a radical polymerization reaction. As a group having a polymerizable carbon-carbon unsaturated bond, specifically, an alkenyl group (the number of carbon atoms is preferably 2 to 12 and more preferably 2 to 8), an alkynyl group (the number of carbon atoms is preferably 2 to 12 and more preferably 2 to 8), an acryloyl group, and a methacryloyl group are preferably exemplified, and a vinyl group, an allyl group, an ethynyl group, a propargyl group, an acryloyl group, a methacryloyl group, and a 2-trifluoromethylpropenoyl group are more preferably exemplified. The cyclic ether group is capable of forming a crosslinking structure by a cation polymerization reaction, and, specifically, an epoxy group and an oxetanyl group are preferably exemplified.

That is, the binder (B) that is used in the present invention preferably has at least one functional group selected from the following group of functional groups (I).

<Group of Functional Groups (I)>

A group having a carbon-carbon unsaturated bond, an epoxy group, and an oxetanyl group.

As the group having a carbon-carbon unsaturated bond, the above-described groups are preferably exemplified, and, among them, a vinyl group, an ethynyl group, an acryloyl group, a methacryloyl group, or a 2-trifluoromethylpropenoyl group is preferred.

The binder (B) preferably has the crosslinking functional group at the hydrocarbon polymer segment and more preferably has the crosslinking functional group in a hard segment or soft segment. Meanwhile, in a case in which the polymer has a carbon-carbon unsaturated bond in the hydrocarbon polymer (for example, polybutadiene and polyisoprene), the crosslinking functional group constituted of a carbon atom and a hydrogen atom (for example, a vinyl group and a propenyl group) is capable of being present in the hydrocarbon polymer segment.

The content of the crosslinking functional group in the binder (B) is not particularly limited, but the proportion of a repeating unit having the crosslinking functional group in all of the repeating units constituting the binder (B) is preferably 1 to 50 mol % and more preferably 5 to 20 mol %.

The reaction between the crosslinking functional groups may be caused by adding polymerization initiators (radical, cationic, or anionic polymerization initiators) corresponding to the respective crosslinking functional groups to the solid electrolyte composition of the embodiment of the invention and initiating the reaction using these polymerization initiators or may be caused by a redox reaction during the driving of a battery. Meanwhile, the radical polymerization initiator may be any of a thermal radical polymerization initiator that is cleavage by heat and generates an initiation radical and a photoradical polymerization initiator generating an initiation radical with light, an electron beam, or a radioactive ray.

As the polymerization initiator that the solid electrolyte composition of the embodiment of the invention may contain, an ordinarily-used polymerization initiator can be used without any particular limitation.

(Method for Synthesizing Binder (B))

A method for synthesizing the binder (B) will be described below.

The binder (B) can be synthesized by, for example, condensation-polymerizing or polyadding the following compound in a random combination. At this time, in order to combine the constituent component represented by Formula (1) and the constituent component represented by Formula (2) into the main chain, a compound that guides these constituent components is used. For example, as the compound that guides the constituent component represented by Formula (1), a dial compound represented by Formula (1M) illustrated below is preferably exemplified.

The compound that is used for the synthesis of the binder (B) is described in, for example, the section of a polymer having an amide bond, a polymer having an imide bond, a polymer having a urethane bond, and a polymer having a urea bond described in Paragraphs [0067] to [0100] of JP2015-088480A, and these polymers can be preferably used.

The polymer having a urethane bond is obtained by the polyaddition of a diisocyanate compound and a diol compound.

As the diisocyanate compound, a compound described in Paragraphs [0073] to [0084] of JP2015-088480A and the like are exemplified, and 4,4'-diphenylmethane diisocyanate (MDI), 2,4-tolylene diisocyanate (TDI), p-xylylene diisocyanate (XDI), isophorone diisocyanate (IPDI), hexamethylene diisocyanate (HDI), 1,3-di(isocyanate methyl) cyclohexane (CHMDI), or 4,4'-methylene bis(cyclohexyl isocyanate) (H12 MDI) is preferred.

As the diol compound, a compound described in Paragraphs [0094] to [0099] of JP2015-088480A and the like are exemplified, and alkylene glycol, an alcohol compound or an aromatic phenol compound, oligomer diol, a polyester diol compound, polycarbonate diol, or silicone diol is preferred, and ethylene glycol, 1,4-butanediol, 1,3-propanediol, dimethylol propionic acid, dimethylol butanate, polyethylene glycol, polypropylene glycol, polytetraethylene glycol, or polycarbonate diol is more preferred.

In the polymer having a urethane bond, it is preferable that a constituent component made of the diisocyanate compound functions as the hard segment and a constituent component made of the diol compound functions as the soft segment.

In the case of the polymer having a urethane bond, it is possible to use a monoalcohol or a monoamine as a polymerization terminator. The polymerization terminator is introduced to the terminal portion of the main chain. As a method for introducing the soft segment to the terminal, it is possible to use polyalkylene glycol monoalkyl ether (polyethylene glycol monoalkyl ether or polypropylene monoalkyl ether is preferred), polycarbonate diol monoalkyl ether, polyester diol monoalkyl ether, polyester monoalcohol, or the like.

The polymer having a urea bond is obtained by the condensation polymerization of a diisocyanate compound and a diamine compound. As the diisocyanate compound, the above-described diisocyanate compound is exemplified. As the diamine compound, a compound described in Paragraph [0068] of JP2015-088480A and the like are exemplified, and 1,4-butanediamine, 1,3-propanediamine, ethylenediamine, 1,4-cyclohexanediamine, or isophoronediamine is preferred.

The polymer having an amide bond is obtained by the condensation polymerization of a diamine compound and a dicarboxylic acid compound or a dicarboxylic acid chloride compound or the ring-opening polymerization of lactam. The diamine compound is as described above. As the dicarboxylic acid compound or the dicarboxylic acid chloride compound, a compound described in Paragraph [0069] of JP2015-088480A is exemplified, and a compound corresponding to terephthalic acid, isophthalic acid, or an acid chloride of these carboxylic acids is preferred.

The polymer having an imide bond is obtained by the polyaddition of a tetracarboxylic dianhydride and a diamine compound. As the tetracarboxylic dianhydride, a compound described in Paragraph [0086] of JP2015-088480A is exemplified, and 5-(2,5-dioxotetrahydrofuryl)-3-methyl-3-cyclohexene-1,2-dicarboxylic anhydride (THFDAA), 1,2,4,5-cyclohexanetetracarboxylic dianhydride (CHDAA), 4,4'-(2,2-hexafluoroisopropylidene) diphthalic dianhydride (6FDAA), or the like is preferred.

As the diamine compound that is used in the polymer having an imide bond, a compound described in Paragraphs [0087] to [0090] of JP2015-088480A is exemplified.

The polymer having an ester bond is obtained by the condensation of a dicarboxylic acid compound or a dicarboxylic acid chloride compound and a diol compound. Specific examples of the dicarboxylic acid or the dicarboxylic acid chloride and the diol compound are as described above.

A diol compound represented by Formula (1M) illustrated below will be described. In the case of using this diol compound, it is possible to combine the constituent component represented by Formula (1) into the main chain of a polymer to be obtained. That is, this diol compound is a polymer having at least one bond selected from a urethane bond, a urea bond, an amide bond, an imide bond, and an ester bond and is preferably used to synthesize a polymer having the above-described constituent component, but the use thereof is not particularly limited.

The diol compound represented by Formula (1M) is a compound in which the partial structure -$L_{11}$-A in Formula (1) is capable of forming the constituent component represented by any of Formulae (3), (5), (6), and (7).

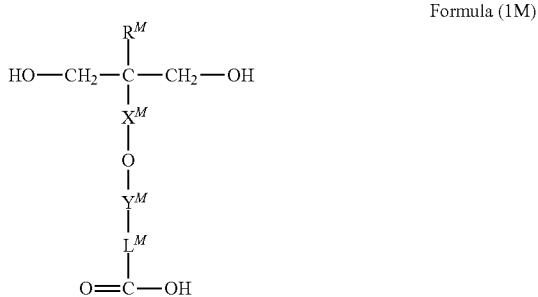

Formula (1M)

In Formula (1M), RM represents a methyl group or an ethyl group.

XM represents a methylene group or a carbonyl group, and YM represents a single bond or a carbonyl group. Here, there is no case in which both XM and YM are carbonyl groups.

LM is an alkylene group having 1 to 18 carbon atoms or an arylene group having 6 to 16 carbon atoms. The alkylene group and the arylene group that can be employed as LM are identical to L2 in Formula (3), and preferred groups are also identical thereto.

The diol compound represented by Formula (1M) is exemplified as specific examples of the constituent component represented by Formula (1), but the present invention is not limited thereto.

The diol compound that guides the constituent component represented by Formula (1) and the constituent component represented by Formula (2) and the diol compound represented by Formula (1M) can be synthesized using an ordinary synthesis method. For example, as the ordinary synthesis method, a method in which a hydroxy group in a polyhydric alcohol compound is protected as necessary, and then a nucleophilic substitution reaction or nucleophilic addition reaction of a nucleophilic residue (a hydroxy group, a carboxy group, an amino group, or a thiol group) into a halogen compound, an acid halogen compound, an ester compound, or an acid anhydride is caused, thereby forming a linking group and a method in which a thiol compound having two hydroxy groups is radical-added or anion-added to an unsaturated bond, thereby forming a linking group are exemplified. In addition, a method in which a linking group is formed in an epoxide compound and then the epoxide is ring-opened using water, thereby obtaining a diol and the like are exemplified.

In addition, as a method for forming the divalent organic group ($L^{11}$ in Formula (1) and $L^{12}$ in Formula (2)), the divalent organic group is obtained by acid-deprotecting a tertiary ester using a method described in Paragraph [0092] and Paragraph [0093] of JP2008-268744A or the like.

In the present specification, compounds, partial structures, or groups that are not clearly expressed as substituted or unsubstituted may have an appropriate substituent in the compounds, partial structures, or groups.

In a case in which a compound, a substituent, a linking group, and the like has an alkyl group, an alkylene group, an alkenyl group, an alkenylene group, an alkynyl group, an alkynylene group, and/or the like, the compound, the substituent, the linking group, and the like may have a cyclic shape or a chain shape, may be linear or branched, and may be substituted or unsubstituted.

As long as the binder (B) has the constituent component represented by Formula (1) or (2), the bonding format of the respective segments is not particularly limited. For example, the bonding format may be a random polymer or block copolymer (condensation polymerization-type or polyaddition-type segmented polymer) of the above-described constituent component, the hard segment as desired, the soft segment as desired, and the hydrocarbon polymer segment as desired. The segmented polymer is preferred from the viewpoint of forming the particles of the binder (B) using a phase inversion emulsification method described below.

The binder (B) can be represented by a formula representing a polymer structure synthesized in an example described below.

The molecular structure of the binder (B) is not particularly limited, and the binder is capable of having a variety of structures such as a linear polymer, a graft polymer, a dendrimer, a star polymer, and a particulate polymer. Among these, a linear polymer or a branched polymer is preferred, and a linear polymer is more preferred. In a case in which the molecular structure is a linear polymer, it becomes easy to form polymer particles using the phase inversion emulsification method described below.

Here, the linear polymer refers not only to a polymer not having a completely branched structure but also to a substantially linear polymer having a short molecular chain other than the main chain. The substantially linear polymer may have a short molecular chain as long as the effects of the present invention are not impaired, for example, it is possible to form particles using the phase inversion emulsification method described below. The linear polymer is different from the graft polymer in the fact that the linear polymer does not have a graft chain other than the main chain.

The shape of the binder (B) that is used in the present invention is not particularly limited and may be a particle shape or an irregular shape in the solid electrolyte composition, the solid electrolyte-containing sheet, or the all-solid state secondary battery.

In the present invention, the binder (B) is preferably particles that are insoluble in the dispersion medium from the viewpoint of the dispersion stability of the solid electrolyte composition and the viewpoint of obtaining an all-solid state secondary battery having a high ion conductivity. Here, "the binder (B) is particles that are insoluble in the dispersion medium" means that, even in a case in which the binder is added to the dispersion medium at 30° C. and left to stand for 24 hours, the average particle diameter does not decrease by 5% or more, and the average particle diameter preferably does not decrease by 3% or more, and the average particle diameter more preferably does not decrease by 1% or more.

Meanwhile, in a state in which the particles of the binder (B) are not dissolved in the dispersion medium, the degree of the average particle diameter changed with respect to that before the addition is 0%.

In addition, in order to suppress a decrease in the inter-particle ion conductivity of the inorganic solid electrolyte or the like, the binder (B) in the solid electrolyte composition preferably has a particle shape, and the average particle diameter is preferably 10 to 1,000 nm and more preferably 100 nm to 500 nm.

Unless particularly otherwise described, the average particle diameter of the binder (B) particles that are used in the present invention refers to an average particle diameter based on measurement conditions and a definition described below.

One percent by mass of a dispersion liquid is prepared by diluting the binder (B) particles using a random solvent (a dispersion medium that is used to prepare the solid electrolyte composition, for example, octane) in a 20 mL sample bottle. The diluted dispersion liquid specimen is irradiated with 1 kHz ultrasonic waves for 10 minutes and then immediately used for testing. Data capturing is carried out 50 times using this dispersion liquid specimen, a laser diffraction/scattering-type particle size distribution measurement instrument LA-920 (trade name, manufactured by Horiba Ltd.), and a silica cell for measurement at a temperature of 25° C., and the obtained volume-average particle diameter is used as the average particle diameter. Regarding other detailed conditions and the like, the description of HS Z 8828:2013 "Particle size analysis-Dynamic light scattering method" is referred to as necessary. Five specimens are produced and measured per level, and the average values thereof are employed.

Meanwhile, the average particle diameter can be measured from the produced all-solid state secondary battery by, for example, disassembling the battery, peeling the electrodes off, then, measuring the average particle diameters of the electrode materials according to the above-described method for measuring the average particle diameter of the polymer particles, and excluding the measurement value of the average particle diameter of particles other than the polymer particles which has been measured in advance.

The mass-average molecular weight of the binder (B) is preferably 5,000 or more and less than 5,000,000, more preferably 5,000 or more or less than 500,000, and still more preferably 5,000 or more and less than 50,000.

In addition, the binder (B) may be used in a solid state or may be used in a state of a polymer particle dispersion liquid or a polymer solution.

The content of the binder (B) in the solid electrolyte composition is preferably 0.1 to 20% by mass, more preferably 0.2 to 10% by mass, and still more preferably 0.5 to 5% by mass with respect to 1.00% by mass of the solid component from the viewpoint of satisfying both the bonding property with the inorganic particles and the ion conductivity.

<(C) Dispersion Medium>

The solid electrolyte composition of the embodiment of the invention preferably contains a dispersion medium for dispersing solid components.

The dispersion medium needs to be a dispersion medium that disperses the respective components described above, and examples thereof include a variety of organic solvents. Specific examples of the dispersion medium include dispersion media described below.

Examples of an alcohol compound solvent include methyl alcohol, ethyl alcohol, 1-propyl alcohol, 2-butanol, ethylene glycol, propylene glycol, glycerin, 1,6-hexanediol, 1,3-butanediol, and 1,4-butanediol.

As an ether compound solvent, alkylene glycol alkyl ethers (ethylene glycol monomethyl ether, ethylene glycol monobutyl ether, diethylene glycol, dipropylene glycol, propylene glycol monomethyl ether, diethyl ene glycol monomethyl ether, triethylene glycol, polyethylene glycol, propylene glycol dimethyl ether, dipropylene glycol monomethyl ether, tripropylene glycol monomethyl ether, diethylene glycol monobutyl ether, diethylene glycol dibutyl ether, and the like), dialkyl ethers (dimethyl ether, diethyl ether, dibutyl ether, and the like), tetrahydrofuran, and dioxane (including each of 1,2-, 1,3-, and 1,4-isomers).

Examples of an amide compound solvent include N,N-dimethylformamide, 1-methyl-2-pyrrolidone, 2-pyrrolidinone, 1,3-dimethyl-2-imidazolidinone, ε-caprolactam, formamide, N-methylformamide, acetamide, N-methylacetamide, N,N-dimethylacetamide, N-methylpropanamide, and hexamethylphosphoric triamide.

Examples of an amino compound solvent include triethylamine and tributylamine.

Examples of a ketone compound solvent include acetone, methyl ethyl ketone, diethyl ketone, dipropyl ketone, and dibutyl ketone.

Examples of an ester-based compound solvent include methyl acetate, ethyl acetate, propyl acetate, butyl acetate, pentyl acetate, hexyl acetate, methyl propionate, ethyl propionate, propyl propionate, butyl propionate, methyl butyrate, ethyl butyrate, propyl butyrate, butyl butyrate, pentyl butyrate, methyl valerate, ethyl valerate, propyl valerate, butyl valerate, methyl caproate, ethyl caproate, propyl caproate, and butyl caproate.

Examples of an aromatic compound solvent include benzene, toluene, ethylbenzene, xylene, and mesitylene.

Examples of an aliphatic compound solvent include hexane, heptane, cyclohexane, methylcyclohexane, ethylcyclohexane, octane, nonane, decane, pentane, cyclopentane, decalin, and cyclooctane.

Examples of a nitrile compound solvent include acetonitrile, propionitrile, and butyronitrile.

The boiling point of the dispersion medium at a normal pressure (1 atmosphere) is preferably 50° C. or higher and more preferably 70° C. or higher. The upper limit is preferably 250° C. or lower and more preferably 220° C. or lower.

The dispersion medium may be used singly or two or more dispersion media may be used in combination.

The dispersion medium (C) that is used in the present invention may be used in a random combination, but a dispersion medium that does not dissolve the particles of the binder (B) is preferred.

Specifically, the dispersion medium (C) that is used in the present invention is preferably an ether compound solvent or a hydrocarbon solvent and more preferably a hydrocarbon solvent since the solid electrolyte composition of the embodiment of the invention is capable of containing the particulate binder (B).

As the hydrocarbon solvent, an aromatic compound solvent is preferably toluene or xylene, and an aliphatic compound solvent is preferably heptane, octane, cyclohexane, or cycloctane.

The content of the dispersion medium in the solid electrolyte composition is not particularly limited and needs to be 0% by mass or more. In a case in which the solid electrolyte composition of the embodiment of the present invention contains the dispersion medium, the content thereof is preferably 20 to 80% by mass, more preferably 30 to 70% by mass, and particularly preferably 40 to 60% by mass.

Regarding the content of the hydrocarbon solvent in the dispersion medium (C), the lower limit value is preferably 50% by mass or more, more preferably 70% by mass or more, and still more preferably 90% by mass or more since the solid electrolyte composition of the embodiment of the invention is capable of containing the particle-shaped binder (B). The upper limit value is not particularly limited, but is preferably 100% by mass.

<(D) Active Materials>

The solid electrolyte composition of the embodiment of the invention may also contain an active material capable of intercalating and deintercalating ions of metal elements belonging to Group I or II of the periodic table.

Examples of the active materials include positive electrode active materials and negative electrode active materials, and transition metal oxides that are positive electrode active materials or metal oxides that are negative electrode active materials are preferred.

In the present invention, the solid electrolyte composition containing the active material (a positive electrode active material and a negative electrode active material) will be referred to as a composition for an electrode (a composition for a positive electrode and a composition for a negative electrode).

(Positive Electrode Active Material)

A positive electrode active material that the solid electrolyte composition of the embodiment of the invention may contain is preferably a positive electrode active material capable of reversibly intercalating and deintercalating lithium ions. The above-described material is not particularly limited as long as the material has the above-described characteristics and may be transition metal oxides, organic substances, elements capable of being complexed with Li such as sulfur, complexes of sulfur and metal, or the like.

Among these, as the positive electrode active material, transition metal oxides are preferably used, and transition metal oxides having a transition metal element $M^a$ (one or more elements selected from Co, Ni, Fe, Mn, Cu, and V) are more preferred. In addition, an element $M^b$ (an element of Group I (Ia) of the metal periodic table other than lithium, an element of Group II (IIa), or an element such as Al, Ga, In, Ge, Sn, Pb, Sb, Bi, Si, P, or B) may be mixed into this transition metal oxide. The amount of the element mixed is preferably 0 to 30 mol % of the amount (100 mol %) of the transition metal element $M^a$. The positive electrode active material is more preferably synthesized by mixing the element into the transition metal oxide so that the molar ratio of Li/$M^a$ reaches 0.3 to 2.2.

Specific examples of the transition metal oxides include transition metal oxides having a bedded salt-type structure (MA), transition metal oxides having a spinel-type structure (MB), lithium-containing transition metal phosphoric acid compounds (MC), lithium-containing transition metal halogenated phosphoric acid compounds (MD), lithium-containing transition metal silicate compounds (ME), and the like.

Specific examples of the transition metal oxides having a bedded salt-type structure (MA) include $LiCoO_2$ (lithium cobalt oxide [LCO]), $LiNi_2O_2$ (lithium nickelate), $LiNi_{0.85}Co_{0.10}Al_{0.05}O_2$ (lithium nickel cobalt aluminum oxide [NCA]), $LiNi_{1/3}Co_{1/3}Mn_{1/3}O_2$ (lithium nickel manganese cobalt oxide [NMC]), and $LiNi_{0.5}Mn_{0.5}O_2$ (lithium manganese nickelate).

Specific examples of the transition metal oxides having a spinel-type structure (NIB) include $LiMn_2O_4$ (LMO), $LiCoMnO_4$, $Li_2FeMn_3O_8$, $Li_2CuMn_3O_8$, $Li_2CrMn_3O_8$, and $Li_2NiMn_3O_8$.

Examples of the lithium-containing transition metal phosphoric acid compounds (MC) include olivine-type iron phosphate salts such as $LiFePO_4$ and $Li_3Fe_2(PO_4)_3$, iron pyrophosphates such as $LiFeP_2O_7$, and cobalt phosphates such as $LiCoPO_4$, and monoclinic nasicon-type vanadium phosphate salt such as $Li_3V_2(PO_4)_3$ (lithium vanadium phosphate).

Examples of the lithium-containing transition metal halogenated phosphoric acid compounds (MD) include iron fluorophosphates such as $Li_2FePO_4F$, manganese fluorophosphates such as $Li_2MnPO_4F$, cobalt fluorophosphates such as $Li_2CoPO_4F$.

Examples of the lithium-containing transition metal silicate compounds (ME) include $Li_2FeSiO_4$, $Li_2MnSiO_4$, $Li_2CoSiO_4$, and the like.

In the present invention, the transition metal oxides having a bedded salt-type structure (MA) is preferred, and LCO, LMO, NCA, or NMC is more preferred.

The shape of the positive electrode active material is not particularly limited, but is preferably a particle shape. The volume-average particle diameter (circle-equivalent average particle diameter) of positive electrode active material particles is not particularly limited. For example, the volume-average particle diameter can be set to 0.1 to 50 μm. In order to provide a predetermined particle diameter to the positive electrode active material, an ordinary crusher or classifier may be used. Positive electrode active materials obtained using a firing method may be used after being washed with water, an acidic aqueous solution, an alkaline aqueous solution, or an organic solvent. The volume-average particle diameter (circle-equivalent average particle diameter) of positive electrode active material particles can be measured using a laser diffraction/scattering-type particle size distribution measurement instrument LA-920 (trade name, manufactured by Horiba Ltd.).

The positive electrode active material may be used singly or two or more positive electrode active materials may be used in combination.

In the case of forming a positive electrode active material layer, the mass (mg) of the positive electrode active material per unit area ($cm^2$) of the positive electrode active material layer (weight per unit area) is not particularly limited and can be appropriately determined depending on the set battery capacity.

The content of the positive electrode active material in the solid electrolyte composition is not particularly limited, but is preferably 10% to 95% by mass, more preferably 30% to 90% by mass, still more preferably 50% to 85% by mass, and particularly preferably 55% to 80% by mass with respect to a solid content of 100% by mass.

(Negative Electrode Active Material)

A negative electrode active material that the solid electrolyte composition of the embodiment of the invention may contain is preferably a negative electrode active material capable of reversibly intercalating and deintercalating lithium ions. The above-described material is not particularly limited as long as the material has the above-described characteristics, and examples thereof include carbonaceous materials, metal oxides such as tin oxide, silicon oxide, metal complex oxides, a lithium single body, lithium alloys such as lithium aluminum alloys, metals capable of forming alloys with lithium such as Sn, Si, Al, and In and the like. Among these, carbonaceous materials or metal complex oxides are preferably used in terms of reliability. In addition, the metal complex oxides are preferably capable of absorbing and deintercalating lithium. The materials are not particularly limited, but preferably contain titanium and/or lithium as constituent components from the viewpoint of high-current density charging and discharging characteristics.

The carbonaceous material that is used as the negative electrode active material is a material substantially consisting of carbon. Examples thereof include petroleum pitch, carbon black such as acetylene black (AB), graphite (natural graphite, artificial graphite such as highly oriented pyrolytic graphite), and carbonaceous material obtained by firing a variety of synthetic resins such as polyacrylonitrile (PAN)-based resins or furfuryl alcohol resins. Furthermore, examples thereof also include a variety of carbon fibers such as PAN-based carbon fibers, cellulose-based carbon fibers, pitch-based carbon fibers, vapor-grown carbon fibers, dehydrated polyvinyl alcohol (PVA)-based carbon fibers, lignin carbon fibers, glassy carbon fibers, and active carbon fibers, mesophase microspheres, graphite whisker, flat graphite, and the like.

The metal oxides and the metal complex oxides being applied as the negative electrode active material are particularly preferably amorphous oxides, and furthermore, chalcogenides which are reaction products between a metal element and an element belonging to Group XVI of the periodic table are also preferably used. The amorphous oxides mentioned herein refer to oxides having a broad scattering band having a peak of a 2θ value in a range of 20° to 40° in an X-ray diffraction method in which Cuba rays are used and may have crystalline diffraction lines.

In a compound group consisting of the amorphous oxides and the chalcogenides, amorphous oxides of semimetal elements and chalcogenides are more preferred, and elements belonging to Groups XIII (MB) to XV (VB) of the periodic table, oxides consisting of one element or a combination of two or more elements of Al, Ga, Si, Sn, Ge, Pb, Sb, and Bi, and chalcogenides are particularly preferred. Specific examples of preferred amorphous oxides and chalcogenides include $Ga_2O_3$, SiO, GeO, SnO, $SnO_2$, PbO, $PbO_2$, $Pb_2O_3$, $Pb_2O_4$, $Pb_3O_4$, $Sb_2O_3$, $Sb_2O_8Bi_2O_3$, $Sb_2O_8Si_2O_3$, $Bi_2O_4$, $SnSiO_3$, GeS, SnS, $SnS_2$, PbS, $PbS_2$, $Sb_2S_3$, $Sb_2S_5$, and $SnSiS_3$. In addition, these amorphous oxides may be complex oxides with lithium oxide, for example, $Li_2SnO_2$.

The negative electrode active material preferably contains a titanium atom. More specifically, $Li_4Ti_5O_{12}$ (lithium titanium oxide [LTO]) is preferred since the volume fluctuation during the absorption and deintercalation of lithium ions is small, and thus the high-speed charging and discharging characteristics are excellent, and the deterioration of electrodes is suppressed, whereby it becomes possible to improve the service lives of lithium ion secondary batteries.

In the present invention, a Si-based negative electrode is also preferably applied. Generally, a Si negative electrode is capable of absorbing a larger number of Li ions than a carbon negative electrode (graphite, acetylene black, or the like). That is, the amount of Li ions absorbed per unit mass increases. Therefore, it is possible to increase the battery capacity. As a result, there is an advantage that the battery driving duration can be extended.

The shape of the negative electrode active material is not particularly limited, but is preferably a particle shape. The average particle diameter of the negative electrode active material is preferably 0.1 to 60 μm. In order to provide a predetermined particle diameter, an ordinary crusher or classifier is used. For example, a mortar, a ball mill, a sand mill, an oscillatory ball mill, a satellite ball mill, a planetary ball mill, a swirling airflow-type jet mill, a sieve, or the like is preferably used. During crushing, it is also possible to carry out wet-type crushing in which water or an organic solvent such as methanol is made to coexist as necessary. In order to provide a desired particle diameter, classification is preferably carried out. The classification method is not particularly limited, and it is possible to use a sieve, a wind power classifier, or the like depending on the necessity. Both of dry-type classification and wet-type classification can be carried out. The average particle diameter of negative electrode active material particles can be measured using the same method as the method for measuring the volume-average particle diameter of the positive electrode active material.

The chemical formulae of the compounds obtained using a firing method can be computed using an inductively coupled plasma (ICY) emission spectroscopic analysis method as a measurement method from the mass difference of powder before and after firing as a convenient method.

The negative electrode active material may be used singly or two or more negative electrode active materials may be used in combination.

In the case of forming a negative electrode active material layer, the mass (mg) of the negative electrode active material per unit area (cm in the negative electrode active material layer (weight per unit area) is not particularly limited and can be appropriately determined depending on the set battery capacity.

The content of the negative electrode active material in the solid electrolyte composition is not particularly limited, but is preferably 10% to 80% by mass and more preferably 20% to 80% by mass with respect to a solid content of 100% by mass.

The surfaces of the positive electrode active material and the negative electrode active material may be coated with a separate metal oxide. Examples of the surface coating agent include metal oxides and the like containing Ti, Nb, Ta, W, Zr, Al, Si, or Li. Specific examples thereof include titanium oxide spinel, tantalum-based oxides, niobium-based oxides, lithium niobate-based compounds, and the like, and specific examples thereof include $Li_4Ti_5O_{12}$, $Li_2Ti_2O_5$, $LiTaO_3$, $LiNbO_3$, $LiAlO_2$, $Li_2ZrO_3$, $Li_2WO_4$, $Li_2TiO_3$, $Li_2B_4O_7$, $Li_3PO_4$, $Li_2MoO_4$, $Li_3BO_3$, $LBO_2$, $Li_2CO_3$, $Li_2SiO_3$, $SiO_2$, $TiO_2$, $ZrO_2$, $Al_2O_3$, $B_2O_3$, and the like.

In addition, a surface treatment may be carried out on the surfaces of electrodes including the positive electrode active material or the negative electrode active material using sulfur, phosphorous, or the like.

Furthermore, the particle surfaces of the positive electrode active material or the negative electrode active material may be treated with an active light ray or an active gas (plasma or the like) before or after the coating of the surfaces.

<(E) Conductive Auxiliary Agent>

The solid electrolyte composition of the embodiment of the invention may also contain a conductive auxiliary agent. The conductive auxiliary agent is not particularly limited, and conductive auxiliary agents that are known as ordinary conductive auxiliary agents can be used. The conductive auxiliary agent may be, for example, graphite such as natural graphite or artificial graphite, carbon black such as acetylene black, Ketjen black, or furnace black, irregular carbon such as needle cokes, a carbon fiber such as a vapor-grown carbon fiber or a carbon nanotube, or a carbonaceous material such as graphene or fullerene which are electron-conductive materials and also may be metal powder or a metal fiber of copper, nickel, or the like, and a conductive polymer such as polyaniline, polypyrrole, polythiophene, polyacetylene, or a polyphenylene derivative may also be used. In addition, these conductive auxiliary agents may be used singly or two or more conductive auxiliary agents may be used.

In the present invention, in the case of jointly using the negative electrode active material and the conductive auxiliary agent, a conductive auxiliary agent that does not intercalate and deintercalated Li and does not function as a negative electrode active material at the time of charging and discharging a battery is regarded as the conductive auxiliary agent. Therefore, in the conductive auxiliary agent, a conductive auxiliary agent capable of functioning as the negative electrode active material in the negative electrode active material layer at the time of charging and discharging a battery is classified not into the conductive auxiliary agent but into the negative electrode active material. Whether or not the conductive auxiliary agent functions as the negative electrode active material at the time of charging and discharging a battery is not unambiguously determined but is determined by the combination with the negative electrode active material.

The content of the conductive auxiliary agent is preferably 0% to 5% by mass and more preferably 0.5% to 3% by mass or more with respect to 100% by mass of the solid contends in the solid electrolyte composition.

<(F) Lithium Salt>

The solid electrolyte composition of the embodiment of the invention may also contain a lithium salt.

The lithium salt is not particularly limited, and, for example, the lithium salt described in Paragraphs 0082 to 0085 of JP2015-088486A is preferred.

The content of the lithium salt is preferably 0 parts by mass or more and more preferably 2 parts by mass or more with respect to 100 parts by mass of the solid electrolyte composition. The upper limit is preferably 20 parts by mass or less and more preferably 10 parts by mass or less.

<Other Binders>

The solid electrolyte composition of the embodiment of the invention may contain an ordinarily-used binder other than the above-described binder (B) as long as the effect of the present invention is not impaired.

As the ordinarily-used binder, an organic polymer is exemplified, and, for example, a binder made of a resin described below is preferably used.

Examples of fluorine-containing resins include polytetrafluoroethylene (PTFE), polyvinylidene difluoride (PVdF), and copolymers of polyvinylidene difluoride and hexafluoropropylene (PVdF-HFP).

Examples of hydrocarbon-based thermoplastic resins include polyethylene, polypropylene, styrene butadiene rubber (SBR), hydrogenated styrene butadiene rubber (HSBR), butylene rubber, acrylonitrile butadiene rubber, polybutadiene, polyisoprene, polyisoprene latex, and the like. Examples of acrylic resins include a variety of (meth)acrylic monomers, (meth)acrylic amide monomers, and copolymers of monomers constituting these resins (preferably copolymers of acrylic acid and methyl acrylate).

In addition, copolymers with other vinyl-based monomers are also preferably used.

Examples of other resins include a polyurethane resin, a polyurea resin, a polyamide resin, a polyimide resin, a polyester resin, a polyether resin, a polycarbonate resin, a cellulose derivative resin, and the like.

These binders may be used singly or two or more binders may be used in combination.

<Dispersant>

The solid electrolyte composition of the embodiment of the invention may also contain a dispersant. The addition of the dispersant enables the suppression of the agglomeration of the electrode active material and the inorganic solid electrolyte and the formation of a uniform active material layer and a uniform solid electrolyte layer even in a case in which the concentration of any of the electrode active material and the inorganic solid electrolyte is high or a case in which the particle diameters are small and the surface area increases. As the dispersant, a dispersant that is ordinarily used for an all-solid state secondary battery can be appropriately selected and used. Generally, a compound intended for particle adsorption and steric repulsion and/or electrostatic repulsion is preferably used.

<Preparation of Solid Electrolyte Composition>

The solid electrolyte composition of the embodiment of the present invention can be prepared by mixing the inorganic solid electrolyte (A), the binder (B), and, as necessary, the dispersion medium (C) or other components using, for example, a variety of mixers. Preferably, the solid electrolyte composition can be prepared as a slurry in which the inorganic solid electrolyte (A), the binder (B), and, as necessary, the dispersion medium (C) or other components are dispersed.

The slurry of the solid electrolyte composition can be prepared using a variety of mixers. The mixing device is not particularly limited, and examples thereof include a ball mill, a beads mill, a planetary mixer, a blade mixer, a roll mill, a kneader, and a disc mill. The mixing conditions are not particularly limited; however, in the case of using a ball mill, the inorganic solid electrolyte and the dispersion medium are preferably mixed together at 150 to 700 rpm (rotation per minute) for one hour to 24 hours.

In the case of preparing a solid electrolyte composition not containing the dispersion medium, the components may be added and mixed at the same time as a dispersion step of the inorganic solid electrolyte (A) or may be separately added and mixed. Meanwhile, the binder (B) may be added and mixed at the same time as the dispersion step of the inorganic solid electrolyte (A) and/or the active material, the dispersant, or the like or may be separately added and mixed. In addition, the form of the binder (B) at the time of being added to and/or mixed with the solid electrolyte composition of the embodiment of the present invention may be the binder (B) itself, a solution of the binder (B), or a dispersion liquid of the binder (B) (a non-aqueous solvent dispersion of the polymer). Among these, the dispersion liquid of the binder is preferred since the dispersion liquid suppresses the decomposition of the inorganic solid electrolyte and is present in a scattered manner on the particle surfaces of the active material and the inorganic solid electrolyte, whereby it is possible to secure the ion conductivity.

[Non-Aqueous Solvent Dispersion of Polymer]

A non-aqueous solvent dispersion of a polymer of an embodiment of the present invention is a dispersion in which the particles of the binder (B) are dispersed in a non-aqueous solvent and can be prepared using, for example, a method for preparing the particles of the binder (B) using the phase inversion emulsification method. As the phase inversion emulsification method, a well-known method can be selected.

In the present specification, the non-aqueous solvent refers to a solvent other than water and is preferably a dispersion medium that can be used to prepare the particles of the binder (B) using the phase inversion emulsification method. Specifically, the dispersion medium (C) is exemplified, and the hydrocarbon solvent (the aromatic compound solvent or the aliphatic compound solvent), an ether solvent, and a ketone solvent are preferred. Meanwhile, the non-aqueous solvent dispersion of a polymer of the embodiment of the present invention may contain water as long as the binder (B) is dispersed as particles, and the water content is preferably 100 ppm or less and more preferably 50 ppm or less.

The non-aqueous solvent dispersion of a polymer of the embodiment of the present invention may not include a solvent that decomposes the inorganic solid electrolyte and is capable of decreasing the ion conductivity and thus can be preferably used for all-solid state secondary batteries. For example, the non-aqueous solvent dispersion of a polymer of the embodiment of the present invention can be added to and mixed with the solid electrolyte composition of the embodiment of the present invention, and thus a complicated step is not required, and a step of removing water or the like remaining in the solvent is not necessary.

In addition, for the non-aqueous solvent dispersion of a polymer of the embodiment of the present invention, it is possible not to use an emulsifier, and thus, in the case of not using an emulsifier, when dried, the non-aqueous solvent dispersion has adhesiveness that is substantially as strong as that in the case of drying a polymer solution. Therefore, the non-aqueous solvent dispersion of a polymer of the embodiment of the present invention is not limited to the use of all-solid state secondary batteries and can also be applied to, for example, adhesives and pressure-sensitive adhesives, and the excellent effects are exhibited.

The content of the binder (B) in the non-aqueous solvent dispersion of a polymer is not particularly limited, but is, for example, preferably 0.1% to 50% by mass and more preferably 1% to 30% by mass with respect to 100% by mass of the non-aqueous solvent dispersion.

[Solid Electrolyte-Containing Sheet]

The solid electrolyte-containing sheet of the embodiment of the invention has a layer containing the inorganic solid electrolyte (A) having a conductivity of an ion of a metal belonging to Group I or II of the periodic table and the binder (B). The binder (B) is the same binder (B) in the solid electrolyte composition of the embodiment of the present invention unless particularly otherwise described.

The solid electrolyte-containing sheet of the embodiment of the invention, particularly, the solid electrolyte-containing sheet of the embodiment of the invention which is produced using the solid electrolyte composition of the embodiment of the invention contains the binder (B) and is thus excellent in terms of the bend resistance, the scratch resistance, and the ion conductivity. As a result, an all-solid state secondary battery into which the solid electrolyte-containing sheet of the embodiment of the invention is considered to have a high ion conductivity and be capable of suppressing the occurrence of short-circuit. In addition, the solid electrolyte-containing sheet can be manufactured using a roll-to-roll method or the like with favorable productivity, furthermore, defects are not easily generated in the solid electrolyte layer or the electrolyte layer, and the active material or the inorganic solid electrolyte does not easily drop from the electrode layer or the solid electrolyte layer. Furthermore, in the case of manufacturing an all-solid state secondary battery using the solid electrolyte-containing sheet, the production aptitude is excellent, and it is possible to improve the manufacturing yield of all-solid state secondary batteries.

The reason that bend resistance, scratch resistance, and an ion conductivity can be imparted to the solid electrolyte-containing sheet of the embodiment of the present invention on a high level has not yet been clarified, but is considered as described below.

The binder that is used in the solid electrolyte-containing sheet has the above-described constituent component. In this constituent component, as illustrated in the respective formulae above, the functional group A is present at a location apart from the main chain of the binder. Therefore, it is considered that the molecular mobility of the functional group A increases at the time of or during the preparation of the solid electrolyte composition and the contact probability with the inorganic particles increases. Therefore, the functional group A and the inorganic particles adhere to each other efficiently and, furthermore, strongly even in a case in which the content of the binder decreases in the solid electrolyte composition. Furthermore, the content of the binder decreases, and thus it is considered that a high ion conductivity can be maintained without excessively coating the inorganic particles.

The solid electrolyte-containing sheet of the embodiment of the invention can be preferably used in all-solid state secondary batteries and is modified in a variety of aspects depending on the uses. Examples thereof include a sheet that is preferably used in a solid electrolyte layer (also referred to as a solid electrolyte-containing sheet for an all-solid state secondary battery or a solid electrolyte-containing sheet), a sheet that is preferably used in an electrode or a laminate of an electrode and a solid electrolyte layer (an electrode sheet for an all-solid state secondary battery), and the like. In the present invention, a variety of sheets described above will be collectively referred to as a sheet for an all-solid state secondary battery in some cases.

The sheet for an all-solid state secondary battery needs to be a sheet having a solid electrolyte layer or an active material layer (electrode layer) and may be a sheet having a solid electrolyte layer or an active material layer (electrode layer) formed on a base material or a sheet formed of a solid electrolyte layer or an active material layer (electrode layer) without having a base material. Hereinafter, a sheet in an aspect in which a solid electrolyte layer or an active material layer (electrode layer) is provided on a base material will be described in detail as an example.

This sheet for an all-solid state secondary battery may further have other layers as long as the sheet has the base material and the solid electrolyte layer or the active material layer, but a sheet containing an active material is classified into an electrode sheet for an all-solid state secondary battery described below. Examples of other layers include a protective layer, a collector, a coating layer (a collector, a solid electrolyte layer, or an active material layer), and the like.

Examples of the solid electrolyte-containing sheet for an all-solid state secondary battery include a sheet having a solid electrolyte layer and, as necessary, a protective layer on a base material in this order.

The base material is not particularly limited as long as the base material is capable of supporting the solid electrolyte layer, and examples thereof include sheet bodies (plate-like bodies) of materials, organic materials, inorganic materials, and the like described in the section of the collector described below Examples of the organic materials include a variety of polymers and the like, and specific examples thereof include polyethylene terephthalate, polypropylene, polyethylene, cellulose, and the like. Examples of the inorganic materials include glass, ceramic, and the like.

Unless particularly otherwise described, the types of components contained in each of the solid electrolyte layer and the active material layer in the solid electrolyte-containing sheet and the content ratios thereof are preferably identical to those in the solid contents of the solid electrolyte composition.

The layer thickness of the solid electrolyte layer in the sheet for an all-solid state secondary battery is identical to the layer thickness of the solid electrolyte layer described in the section of an all-solid state secondary battery of the embodiment of the invention.

This sheet is obtained by forming a film of the solid electrolyte composition of the embodiment of the invention, preferably, a solid electrolyte composition containing the inorganic solid electrolyte (A), the binder (B), and the dispersion medium (C) (by means of application and drying) on the base material (possibly, through other layers) and forming a solid electrolyte layer on the base material. The details will be described below.

Here, the solid electrolyte composition of the embodiment of the invention can be prepared using the above-described method.

An electrode sheet for an all-solid state secondary battery of the embodiment of the invention (also simply referred to as "the electrode sheet") is a sheet for forming an active material layer in an all-solid state secondary battery and an electrode sheet having an active material layer on a metal foil as a collector. This electrode sheet is generally a sheet having a collector and an active material layer, and an aspect of having a collector, an active material layer, and a solid electrolyte layer in this order and an aspect of having a collector, an active material layer, a solid electrolyte layer, and an active material layer in this order are also considered as the electrode sheet.

The constitutions and layer thicknesses of the respective layers constituting the electrode sheet are identical to the constitutions and layer thicknesses of individual layers described in the section of an all-solid state secondary battery of the embodiment of the invention described below.

The electrode sheet is obtained by forming a film of the solid electrolyte composition of the embodiment of the invention which contains the active material (by means of application and drying) on the metal foil and forming an active material layer on the metal foil. The detail will be described below.

[All-Solid State Secondary Battery]

An all-solid state secondary battery of the embodiment of the invention has a positive electrode, a negative electrode facing the positive electrode, and a solid electrolyte layer between the positive electrode and the negative electrode. The positive electrode has a positive electrode active material layer on a positive electrode collector. The negative electrode has a negative electrode active material layer on a negative electrode collector.

At least one layer of the negative electrode active material layer, the positive electrode active material layer, or the solid electrolyte layer is preferably formed using the solid electrolyte composition of the embodiment of the invention and preferably contains the inorganic solid electrolyte (A) and the binder (B).

Unless particularly otherwise described, preferably, the kinds and the content ratio of the components of the active material layers and/or the solid electrolyte layer formed using the solid electrolyte composition are the same as those of the solid contents of the solid electrolyte composition.

Hereinafter, a preferred embodiment of the invention will be described with reference to FIG. 1, but the present invention is not limited thereto.

FIG. 1 is a cross-sectional view schematically illustrating an all-solid state secondary battery (lithium ion secondary battery) according to a preferred embodiment of the present invention. In the case of being seen from the negative electrode side, an all-solid state secondary battery 10 of the present embodiment has a negative electrode collector 1, a negative electrode active material layer 2, a solid electrolyte layer 3, a positive electrode active material layer 4, and a positive electrode collector 5 in this order. The respective layers are in contact with each other and form a laminated structure. In the case of employing the above-described structure, during charging, electrons ($e^-$) are supplied to the negative electrode side, and lithium ions ($Li^+$) are accumulated on the negative electrode side. On the other hand, during discharging, the lithium ions ($Li^+$) accumulated on the negative electrode side return to the positive electrode, and electrons are supplied to an operation portion 6. In the example illustrated in the drawing, an electric bulb is employed as the operation portion 6 and is lit by discharging.

The solid electrolyte composition of the embodiment of the invention can be preferably used as a material used to form the negative electrode active material layer, the positive electrode active material layer, and the solid electrolyte layer. In addition, a solid electrolyte-containing sheet of the embodiment of the invention is preferred as the negative electrode active material layer, the positive electrode active material layer, and the solid electrolyte layer. Hereinafter, an all-solid state secondary battery having a layer constitution of FIG. 1 will also be referred to as an all-solid state secondary battery sheet in some cases.

In the present specification, the positive electrode active material layer (hereinafter, also referred to as the positive electrode layer) and the negative electrode active material layer (hereinafter, also referred to as the negative electrode layer) will be collectively referred to as the electrode layer or the active material layer in some cases. In addition, either or both of the positive electrode active material and the negative electrode active material will be collectively referred to as simply the active material or the electrode active material in some cases (Positive Electrode Active Material Layer, Solid Electrolyte Layer, and Negative Electrode Active Material Layer)

In the all-solid state secondary battery 10, at least one of the positive electrode active material layer, the solid electrolyte layer, or the negative electrode active material layer is produced using the solid electrolyte composition of the embodiment of the invention.

That is, the solid electrolyte layer 3 is produced using the solid electrolyte composition of the embodiment of the invention, and the solid electrolyte layer 3 includes the inorganic solid electrolyte (A) and the binder (B). The solid electrolyte layer, generally, does not include any positive electrode active material and/or any negative electrode active material.

In a case in which the positive electrode active material layer 4 and/or the negative electrode active material layer 2 are produced using the solid electrolyte composition of the embodiment of the invention containing an active material, the positive electrode active material layer 4 and the negative electrode active material layer 2 respectively include a positive electrode active material or a negative electrode active material and further include the inorganic solid electrolyte (A) and the binder (B). In a case in which the active material layers contain the inorganic solid electrolyte, it is possible to improve the ion conductivity.

The kinds of the inorganic solid electrolytes (A) and the binders (B) that the positive electrode active material layer 4, the solid electrolyte layer 3, and the negative electrode active material layer 2 contain may be identical to or different from each other.

In the present invention, any layer of the negative electrode active material layer, the positive electrode active material layer, and the solid electrolyte layer in the all-solid state secondary battery is produced using the solid electrolyte composition containing the inorganic solid electrolyte (A) and the binder (B) and is a layer containing the inorganic solid electrolyte (A) and the binder (B).

In the present invention, one of preferred aspects is that all of the negative electrode active material layer, the positive electrode active material layer, and the solid electrolyte layer in the all-solid state secondary battery are produced using the solid electrolyte composition containing the inorganic solid electrolyte (A) and the binder (B).

The thicknesses of the positive electrode active material layer 4, the solid electrolyte layer 3, and the negative electrode active material layer 2 are not particularly limited. In a case in which the dimensions of ordinary batteries are taken into account, the thicknesses of the respective layers are preferably 10 to 1,000 µm and more preferably 20 µm or more and less than 500 µm. In the all-solid state secondary battery of the embodiment of the invention, the thickness of at least one layer of the positive electrode active material layer 4, the solid electrolyte layer 3, or the negative electrode active material layer 2 is still more preferably 50 µm or more and less than 500 µm.

(Collector (Metal Foil))

The positive electrode collector 5 and the negative electrode collector 1 are preferably an electron conductor.

In the present invention, there are cases in which any or both of the positive electrode collector and the negative electrode collector will be simply referred to as the collector.

As a material forming the positive electrode collector, aluminum, an aluminum alloy, stainless steel, nickel, titanium, or the like, and furthermore, a material obtained by treating the surface of aluminum or stainless steel with carbon, nickel, titanium, or silver (a material forming a thin film) is preferred, and, among these, aluminum and an aluminum alloy are more preferred.

As a material forming the negative electrode collector, aluminum, copper, a copper alloy, stainless steel, nickel, titanium, or the like, and furthermore, a material obtained by treating the surface of aluminum, copper, a copper alloy, or stainless steel with carbon, nickel, titanium, or silver is preferred, and aluminum, copper, a copper alloy, or stainless steel is more preferred.

Regarding the shape of the collector, generally, collectors having a film sheet-like shape are used, but it is also possible to use net-shaped collectors, punched collectors, compacts of lath bodies, porous bodies, foaming bodies, or fiber groups, and the like.

The thickness of the collector is not particularly limited, but is preferably 1 to 500 µm. In addition, the surface of the collector is preferably provided with protrusions and recesses by means of a surface treatment.

In the present invention, a functional layer, member, or the like may be appropriately interposed or disposed between the respective layers of the negative electrode collector, the negative electrode active material layer, the solid electrolyte layer, the positive electrode active material layer, and the positive electrode collector or on the outside thereof. In addition, the respective layers may be composed of a single layer or multiple layers.

(Chassis)

It is possible to produce the basic structure of the all-solid state secondary battery by disposing the respective layers described above. Depending on the use, the basic structure may be directly used as an all-solid state secondary battery, but the basic structure may be used after being enclosed in an appropriate chassis in order to have a dry battery form. The chassis may be a metallic chassis or a resin (plastic) chassis. In a case in which a metallic chassis is used, examples thereof include an aluminum alloy chassis and a stainless-steel chassis. The metallic chassis is preferably classified into a positive electrode-side chassis and a negative electrode-side chassis and electrically connected to the positive electrode collector and the negative electrode collector respectively. The positive electrode-side chassis and the negative electrode-side chassis are preferably integrated by being joined together through a gasket for short circuit prevention.

[Manufacturing of Solid Electrolyte-Containing Sheet]

The solid electrolyte-containing sheet of the embodiment of the invention is obtained by forming a film of the solid electrolyte composition of the embodiment of the invention (preferably containing the dispersion medium (C)) on a base material (possibly, through a different layer) (application and drying) and forming a solid electrolyte layer on the base material.

In the above-described manner, it is possible to produce a solid electrolyte-containing sheet having (a solid electrolyte layer containing) the inorganic solid electrolyte (A) and the binder (B) on a base material. In addition, it is also possible to peel the base material off from the produced solid electrolyte-containing sheet and produce a solid electrolyte-containing sheet formed of a solid electrolyte layer.

Additionally, regarding steps such as application, it is possible to use a method described in the following section of the manufacturing of an all-solid state secondary battery.

The solid electrolyte-containing sheet may also contain a dispersion medium (C) as long as the battery performance is not affected. Specifically, the content of the dispersion medium may be 1 ppm or more and 10,000 ppm or less of the total mass.

The content proportion of the dispersion medium (C) in the solid electrolyte-containing sheet of the embodiment of the invention can be measured using the following method.

A 20 mm×20 mm specimen was cut out from the solid electrolyte-containing sheet by punching and immersed in heavy tetrahydrofuran in a glass bottle. The obtained eluted substance is filtered using a syringe filter, and a quantitative operation by $^1$H-NMR is carried out. The correlation between the $^1$H-NMR peak surface area and the amount of the solvent is obtained by producing a calibration curve.

[All-Solid State Secondary Battery and Manufacturing of Electrode Sheet for all-Solid State Secondary Battery]

The all-solid state secondary battery and the electrode sheet for an all-solid state secondary battery can be manufactured using an ordinary method. Specifically, the all-solid state secondary battery and the electrode sheet for an all-solid state secondary battery can be manufactured by forming the respective layers described above using the solid electrolyte composition of the embodiment of the invention or the like. Hereinafter, the manufacturing method will be described in detail.

The all-solid state secondary battery of the embodiment of the invention can be manufactured using a method including (through) a step of applying the solid electrolyte composition of the embodiment of the invention onto a base material (for example, a metal foil which serves as a collector) and forming a coated film (film manufacturing).

For example, a solid electrolyte composition containing a positive electrode active material is applied as a material for a positive electrode (a composition for a positive electrode) onto a metal foil which is a positive electrode collector so as to form a positive electrode active material layer, thereby producing a positive electrode sheet for an all-solid state secondary battery. Next, a solid electrolyte composition for forming a solid electrolyte layer is applied onto the positive electrode active material layer so as to foiin a solid electrolyte layer. Furthermore, a solid electrolyte composition containing a negative electrode active material is applied as a material for a negative electrode (a composition for a negative electrode) onto the solid electrolyte layer so as to form a negative electrode active material layer. A negative electrode collector (a metal foil) is overlaid on the negative electrode active material layer, whereby it is possible to obtain an all-solid state secondary battery having a structure in which the solid electrolyte layer is sandwiched between the positive electrode active material layer and the negative electrode active material layer. A desired all-solid state secondary battery can be produced by enclosing the all-solid state secondary battery in a chassis as necessary.

In addition, it is also possible to manufacture an all-solid state secondary battery by carrying out the methods for forming the respective layers in a reverse order so as to form a negative electrode active material layer, a solid electrolyte layer, and a positive electrode active material layer on a negative electrode collector and overlaying a positive electrode collector thereon.

As another method, the following method can be exemplified. That is, a positive electrode sheet for an all-solid state secondary battery is produced as described above. In addition, a solid electrolyte composition containing a negative electrode active material is applied as a material for a negative electrode (a composition for a negative electrode) onto a metal foil which is a negative electrode collector so as to form a negative electrode active material layer, thereby producing a negative electrode sheet for an all-solid state secondary battery. Next, a solid electrolyte layer is formed on the active material layer in any one of these sheets as described above. Furthermore, the other one of the positive electrode sheet for an all-solid state secondary battery and the negative electrode sheet for an all-solid state secondary battery is laminated on the solid electrolyte layer so that the solid electrolyte layer and the active material layer come into contact with each other. An all-solid state secondary battery can be manufactured as described above.

As still another method, the following method can be exemplified. That is, a positive electrode sheet for an all-solid state secondary battery and a negative electrode sheet for an all-solid state secondary battery are produced as described above. In addition, separately from the positive electrode sheet for an all-solid state secondary battery and the negative electrode sheet for an all-solid state secondary battery, a solid electrolyte composition is applied onto a base material, thereby producing a solid electrolyte-containing sheet for an all-solid state secondary battery consisting of a solid electrolyte layer. Furthermore, the positive electrode sheet for an all-solid state secondary battery and the negative electrode sheet for an all-solid state secondary battery are laminated together so as to sandwich the solid electrolyte layer that has been peeled off from the base material. An all-solid state secondary battery can be manufactured as described above.

An all-solid state secondary battery can be manufactured by combining the above-described forming methods. For example, a positive electrode sheet for an all-solid state secondary battery, a negative electrode sheet for an all-solid state secondary battery, and a solid electrolyte-containing sheet for an all-solid state secondary battery are produced respectively. Next, a solid electrolyte layer peeled off from a base material is laminated on the negative electrode sheet for an all-solid state secondary battery and is then attached to the positive electrode sheet for an all-solid state secondary battery, whereby an all-solid state secondary battery can be manufactured. In this method, it is also possible to laminate the solid electrolyte layer on the positive electrode sheet for an all-solid state secondary battery and attach the solid electrolyte layer to the negative electrode sheet for an all-solid state secondary battery.

<Formation of Individual Layers (Film Formation)>

The method for applying the solid electrolyte composition is not particularly limited and can be appropriately selected. Examples thereof include coating (preferably wet-type coating), spray coating, spin coating, dip coating, slit coating, stripe coating, and bar coating.

At this time, the solid electrolyte composition may be dried respectively after being applied or may be dried after being applied to multiple layers. The drying temperature is not particularly limited. The lower limit is preferably 30° C. or higher, more preferably 60° C. or higher, and still more preferably 80° C. or higher, and the upper limit is preferably 300° C. or lower, more preferably 250° C. or lower, and still more preferably 200° C. or lower. In a case in which the compositions are heated in the above-described temperature range, it is possible to remove the dispersion medium (C) and form a solid state. In addition, the temperature is not excessively increased, and the respective members of the all-solid state secondary battery are not impaired, which is preferable. Therefore, in the all-solid state secondary battery, excellent total performance is exhibited, and it is possible to obtain a favorable bonding property.

After the production of the applied solid electrolyte composition or the all-solid state secondary battery, the respective layers or the all-solid state secondary battery is preferably pressurized. In addition, the respective layers are also preferably pressurized in a state of being laminated together. Examples of the pressurization method include a hydraulic cylinder pressing machine and the like. The welding pressure is not particularly limited, but is, generally, preferably in a range of 50 to 1,500 MPa.

In addition, the applied solid electrolyte composition may be heated at the same time as pressurization. The heating temperature is not particularly limited, but is generally in a range of 30° C. to 300° C. The respective layers or the all-solid state secondary battery can also be pressed at a temperature higher than the glass transition temperature of the inorganic solid electrolyte.

The pressurization may be carried out in a state in which the applied solvent or dispersion medium has been dried in advance or in a state in which the solvent or the dispersion medium remains.

The respective compositions may be applied at the same time, and the application, the drying, and the pressing may be carried out simultaneously and/or sequentially. The respective compositions may be applied to separate base materials and then laminated by means of transfer.

The atmosphere during the pressurization is not particularly limited and may be any one of in the atmosphere, under the dried air (the dew point: −20° C. or lower), in an inert gas (for example, in an argon gas, in a helium gas, or in a nitrogen gas), and the like.

The pressing time may be a short time (for example, within several hours) at a high pressure or a long time (one day or longer) under the application of an intermediate pressure. In the case of members other than the sheet for an all-solid state secondary battery, for example, the all-solid state secondary battery, it is also possible to use a restraining device (screw fastening pressure or the like) of the all-solid state secondary battery in order to continuously apply an intermediate pressure.

The pressing pressure may be a pressure that is constant or varies with respect to a portion under pressure such as a sheet surface.

The pressing pressure can be changed depending on the area or film thickness of the portion under pressure. In addition, it is also possible to change the same portion with a pressure that varies stepwise.

A pressing surface may be flat or roughened.

<Initialization>

The all-solid state secondary battery manufactured as described above is preferably initialized after the manufacturing or before the use. The initialization is not particularly limited, and it is possible to initialize the all-solid state secondary battery by, for example, carrying out initial charging and discharging in a state in which the pressing pressure is increased and then releasing the pressure up to a pressure at which the all-solid state secondary battery is ordinarily used.

[Usages of all-Solid State Secondary Battery]

The all-solid state secondary battery of the embodiment of the invention can be applied to a variety of usages. Application aspects are not particularly limited, and, in the case of being mounted in electronic devices, examples thereof include notebook computers, pen-based input personal computers, mobile personal computers, e-book players, mobile phones, cordless phone handsets, pagers, handy terminals, portable faxes, mobile copiers, portable printers, headphone stereos, video movies, liquid crystal televisions, handy cleaners, portable CDs, mini discs, electric shavers, transceivers, electronic notebooks, calculators, portable tape recorders, radios, backup power supplies, memory cards, and the like. Additionally, examples of consumer usages include automobiles (electric cars and the like), electric vehicles, motors, lighting equipment, toys, game devices, road conditioners, watches, strobes, cameras, medical devices (pacemakers, hearing aids, shoulder massage devices, and the like), and the like. Furthermore, the all-solid state secondary battery can be used for a variety of military usages and universe usages. In addition, the all-solid state secondary battery can also be combined with solar batteries.

All-solid state secondary batteries refer to secondary batteries having a positive electrode, a negative electrode, and an electrolyte which are all composed of solid. In other words, all-solid state secondary batteries are differentiated from electrolytic solution-type secondary batteries in which a carbonate-based solvent is used as an electrolyte. Among these, the present invention is assumed to be an inorganic all-solid state secondary battery. All-solid state secondary batteries are classified into organic (high-molecular-weight) all-solid state secondary batteries in which a high-molecular-weight compound such as polyethylene oxide is used as an electrolyte and inorganic all-solid state secondary batteries in which the Li—P—S-based glass, LLT, LLZ, or the like is used. Meanwhile, the application of organic compounds to inorganic all-solid state secondary batteries is not inhibited, and organic compounds can also be applied as binders or additives of positive electrode active materials, negative electrode active materials, and inorganic solid electrolytes.

Inorganic solid electrolytes are differentiated from electrolytes in which the above-described high-molecular-weight compound is used as an ion conductive medium (high-molecular-weight electrolyte), and inorganic compounds serve as ion conductive media. Specific examples thereof include the Li—P—S-based glass, LLT, and LLZ. Inorganic solid electrolytes do not emit positive ions (Li ions) and exhibit an ion transportation function. In contrast, there are cases in which materials serving as an ion supply source which is added to electrolytic solutions or solid electrolyte layers and emits positive ions (Li ions) are referred to as electrolytes; however, in the case of being differentiated from electrolytes as the ion transportation materials, the materials are referred to as "electrolyte salts" or "supporting electrolytes". Examples of the electrolyte salts include LiTFSI.

In the present invention, "compositions" refer to mixtures obtained by uniformly mixing two or more components. Here, compositions may partially include agglomeration or uneven distribution as long as the compositions substantially maintain uniformity and exhibit desired effects.

EXAMPLES

Hereinafter, the present invention will be described in more detail on the basis of examples. Meanwhile, the present invention is not interpreted to be limited thereto. "Parts" and "%" that represent compositions in the following examples are mass-based unless particularly otherwise described. In addition, "room temperature" refers to 25° C.

[Synthesis of Sulfide-Based Inorganic Solid Electrolyte: Li—P—S-Based Glass]

As a sulfide-based inorganic solid electrolyte, Li—P—S-based glass was synthesized with reference to a non-patent document of T. Ohtomo, A. Hayashi, M. Tatsumisago, Y. Tsuchida, S. HamGa, K. Kawamoto, Journal of Power Sources, 233, (2013), pp. 231 to 235 and A. Hayashi, S. Hama, H. Morimoto, M. Tatsumisago, T. Minami, Chem. Lett., (2001), pp. 872 and 873.

Specifically, in a globe box under an argon atmosphere (dew point: −70° C.), lithium sulfide ($Li_2S$, manufactured by Aldrich-Sigma, Co. LLC. Purity: >99.98%) (2.42 g) and diphosphorus pentasulfide ($P_2S_5$, manufactured by Aldrich-Sigma, Co. LLC. Purity: >99%) (3.90 g) were respectively weighed, injected into an agate mortar, and mixed using an agate muddler for five minutes. The mixing ratio between $Li_2S$ and $P_2S_5$ ($Li_2S:P_2S_5$) was set to 75:25 in terms of molar ratio.

Zirconia beads (66 g) having a diameter of 5 mm were injected into a 45 mL zirconia container (manufactured by Fritsch Japan Co., Ltd.), the full amount of the mixture of the lithium sulfide and the diphosphorus pentasulfide was injected thereinto, and the container was completely sealed in an argon atmosphere. The container was set in a planetary ball mill P-7 (trade name, manufactured by Fritsch Japan Co., Ltd.) manufactured by Fritsch Japan Co., Ltd., mechanical milling was carried out at a temperature of 25° C. and a rotation speed of 510 rpm for 20 hours, thereby obtaining yellow powder (6.20 g) of a sulfide-based inorganic solid electrolyte (Li—P—S-based glass, expressed as LPS in some cases).

[Synthesis of Binder (B)]

First, diol compounds represented by Formula (1M) that were used to synthesize binders that were used in the examples were synthesized respectively.

Synthesis Example 1-1: Synthesis of Diol Compound (b-2)

Trimethylolpropane (134 g) and acetone (1.3 kg) were injected into a 2 L three-neck flask including a Dean-Stark tube and completely dissolved at room temperature. Pyridinium-p-toluenesulfonate (1.3 g) was added to the obtained solution and heated and refluxed at an internal temperature of 68° C. for two hours. Water that was generated as a byproduct during the above-described process was adsorbed using a molecular sieve 3 A put into the Dean-Stark tube. A reaction liquid was condensed and distilled away, thereby obtaining a precursor (I) (114 g) illustrated below as a transparent liquid (yield: 78%).

Next, the precursor (I) (50 g) and succinic anhydride (32.5 g) were injected into a 200 mL two-neck flask, furthermore, pyridine (27.2 g) was added thereto, and the obtained mixture was heated and stirred at 100° C. for two hours. The obtained reaction liquid was diluted with ethyl acetate and cleaned five times with water (300 mL), and an organic layer was dried and condensed with sodium sulfate, thereby obtaining a precursor (II) (64.2 g) as a light yellow liquid.

The precursor (II) (10 g) and a THF/water liquid mixture (1 vol/1 vol) (30 mL) were injected into a 100 mL two-neck flask, and the precursor (II) was dispersed in the liquid mixture. Pyridinium-p-toluenesulfonate (0.5 g) was added thereto and heated and stirred at 60° C. for two hours. After the end of the reaction, the reaction liquid was completely dissolved and turned into a transparent liquid. Ethyl acetate was added to the obtained reaction liquid to extract an organic substance, and the organic layer was dried and condensed with sodium sulfate, thereby obtaining a diol compound (b-2) (4.3 g) as a white solid (yield: 43%).

The diol compound (b-2) was identified and confirmed from NMR data below.

$^1$H-NMR (300 MHz, DMSO-d6): 0.79 (t, J=6.0 Hz, 3H), 1.25 (q, J=6.0 Hz, 2H), 2.20 (m, 4H), 3.26 (s, 4H), 3.86 (s, 2H), 4.3 (brs, 2H), 12.2 (brs, 1H)

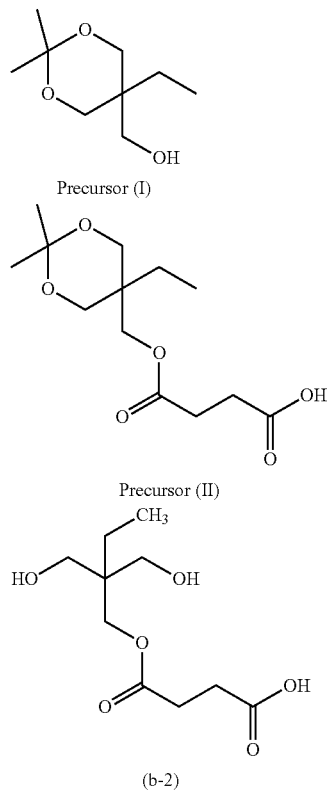

Synthesis Example 1-2: Synthesis of Diol Compound (b-9)

A diol compound (b-9) was obtained in the same manner as in Synthesis Example 1 except for the fact that, in Synthesis Example 1, cis-1,2-cyclohexanedicarboxylic anhydride was used instead of succinic anhydride.

The diol compound (b-9) was identified and confirmed from NMR data below.

$^1$H-NMR (300 MHz, DMSO-d6): 0.79 (t, J=6.0 Hz, 3H), 1.4-1.9 (m, 10H), 2.59 (m, 1H), 2.94 (m, 1H), 3.26 (s, 4H), 3.86 (s, 2H), 4.3 (brs, 2H), 12.2 (brs, 1H)

Synthesis Example 1-3: Synthesis of Diol Compound (b-12)

A diol compound (b-12) was obtained in the same manner as in Synthesis Example 1 except for the fact that, in Synthesis Example 1, glutaric anhydride was used instead of succinic anhydride.

The diol compound (b-12) was identified and confirmed from NMR data below.

$^1$H-NMR (300 MHz, DMSO-d6): 0.79 (t, J=6.0 Hz, 3H), 1.25 (q, J=6.0 Hz, 2H), 1.76 (quintet, J=5.8 Hz, 2H), 2.25 (t, J=5.8 Hz, 2H), 2.33 (t, J=5.8 Hz, 2H), 3.26 (s, 4H), 3.86 (s, 2H), 4.3 (brs, 2H), 12.2 (brs, 1H)

Synthesis Example 1-4: Synthesis of Diol Compound (b-25)

A diol compound (b-25) was obtained in the same manner as in Synthesis Example 1 except for the fact that, in Synthesis Example 1, phthalic anhydride was used instead of succinic anhydride.

The diol compound (b-25) was identified and confirmed from NMR data below.

$^1$H-NMR (300 MHz, DMSO-d6): 0.79 (t, J=6.0 Hz, 3H), 1.25 (q, J=6.0 Hz, 2H), 3.26 (s, 411), 4.01 (s, 2H), 4.3 (brs, 2H), 7.83 (m, 2H), 8.15 (m, 2H), 12.2 (brs, 1H)

Synthesis Example 1-5: Synthesis of Diol Compound (b-36)

Thioglycerol (21.6 g), 5-hexene acid (22.8 g), and methyl ethyl ketone (200 mL) were added to a 500 mL three-neck flask, and the obtained mixture was heated and stirred in a nitrogen atmosphere at 80° C. An azo-based radical polymerization initiator: V-601 (trade name, manufactured by Wako Pure Chemical Industries, Ltd.) (0.53 g) was added thereto and further heated and stirred at 80° C. for six hours. The obtained reaction liquid was condensed, thereby obtaining a diol compound (b-36).

The diol compound (b-36) was identified and confirmed from NMR data below.

$^1$H-NMR (300 MHz, DMSO-d6): 1.3-1.6 (m, 6H), 2.29 (t, 2H), 2.4-2.7 (m, 4H), 3.67 (m, 2H), 3.95 (m, 1H), 4.9-5.7 (brs, 2H), 12.2 (brs, 1H)

Synthesis Example 1-6: Synthesis of Diol Compound (b-40)

The precursor (I) (50 g) was dissolved in THF (100 mL) in a 200 mL two-neck flask. A hydrogenated sodium 60% oil dispersion (12.1 g) was added thereto, heated and stirred at 60° C. for two hours, next, t-butyl bromoacetate (55 g) was added thereto, and continuously further heated and stirred for 24 hours. The obtained reaction liquid was added to a 1N hydrochloric acid water and stirred at room temperature for six hours. An organic layer was extracted with ethyl acetate and dried with sodium sulfate to be condensed. The obtained coarse body was purified with silica gel column chromatography (hexane/ethyl acetate=1/2), thereby obtaining a diol compound (b-40) (30.5 g) as a white solid (yield: 50%).

The diol compound (b-40) was identified and confirmed from NMR data below.

¹H-NMR (300 MHz, DMSO-d6): 0.80 (t, J=6.0 Hz, 3H), 1.28 (q, J=6.0 Hz, 2H), 3.14 (s, 4H), 3.56 (s, 2H), 4.3 (brs, 2H), 4.41 (s, 2H), 12.9 (brs, 1H)

Synthesis Example 1-7: Synthesis of Diol Compound (b-48)

Dimethylolbutanoic acid (148 g) and acetone (1.3 kg) were injected into a 2 L three-neck flask including a Dean-Stark tube and completely dissolved at room temperature. Pyridinium-p-toluenesulfonate (1.3 g) was added to the obtained solution and heated and refluxed at an internal temperature of 68° C. for two hours. Water that was generated as a byproduct during the above-described process was adsorbed using a molecular sieve 3 A put into the Dean-Stark tube. A reaction liquid was condensed and recrystallized with isopropyl alcohol, thereby obtaining a precursor MD (136 g) illustrated below as a white solid (yield: 78%).

Next, the obtained precursor (III) (136 g) was added to the three-neck flask and dissolved in tetrahydrofuran (500 mL). Potassium carbonate (110 g) and t-butyl bromoacetate (178 g) were added thereto and heated and refluxed for six hours. A reaction liquid was condensed, and an organic layer was extracted with ethyl acetate, cleaned with water, and then dried and condensed with sodium sulfate, thereby obtaining a precursor (IV) illustrated below (152 g).

Next, the obtained precursor (IV) (50 g) was added to 1 N hydrochloric acid water (300 mL) and stirred at room temperature for six hours. An organic layer was extracted with ethyl acetate and dried with sodium sulfate to be condensed. The obtained coarse body was purified with silica gel column chromatography (hexane/ethyl acetate=1/2), thereby obtaining a dial compound (b-48) (17.9 g) as a white solid (yield: 50%).

The diol compound (b-48) was identified and confirmed from NMR data below.

¹N-NMR (300 MHz, DMSO-d6): 0.80 (t, J=6.0 Hz, 3H), 1.28 (q, J=6.0 Hz, 2H), 3.14 (s, 4H), 5.02 (s, 2H), 6.4 (hrs, 2H), 12.9 (brs, 1H)

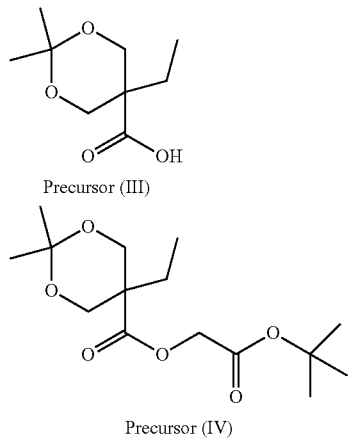 [SMILES: CCC1(C(=O)O)COC(C)(C)OC1 ; CCC1(C(=O)OCC(=O)OC(C)(C)C)COC(C)(C)OC1]

Precursor (III)

Precursor (IV)

Synthesis Example 1-8: Synthesis of Dial Compound (b-57)

Diethanolamine (52 g) was added to a three-neck flask and diluted with pyridine (100 mL). Glutaric anhydride (60 g) was added thereto and heated and stirred at 80° C. for two hours. An organic layer was extracted with ethyl acetate and dried with sodium sulfate to be condensed. The obtained coarse body was purified with silica gel column chromatography (hexane/ethyl acetate=1/2), thereby obtaining a diol compound (b-57).

Synthesis Example 1-9: Synthesis of Diol Compound (b-74)

Thioglycerol (54 g) was added to a three-neck flask and diluted with tetrahydrofuran (500 mL). Vinylsulfonic acid (56 g) was added thereto and heated and stirred under a nitrogen stream at 65° C. An azo-based radical polymerization initiator: V-601 (trade name, manufactured by Wako Pure Chemical Industries, Ltd.) (1.2 g) was added thereto and continuously heated and stirred for eight hours. The obtained reaction liquid was extracted with ethyl acetate and cleaned with a magnesium sulfate saturated aqueous solution, and an organic layer was dried with sodium sulfate to be condensed. The obtained coarse body was purified with silica gel column chromatography (hexane/ethyl acetate=1/4), thereby obtaining a diol compound (b-74).

Synthesis Example 1-10: Synthesis of Diol Compound (b-75)

A diol compound (b-75) was obtained in the same manner as in Synthesis Example 1-9 except for the fact that, in Synthesis Example 1-9, vinylsulfonic acid was changed to vinylphosphonic acid.

Synthesis Example 1-11: Synthesis of Diol Compound (b-89)

A diol compound (b-89) was obtained in the same manner as in Synthesis Example 1-6 except for the fact that, in Synthesis Example 1-6, 5-bromovaleronitrile was used instead of t-butyl bromoacetate.

The diol compound (b-89) was identified and confirmed from NMR data below.

¹H-NMR (300 MHz, DMSO-d6): 0.83 (t, J=6.0 Hz, 3H), 1.64 (q, J=6.0 Hz, 2H), 1.5-1.8 (m, 6H), 3.35 (t, 2H), 3.39 (s, 4H), 3.79 (s, 2H), 4.2 (brs, 2H)

Synthesis Example 1-12: Synthesis of Diol Compound (b-95)

A diol compound (b-95) was obtained in the same manner as in Synthesis Example 1-6 except for the fact that, in Synthesis Example 1-6, 3-bromopropanesulfonic acid was used instead of t-butyl bromoacetate. The diol compound (b-95) was identified and confirmed from NMR data below.

¹H-NMR (300 MHz, DMSO-d6): 0.83 (t, J=6.0 Hz, 3H), 1.64 (q, J=6.0 Hz, 2H), 1.90 (quint, 2H), 3.01 (t, 2H), 3.26 (s, 4H), 3.33 (t, 2H), 3.55 (s, 2H), 4.3 (brs, 2H), 8.5 (brs, 1H)

Synthesis Example 1-13: Synthesis of Diol Compound (b-99)

The precursor (I) (50 g) and pyrenebutanoic acid (83 g) were added to a 1,000 mL three-neck flask and diluted with tetrahydrofuran (500 mL). Pyridine (50 mL) and dicyclohexylcarbodiimide (62 g) were added thereto and stirred at room temperature for six hours. A reaction liquid was condensed, methylene chloride (300 mL) was added thereto, and a precipitated solid was filtered and removed. A filtrate was cleaned with water, then, dried with sodium sulfate, and condensed, thereby obtaining a coarse body of the precursor (V). The coarse body was recrystallized with diisopropyl ether and purified.

Next, the obtained precursor (V) (10 g) and a THF/water liquid mixture (1 vol/1 vol) (30 mL) were injected into a 100 mL two-neck flask, and the precursor (V) was dispersed in the liquid mixture. Pyridinium-p-toluenesulfonate (0.5 g) was added thereto and heated and stirred at 60° C. for two hours. After the end of the reaction, the reaction liquid was completely dissolved and turned into a transparent liquid. Ethyl acetate was added to the obtained reaction liquid to extract an organic substance, and the organic layer was dried and condensed with sodium sulfate, thereby obtaining a diol compound (b-99) (5.9 g) as a white solid (yield: 65%).

The diol compound (b-99) was identified and confirmed from NMR data below.

$^1$H-NMR (300 MHz, DMSO-d6): 0.79 (t, J=6.0 Hz, 3H), 1.25 (q, J=6.0 Hz, 2H), 1.83 (quintet, 2H), 2.32 (t, 2H), 3.07 (t, 2H), 3.26 (s, 4H), 3.86 (s, 2H), 4.3 (brs, 2H), 7.5-8.5 (m, 9H)

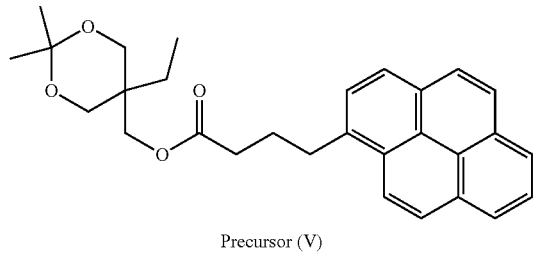 [SMILES: CCC1(COC(=O)CCCc2ccc3ccc4cccc5ccc2c3c45)COC(C)(C)OC1]

Precursor (V)

Synthesis Example 1-12: Synthesis of Diol Compound (b-31)

Thioglycerol (10.8 g) and t-butyl bromoacetate (19.5 g) were added to a 500 mL three-neck flask and diluted with acetone (80 mL). Potassium carbonate (15.8 g) was added thereto and stirred at room temperature for two hours. Ethyl acetate (200 mL) was added thereto, a reaction liquid was cleaned with water, and an organic layer was dried with magnesium sulfate.

Next, p-toluenesulfonic acid monohydrate (5 g) was injected into the organic layer and heated and stirred at 60° C. for two hours. The obtained reaction liquid was extracted with a sodium hydrogen carbonate aqueous solution and added dropwise to 1 N hydrochloric acid water, thereby obtaining a diol compound (b-31) (13.1 g) as a white solid (yield: 81%).

The diol compound (b-31) was identified and confirmed from NMR data below.

$^1$H-NMR (300 MHz, DMSO-d6): 2.4-2.9 (m, 4H), 3.67 (m, 2H), 3.95 (m, 1H), 4.9-5.7 (brs, 2H), 12.2 (brs, 1H)

[Synthesis of Polyurethane Polymer]

Next, polyurethane polymers that were used in the examples were synthesized respectively using the respective synthesized dial compounds.

The obtained polyurethane polymers are represented by Formula (P-1) illustrated below.

Synthesis Example 2-1: Synthesis of Polyurethane Polymer (B-1)

The dial compound synthesized above (b-2) (2.3 g) was injected into a 200 mL three-neck flask and dissolved in tetrahydrofuran (THF) (30 mL). Diphenylmethane diisocyanate (MDI) (2.5 g) was added to this solution, stirred at 65° C., and uniformly dissolved. A bismuth catalyst (trade name: NEOSTAN U-600, manufactured by Nitto Kasei Co., Ltd.) (0.025 g) was added thereto and stirred at 65° C. for six hours, and then the obtained polymer solution was added to methanol and precipitated. The obtained solid was separated into solid and liquid and dried in a vacuum oven at a temperature of 60° C. for 12 hours. A polyurethane polymer (B-1) was obtained as described above.

Synthesis Example 2-2: Synthesis of Polyurethane Polymer (B-3)

A polyurethane polymers (B-3) was obtained in the same manner as in the method for synthesizing the polyurethane polymer (B-1) except for the fact that, in the method for synthesizing the polyurethane polymer (B-1), as the diisocyanate compound, m-xylylene diisocyanate (XDI) was used instead of diphenylmethane diisocyanate, as the diol compound, instead of the diol compound (b-2), 1,3-propanediol (13PG), the diol compound (b-12), and a polyester polyol S-3 (KURARAY POLYOL P1010) were used in proportions (molar ratios) shown in Table 1.

Synthesis Example 2-3 to 2-24: Synthesis of Polyurethane Polymers (B-2) and (B-4) to (B-24)

Polyurethane polymers (B-2) and (B-4) to (B-24) were synthesized respectively in the same manner as in the method for synthesizing the polyurethane polymer (B-1) except for the fact that, in the method for synthesizing the polyurethane polymer (B-1), as the diisocyanate compound and/or the diol compound, compounds shown in Table 1 were used in proportions (molar ratios) shown in Table 1.

Meanwhile, the proportion (50/50) of the diisocyanate compound used for the synthesis of the polymers B-8 and B-22 is a molar ratio. This is also true for the polymer B-47.

Synthesis Example 2-25: Synthesis of Non-Aqueous Solvent Dispersion (B-19L) of Polyurethane Polymer (B-19)

1,4-Butanediol (0.9 g), the diol compound synthesized above (b-12) (6.7 g), and a polycarbonate diol (DURANOL G3452: trade name, manufactured by Asahi Kasei Corporation) (20 g) were injected into a 300 mL three-neck flask and dissolved in methyl ethyl ketone (50 mL). 4,4'-Methylene bis(cyclohexylisocyanate) (H12MDI) (12.5 g) was added thereto and heated and stirred at 75° C. A bismuth catalyst (trade name: NEOSTAN U-600, manufactured by Nitta Kasei Co., Ltd.) (0.055 g) was added thereto and stirred at 75° C. for two hours, and then a THF solution (20 mL) of hydrogenated polyisoprenediol (EPOL: trade name, manufactured by Idemitsu Kosan Co., Ltd.) (8.4 g) was added thereto and further heated and stirred for two hours. The obtained polymer solution was diluted with THF (50 mL), octane (100 mL) was added dropwise for 30 minutes, and the polymer was emulsified. The obtained emulsified liquid was heated to 100° C., and the concentration was adjusted by distilling methyl ethyl ketone and THF, thereby obtaining a 10% by mass octane dispersion (B-19L) of the polyurethane polymer (B-19). The average particle diameter of the polyurethane polymer (B-19) in the dispersion was 250 nm.

Synthesis Example 2-26: Synthesis of Non-Aqueous Solvent Dispersion (B-24L) of Polyurethane Polymer (B-24)

A non-aqueous solvent dispersion (B-24L) was obtained as a 10% by mass octane dispersion liquid in the same manner as in the synthesis of the non-aqueous solvent dispersion (B-19L) except for the fact that, in the synthesis of the non-aqueous solvent dispersion (B-19L), as the diol compound, a compound shown in Table 1 was used in a proportion (molar ratio) shown in Table 1. The average particle diameter of the polyurethane polymer (B-24) in the dispersion was 190 nm.

In Table 1, the constituent components made of the respective compounds are classified into the hard segment, the soft segment, and the hydrocarbon polymer on the basis of the above-described definitions and shown in Table 1. "Mol %" in Table 1 indicates the content (mol %) of each constituent component in the polymer. In Table 1, "-" in "compounds of individual segments" indicates that the individual compounds are not used, and "-" in the "mol %" column indicates "0 mol %". In addition, "Mw" in Table 1 indicates the mass-average molecular weight (a value measured using the above-described method) of each of the synthesized polyurethane polymers.

constituent components in the polymers, and $a1+b1+c1+d1+e1+f1$ is equal to 100 mol %.

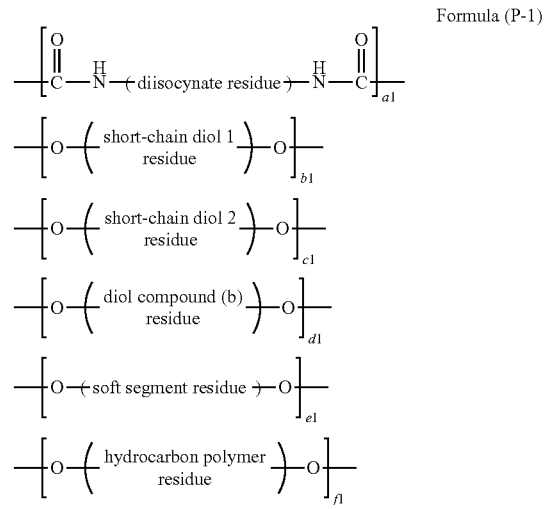

Formula (P-1)

TABLE 1

| Polymer (B) | Diisocyanate | a1 (mol %) | Short-chain diol 1 | b1 (mol %) | Short-chain diol 2 | c1 (mol %) | Diol compound (b) | d1 (mol %) | Soft segment Diol | e1 (mol %) | Hydrocarbon polymer segment Diol | f1 (mol %) | Mw | Kind |
|---|---|---|---|---|---|---|---|---|---|---|---|---|---|---|
| B-1 | MDI | 50 | — | — | — | — | (b-2) | 50 | — | — | — | — | 13400 | Polyurethane |
| B-2 | MDI | 50 | 14BG | 1.5 | DMPA | 10 | (b-9) | P | S-2 | 20 | — | — | 84400 | Polyurethane |
| B-3 | XDI | 50 | 13PG | 10 | — | — | (b-12) | 20 | S-3 | 20 | — | — | 98400 | Polyurethane |
| B-4 | XDI | 50 | 13PG | 10 | DMBA | 10 | (b-36) | 10 | S-1 | 20 | — | — | 84200 | Polyurethane |
| B-5 | TDI | 50 | EG | 10 | — | — | (b-40) | 20 | S-2 | 20 | — | — | 38700 | Polyurethane |
| B-6 | TDI | 50 | — | — | DMBA | 10 | (b-48) | 10 | S-3 | 30 | — | — | 58200 | Polyurethane |
| B-7 | MDI | 50 | EG | 10 | — | — | (b-57) | 20 | S-1 | 17 | H-1 | 3 | 79700 | Polyurethane |
| B-8 | MDI/HDI (50/50) | 50 | EG | 10 | — | — | (b-74) | 20 | S-2 | 17 | H-1 | 3 | 96800 | Polyurethane |
| B-9 | IPDI | 50 | 14BG | 5 | — | — | (b-75) | 25 | S-3 | 20 | — | — | 16000 | Polyurethane |
| B-10 | IPDI | 50 | 14BG | 10 | DMBA | 5 | (b-89) | 15 | S-4 | 17 | H-2 | 3 | 172000 | Polyurethane |
| B-11 | CHMDI | 50 | 13PG | 10 | — | — | (b-95) | 20 | S-5 | 17 | H-2 | 3 | 78900 | Polyurethane |
| B-12 | CHMDI | 50 | 13PG | 10 | DMBA | 5 | (b-31) | 20 | S-7 | 15 | — | — | 67400 | Polyurethane |
| B-13 | H12MDI | 50 | 14BG | 10 | — | — | (b-89) | 20 | S-1 | 17 | H-3 | 3 | 91100 | Polyurethane |
| B-14 | H12MDI | 50 | 14BG | 10 | — | — | (b-95) | 20 | S-2 | 17 | H-4 | 3 | 34800 | Polyurethane |
| B-15 | H12MDI | 50 | 13PG | 10 | — | — | (b-99) | 20 | S-3 | 17 | H-4 | 3 | 60100 | Polyurethane |
| B-16 | H12MDI | 50 | 13PG | 10 | — | — | (b-12) | 20 | S-4 | 20 | — | — | 31500 | Polyurethane |
| B-17 | H12MDI | 50 | — | — | — | — | (b-25) | 37 | S-5 | 10 | H-4 | 3 | 20300 | Polyurethane |
| B-18 | H12MDI | 50 | 14BG | 15 | — | — | (b-12) | 22 | S-5 | 10 | H-4 | 3 | 42000 | Polyurethane |
| B-19 | H12MDI | 50 | 14BG | 10 | — | — | (b-12) | 27 | S-5 | 10 | H-4 | 3 | 94700 | Polyurethane |
| B-20 | H12MDI | 50 | 14BG | 5 | — | — | (b-12) | 32 | 5-5 | 10 | H-4 | 3 | 94200 | Polyurethane |
| B-21 | H12MDI | 50 | — | — | — | — | (b-12) | 37 | S-5 | 10 | H-4 | 3 | 47400 | Polyurethane |
| B-22 | H12MDI/HDI (50/50) | 50 | 14BG | 13 | — | — | (b-12) | 20 | S-6 | 17 | — | — | 131000 | Polyurethane |
| B-23 | H12MDI | 50 | 14BG | 10 | DMBA | 2 | (b-25) | 20 | S-7 | 15 | H-4 | 3 | 95300 | Polyurethane |
| B-24 | H12MDI | 50 | 149G | 10 | DMBA | 2 | (b-99) | 20 | S-6 | 15 | H-4 | 3 | 38800 | Polyurethane |

Hereinafter, what has been described above is true for the synthesis of the binder (B) (Table 2 to Table 5).

The obtained polyurethane polymers are represented by Formula (P-1).

In Formula (P-1), "residue" refers to a partial structure other than a —OH group and a —NCO group that are reactive groups at the terminal of the compound in the compounds used for the synthesis of the polyurethane polymers (refer to Table 1). In addition, a1, b1, c1, d1, e1, and f1 each represent the contents (mol %) of the respective (Note of Table)
MDI: 4,4'-Diphenylmethane diisocyanate
XDI: p-Xylylene diisocyanate
TDI: 2,4-Tolylene diisocyanate
IPDI: Isophorone diisocyanate
CHMDI: 1,3-Di(isocyanate methyl) cyclohexane
H12MDI: 4,4'-Methylene bis(cyclohexylisocyanate)
HDI: Hexamethylene diisocyanate
14BG: 1,4-Butanediol
13PG: 1,3-Propanediol EG: Ethylene glycol
DMPA: Dimethylolpropionic acid
DMBA: Dimethylolbutaonic acid
S-1: Polyethylene glycol (PEG-600, number-average molecular weight: 600)
S-2: Polytetraethylene glycol (PTEG1000, number-average molecular weight: 1,000)
S-3: Polyester polyol (KURARAY POLYOL P1010, number-average molecular weight: 1,000)
S-4: Polycarbonatediol (DURANOL T5650J, number-average molecular weight: 800)
S-5: Polycarbonatediol (DURANOL G3452, number-average molecular weight: 2,000)
S-6: Polycarbonatediol (ETERNACOLL UH100 G3452, number-average molecular weight: 1,000)
S-7: Both-end hydroxy-terminated modified silicone (KF-6003, number-average molecular weight: 5,000)
H-1: Polybutadienediol (Polybd R-45HT, number-average molecular weight: 2,800, manufactured by Idemitsu Kosan Co., Ltd.)
H-2: Polyisoprenediol (Polyip, number-average molecular weight: 2,800, manufactured by Idemitsu Kosan Co., Ltd.)
H-3: Hydrogenated polybutadienediol (NISSO-PB GI-2000, number-average molecular weight: 2,100, manufactured by Idemitsu Kosan Co., Ltd.)
H-4: Hydrogenated polyisoprenediol (EPOL, number-average molecular weight: 2,500, manufactured by Idemitsu Kosan Co., Ltd.)

[Synthesis of Polyester Polymers]

Polyester polymers that were used in the examples were synthesized respectively as described below. The obtained polyester polymers are represented by Formula (P-2) below.

Synthesis Example 3-1: Synthesis of Polyester Polymer (B-31)

Ethylene glycol (EG) (0.31 g), the diol compound (b-12) synthesized above (2.5 g), polyethylene glycol 600 (S-1) (5.0 g), and polybutadienediol (H-1, polybd R-45HT, trade name) (4.2 g) were injected into a 200 mL three-neck flask and dissolved in THF (100 mL). This solution was cooled to 5° C. in an ice bath. A THF solution (20 mL) of terephthaloyl chloride (TPC) (5.1 g) was added dropwise thereto for 30 minutes. The obtained mixture was returned to room temperature and further stirred for two hours. The obtained polymer solution was added to methanol, the precipitated solid was separated into solid and liquid and dried in a vacuum oven at a temperature of 60° C. for 12 hours. A polyester polymer (B-31) was obtained as described above.

Synthesis Example 3-2 to 3-7: Synthesis of Polyester Polymers (B-25) to (B-30)

Polyester polymers (B-25) to (B-30) were synthesized respectively in the same manner as in the method for synthesizing the polyester polymer (B-31) except for the fact that, in the method for synthesizing the polyester polymer (B-31), as the acid chloride, the diol compound, and/or the hydrocarbon polymer, compounds shown in Table 2 were used in proportions (molar ratios) shown in Table 2.

The obtained polyester polymers are represented by Formula (P-2).

In Formula (P-2), "residue" refers to a partial structure other than a —COCl group and a —OH group that are reactive groups at the terminal of the compound in the compounds used for the synthesis of the polyester polymers (refer to Table 2). In addition, a2, b2, c2, d2, e2, f2 each represent the contents (mol %) of the respective constituent components in the polymers, and a2+b2+c2+d2+e2+f2 is equal to 100 mol %.

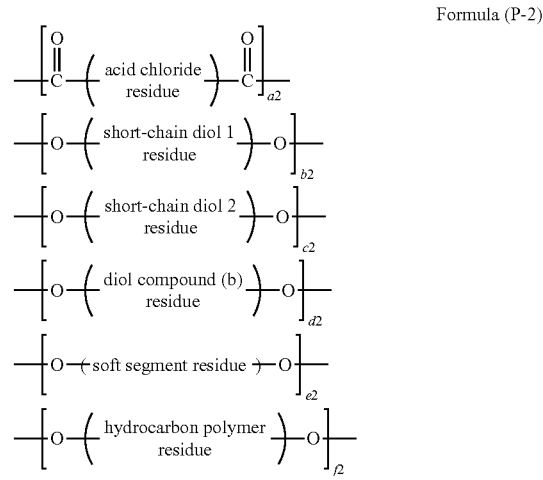

Formula (P-2)

TABLE 2

| Polymer (B) | Acid chloride | a2 (mol %) | Short-chain diol 2 | b2 (mol %) | Short-chain diol 2 | c2 (mol %) | Diol compound (b) | d2 (mol %) | Soft segment Diol | e2 (mol %) | Hydrocarbon polymer segment Diol | f2 (mol %) | Mw | Kind |
|---|---|---|---|---|---|---|---|---|---|---|---|---|---|---|
| B-25 | TPC | 50 | — | — | — | — | (b-12) | 50 | — | — | — | — | 90800 | Polyester |
| B-26 | TPC | 50 | 14BG | 15 | DMPA | 10 | (b-25) | 25 | — | — | — | — | 67300 | Polyester |
| B-27 | TPC | 50 | 13PG | 10 | — | — | (b-74) | 37 | — | — | H-1 | 3 | 58600 | Polyester |
| B-28 | IPC | 50 | 13PG | 10 | DMBA | 10 | (b-75) | 10 | S-1 | 20 | — | — | 112000 | Polyester |
| B-29 | IPC | 50 | EG | 10 | — | — | (b-89) | 20 | S-2 | 17 | H-4 | 3 | 95600 | Polyester |
| B-30 | TPC | 50 | — | — | DMBA | 10 | (b-99) | 30 | S-3 | 7 | H-4 | 3 | 51000 | Polyester |
| B-31 | TPC | 50 | EG | 10 | — | — | (b-12) | 20 | S-1 | 17 | H-1 | 3 | 181000 | Polyester |

(Notes of Table)

TPC: Terephthaloyl dichloride

IPC: Isophthaloyl dichloride

Regarding abbreviations other than the above-described abbreviations, Notes of Table 1 can be referred to.

[Synthesis of Polyamide Polymers]

Polyamide polymers that were used in the examples were synthesized respectively as described below. The obtained polyamide polymers are represented by Formula (P-3) below.

Synthesis Examples 4-1 to 4-7: Synthesis of Polyamide Polymers (B-32) to (B-38)

Polyamide polymers (B-32) to (B-38) were synthesized respectively in the same manner as in the method for synthesizing the polyester polymer (B-31) except for the fact that, in the method for synthesizing the polyester polymer (B-31), as shown in Table 3, the acid chloride and/or the diol compound, the diamine compound, and the hydrocarbon polymer were respectively used in proportions (molar ratios) shown in Table 3.

The obtained polyamide polymers are represented by Formula (P-3).

In Formula (P-3), "residue" refers to a partial structure other than a —OH group, a —COCl group, and a —NH$_2$ group that are reactive groups at the terminal of the compound in the compounds used for the synthesis of the polyamide polymers (refer to Table 3). In addition, a3, b3, d3, e3, and f3 each represent the contents (mol %) of the respective constituent components in the polymers, and a3+b3+d3+e3+f3 is equal to 100 mol %.

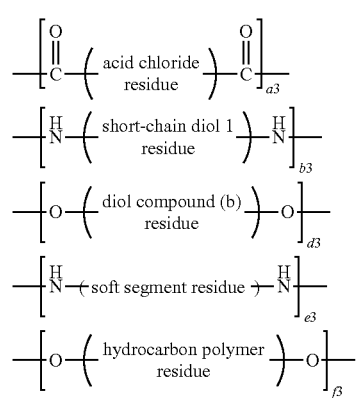

Formula (P-3)

S-8: Terminal diamine polyethylene propylene glycol (JEFFAMINE ED600, number-average molecular weight: 600, manufactured by Huntsman Corporation)

S-9: Terminal diamine polyethylene propylene glycol (JEFFAMINE ED900, number-average molecular weight: 900, manufactured by Huntsman Corporation)

S-10: Terminal diamine polyethylene propylene glycol (JEFFAMINE ED2003, number-average molecular weight: 2,000, manufactured by Huntsman Corporation)

S-11: Terminal diamine polypropylene glycol (number-average molecular weight: 400, manufactured by Aldrich-Sigma, Co. LLC.)

S-12: Terminal diamine silicone (KF-8008, number-average molecular weight: 11,000, manufactured by Shin-Etsu Chemical Co., Ltd.)

Regarding abbreviations other than the above-described abbreviations, Notes of Table 1 and Table 2 can be referred to.

[Synthesis of Polyurea Polymers]

Polyurea polymers that were used in the examples were synthesized respectively as described below. The obtained polyurea polymers are represented by Formula (P-4) below.

Synthesis Example 5-1 to 5-11: Synthesis of Polyurea Polymers (B-39) to (B-49)

Polyurea polymers (B-39) to (B-49) were synthesized respectively in the same manner as in the method for synthesizing the polyurethane polymer (B-1) except for the fact that, in the method for synthesizing the polyurethane polymer (B-1), instead of the diisocyanate compound and the diol compound, diisocyanate compounds, diol compounds, diamine compounds, and hydrocarbon polymers shown in Table 4 were used in proportions (molar ratios) shown in Table 4.

The obtained polyurea polymers are represented by Formula (P-4).

In Formula (P-4), "residue" refers to a partial structure other than a —OH group, a —NH$_2$ group, and a —NCO group that are reactive groups at the terminal of the compound in the compounds used for the synthesis of the polyurea polymers (refer to Table 4). In addition, a4, b4, d4, e4, and f4 each represent the contents (mol %) of the respective constituent components in the polymers, and a4+b4+d4+e4+f4 is equal to 100 mol %.

TABLE 3

| Polymer (B) | Hard segment | | | | | Soft segment | | Hydrocarbon polymer segment | | Mw | Kind |
| --- | --- | --- | --- | --- | --- | --- | --- | --- | --- | --- | --- |
| | Acid chloride | a3 (mol %) | Short-chain diol 3 | b3 (mol %) | Short-chain diol 3 | Diol compound (b) | e3 (mol %) | Diol | f3 (mol %) | | |
| B-32 | TPC | 50 | EDA | 5 | (b-12) | 45 | — | — | — | — | 27600 | Polyamide |
| B-33 | TPC | 50 | EDA | 15 | (b-25) | 35 | — | — | — | — | 180000 | Polyamide |
| B-34 | TPC | 50 | 13PDA | 10 | (b-74) | 20 | S-8 | 17 | H-1 | 3 | 17800 | Polyamide |
| B-35 | IPC | 50 | 14BDA | 20 | (b-75) | 10 | S-9 | 20 | — | — | 62200 | Polyamide |
| B-36 | IPC | 50 | CHDA | 20 | (b-89) | 20 | S-10 | 10 | — | — | 156000 | Polyamide |
| B-37 | TPC | 50 | IPDA | 30 | (b-99) | 10 | S-11 | 7 | H-4 | 3 | 90400 | Polyamide |
| B-38 | TPC | 50 | EDA | 30 | (b-12) | 10 | S-12 | 7 | H-4 | 3 | 42900 | Polyamide |

(Notes of Table)
14BDA: 1,4-Butanediamine
13PDA: 1,3-Propanediamine
EDA: Ethylenediamine
CHDA: 1,4-Cyclohexanediamine
IPDA: Isophorone diamine

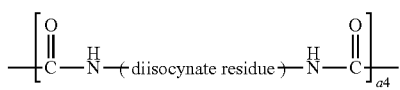

Formula (P-4)

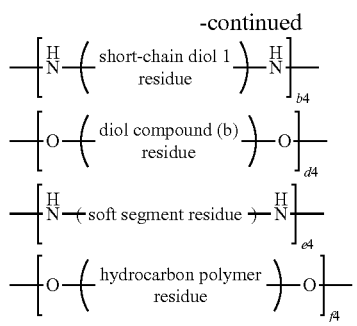

Synthesis Examples 6-2 to 6-11: Synthesis of Polyimide Polymers (B-50) to (B-57), (B-59), and (B-60)

Polyimide polymers (B-50) to (B-57), (B-59), and (B-60) were synthesized respectively in the same manner as in the method for synthesizing the polyimide polymer (B-58) except for the fact that, in the method for synthesizing the polyimide polymer (B-58), as the acid anhydride, the diamine compound, the diol compound, and/or the hydrocarbon polymer, compounds shown in Table 5 were used in proportions (molar ratios) shown in Table 5.

The obtained polyimide polymers are represented by Formula (P-5).

TABLE 4

| Polymer (B) | Diisocyanate | Hard segment | | | | Soft segment | | Hydrocarbon polymer segment | | Mw | Kind |
|---|---|---|---|---|---|---|---|---|---|---|---|
| | | a4 (mol %) | Short-chain diamine 4 | b4 (mol %) | Diol compound (b) | d4 (mol %) | Diamine | e4 (mol %) | Diol | f4 (mol %) | | |
| B-39 | MDI | 50 | — | — | (b-12) | 43 | S-7 | 7 | — | — | 37600 | Polyurea |
| B-40 | MDI | 50 | EDA | 30 | (b-25) | 20 | — | — | — | — | 25900 | Polyurea |
| B-41 | IPDI | 50 | 13PDA | 30 | (b-74) | 15 | — | — | H-1 | 5 | 85900 | Polyurea |
| B-42 | IPDI | 50 | 14BDA | 30 | (b-75) | 10 | S-7 | 10 | — | — | 63600 | Polyurea |
| B-43 | H12MDI | 50 | CHDA | 30 | (b-89) | 10 | S-8 | 10 | — | — | 93200 | Polyurea |
| B-44 | H12MDI | 50 | IPDA | 30 | (b-95) | 10 | S-9 | 5 | H-4 | 5 | 33400 | Polyurea |
| B-45 | H12MDI | 50 | 14BDA | 20 | (b-12) | 20 | S-10 | 5 | H-4 | 5 | 81800 | Polyurea |
| B-46 | H12MDI | 50 | 14BDA | 20 | (b-12) | 20 | S-11 | 5 | H-4 | 5 | 56500 | Polyurea |
| B-47 | H12MDI/HDI (50/50) | 50 | 14BDA | 20 | (b-12) | 20 | S-12 | 10 | — | — | 67200 | Polyurea |
| B-48 | H12MDI | 50 | 14BDA | 20 | (b-25) | 20 | S-17 | 5 | H-4 | 5 | 78900 | Polyurea |
| B-49 | H12MDI | 50 | 14BDA | 30 | (b-99) | 10 | S-12 | 10 | — | — | 67400 | Polyurea |

Regarding abbreviations in Table 4, Notes of Table 1 to Table 3 can be referred to.

[Synthesis of Polyimide Polymers]

Polyimide polymers that were used in the examples were synthesized respectively as described below. The obtained polyimide polymers are represented by Formula (P-5).

Synthesis Example 6-1: Synthesis of Polyimide Polymer (B-58)

4,4'-(2,2-Hexafluoroisopropylidene)diphthalic anhydride (6FDAA) (2.5 g) was injected into a 200 mL three-neck flask and dissolved in THF (50 mL). A THF solution (50 mL) obtained by dissolving 2,2-bis(4-aminophenyl)hexafluoropropane (6FPA) (0.54 g), the diol compound (b-12) synthesized above (0.76 g), and a hydrogenated polyisoprene diol (H-4, EPOL: trade name) (2.0 g) in THF was added thereto (the THF solution was added dropwise). The mixture was heated and stirred at 50° C. for two hours. The obtained polymer solution was added to methanol and precipitated. The obtained solid was separated into solid and liquid and dried in a vacuum oven at a temperature of 60° C. for 12 hours. A polyimide polymer (B-58) was obtained as described above.

In Formula (P-5), "residue" refers to a partial structure other than an acid anhydride group, a —OH group, and a —NH$_2$ group that are reactive groups at the terminal of the compound in the compounds used for the synthesis of the polyimide polymers (refer to Table 5). In addition, a5, b5, d5, e5, and f5 each represent the contents (mol %) of the respective constituent components in the polymers, and a5+b5+d5+e5+f5 is equal to 100 mol %.

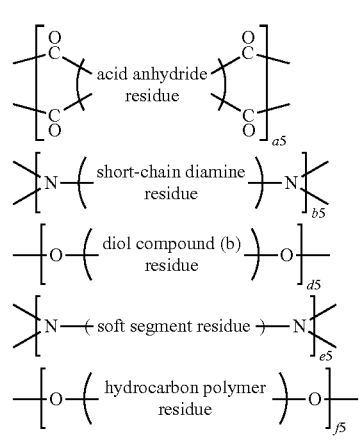

Formula (P-5)

TABLE 5

| Polymer (B) | Hard segment | | | | | | Soft segment | | Hydrocarbon polymer segment | | Mw | Kind |
|---|---|---|---|---|---|---|---|---|---|---|---|---|
| | Acid anhydride | a5 (mol %) | Short-chain diamine | b5 (mol %) | Diol compound (b) | d5 (mol %) | Diamine | e5 (mol %) | Diol | f5 (mol %) | | |
| B-50 | 6FDAA | 50 | 6FPA | 20 | (b-12) | 30 | — | — | — | — | 20500 | Polyimide |
| B-51 | 6FDAA | 50 | 6FPA | 20 | (b-25) | 25 | S-8 | 5 | — | — | 82900 | Polyimide |
| B-52 | THFDAA | 50 | DPEA | 20 | (b-74) | 20 | S-9 | 5 | H-1 | 5 | 95900 | Polyimide |
| B-53 | PDAA | 50 | CHDA | 20 | (b-75) | 20 | S-10 | 5 | H-2 | 5 | 54600 | Polyimide |
| B-54 | CHDAA | 50 | CHDA | 20 | (b-89) | 20 | S-11 | 5 | H-3 | 5 | 49800 | Polyimide |
| B-55 | 6FDAA | 50 | 6FPA | 20 | (b-95) | 25 | S-12 | 5 | — | — | 84700 | Polyimide |
| B-56 | 6FDAA | 50 | 6FPA | 20 | (b-12) | 25 | — | — | H-4 | 5 | 76300 | Polyimide |
| B-57 | 6FDAA | 50 | 6FPA | 20 | (b-12) | 25 | — | — | H-4 | 5 | 51100 | Polyimide |
| B-58 | 6FDAA | 50 | 6FPA | 20 | (b-12) | 25 | — | — | H-4 | 5 | 85500 | Polyimide |
| B-59 | 6FDAA | 50 | 6FPA | 20 | (b-25) | 25 | S-12 | 5 | — | — | 67900 | Polyimide |
| B-60 | 6FDAA | 50 | 6FPA | 20 | (b-99) | 20 | S-12 | 5 | H-4 | 5 | 67400 | Polyimide |

(Note of Table)
6FDAA: 4,4'-(2,2-Hexafluoroisopropylidene)diphthalic anhydride
THFDAA: 5-(2,5-Dioxotetrahydrofuryl)-3-methyl-3-cyclohexene-1,2-dicarboxylic anhydride
PDAA: Pyromellitic anhydride
CHDAA: 1,2,4,5-Cyclohexanetetracarboxylic dianhydride
6FPA: 2,2-Bis(4-aminophenyl)hexafluoropropane
DPEA: 4,4'-Diaminodiphenylether
Regarding abbreviations other than the above-described abbreviations, Notes of Table 1 to Table 4 can be referred to.

Example 1

Preparation Example of Solid Electrolyte Composition

One hundred eighty zirconia beads having a diameter of 5 mm were injected into a 45 mL zirconia container (manufactured by Fritsch Japan Co., Ltd.), and LPS synthesized above (4.85 g), a binder (B) shown in Table 6 (0.15 g) (the mass of the solid contents), and a dispersion medium shown in Table 6 (17.0 g) were injected thereinto. After that, the container was set in a planetary ball mill P-7 manufactured by Fritsch Japan Co., Ltd., and the components were mixed together at a temperature of 25° C. and a rotation speed of 300 rpm for two hours, thereby preparing each of solid electrolyte compositions Nos. S-1 to S-17 and CS-1 to CS-4.

Here, Nos. S-1 to S-17 are examples of the present invention, and Nos. CS-1 to CS-4 are comparative examples.

TABLE 6

| Solid electrolyte composition No. | Sulfide-based inorganic solid electrolyte | % | Binder (B) No. | Kind | % | Dispersion medium | Note |
|---|---|---|---|---|---|---|---|
| S-1 | LPS | 97 | B-1 | Polyurethane | 3 | Octane | Present Invention |
| S-2 | LPS | 97 | B-3 | Polyurethane | 3 | Octane | Present Invention |
| S-3 | LPS | 97 | B-13 | Polyurethane | 3 | Octane | Present Invention |
| S-4 | LPS | 97 | B-14 | Polyurethane | 3 | Octane | Present Invention |
| S-5 | LPS | 97 | B-19 | Polyurethane | 3 | Octane | Present Invention |
| S-6 | LPS | 97 | B-23 | Polyurethane | 3 | Octane | Present Invention |
| S-7 | LPS | 97 | B-24 | Polyurethane | 3 | Octane | Present Invention |
| S-8 | LPS | 97 | B-31 | Polyester | 3 | Toluene | Present Invention |
| S-9 | LPS | 97 | B-38 | Polyamide | 3 | Xylem | Present Invention |
| S-10 | LPS | 97 | B-47 | Polyurea | 3 | Cyclohexane | Present Invention |
| S-11 | LPS | 97 | B-48 | Polyurea | 3 | Octane | Present Invention |
| S-12 | LPS | 97 | B-49 | Polyurea | 3 | Octane | Present Invention |
| S-13 | LPS | 97 | B-58 | Polyimide | 3 | Octane | Present Invention |
| S-14 | LPS | 97 | B-59 | Polyimide | 3 | Octane | Present Invention |
| S-15 | LPS | 97 | B-60 | Polyimide | 3 | Octane | Present Invention |
| S-16 | LPS | 97 | B-19L | Polyurethane latex | 3 | Octane | Present Invention |
| S-17 | LPS | 97 | B-24L | Polyurethane latex | 3 | Octane | Present Invention |
| CS-1 | LPS | 97 | BC-1 | Fluorine-based polymer | 3 | Octane | Comparative Example |
| CS-2 | LPS | 97 | BC-2 | Hydrocarbon polymer | 3 | Octane | Comparative Example |
| CS-3 | LPS | 97 | BC-3 | Acrylic polymer | 3 | Octane | Comparative Example |
| CS-4 | LPS | 97 | BC-4 | Urethane-based polymer | 3 | Octane | Comparative Example |

(Notes of Table)

"%" in the table indicates "% by mass" in solid contents.

LPS: Li—P—S-Based glass synthesized above

The number of the binder (B) indicates the number of each polymer synthesized above.

BC-1: Fluorine-based polymer: PVdF-HFP (KYNAR FLEX 2800-20: trade name, manufactured by Arkema K.K.)

BC-2: Hydrocarbon polymer: SBR (styrene butadiene rubber, product code: 182907, manufactured by Aldrich-Sigma, Co. LLC.)

BC-3: Acrylic polymer (methyl polymethacrylate-polymethacrylic acid copolymer (50/50 mol %), product code: 376914, manufactured by Aldrich-Sigma, Co. LLC.)

BC-4: Urethane-based polymer (addition polymer of diphenylmethane diisocyanate (50 mol %), 1,4-butanediol (30 mol %), and 2,2-dimethylolbutanoic acid (20 mol %), synthesized using the same method as in Synthesis Example 2-1; mass-average molecular weight was 43,000)

<Production of Sheets for all-Solid State Secondary Battery (Solid Electrolyte-Containing Sheet for all-Solid State Secondary Battery)>

Each of the solid electrolyte compositions obtained above was applied onto a 20 μm-thick aluminum foil (collector) using an applicator (trade name: SA-201 Baker-type applicator, manufactured by Tester Sangyo Co., Ltd.) and heated at 80° C. for two hours, thereby drying the solid electrolyte composition. After that, the dried solid electrolyte composition was heated at a temperature of 120° C. and a pressure of 600 MPa using a heat pressing machine so as to obtain a predetermined density, thereby obtaining sheets for an all-solid state secondary battery Nos. 101 to 117 and c11 to c14. The film thickness of the solid electrolyte layer was 50 μm.

<Testing>

On the solid electrolyte-containing sheets produced above, the following tests were carried out. Hereinafter, testing methods will be described, and the results are summarized in Table 7.

Testing Example 1: Evaluation of Scratch Resistance

A 10 cm×20 cm rectangular specimen was cut out from the sheet for an all-solid state secondary battery. The surface portion of the cut-out sheet was reciprocally rubbed five centimeters (one-way distance) a total of 20 times using a continuous loading scratching intensity tester "TYPE: 18/18L" (manufactured by Shinto Scientific Co., Ltd.) by applying a load of 1.0 g to a 10 mmϕ aluminum foil. The rubbed surface of the sheet was observed using an optical microscope for inspection "ECLIPSE Ci" (trade name, manufactured by Nikon Corporation), and the presence or absence of chips, breakage, or cracks of the solid electrolyte layer and the presence or absence of the peeling of the solid electrolyte layer from the aluminum foil were evaluated according to the following standards. In the present testing, evaluation standards "C" or higher are pass.

—Evaluation Standards—

A: Defects (chips, breakage, cracks; and peeling) were never observed.

B: The area of a defect portion was more than 0% and 10% or less of the total area of the observation subject.

C: The area of a defect portion was more than 10% and 30% or less of the total area of the observation subject.

D: The area of a defect portion was more than 30% and 90% or less of the total area of the observation subject.

E: The area of a defect portion was more than 90% of the total area of the observation subject.

The area of the defect portion refers to an area (projected area) converted to the surface area of the solid electrolyte layer.

Testing Example 2: Evaluation of Bend Resistance

A 10 cm×20 cm rectangular specimen was cut out from the sheet for an all-solid state secondary battery. The cut-out sheet was bent using a cylindrical mandrel tester "Product code: 056" (mandrel diameter: 10 mm, manufactured by Allgood Co., Ltd.) according to Japanese Industrial Standards (JIS) K5600-5-1 (bend resistance (cylindrical mandrel: testing using a type 1 testing device)) and International Organization for Standardization (ISO) 1519. The presence or absence of defects was confirmed in the same manner as in the evaluation of the scratch resistance and evaluated according to the following standards. In the present testing, evaluation standards "C" or higher are pass.

—Evaluation Standards—

A: Defects (chips, breakage, cracks, and peeling) were never observed.

B: The area of a defect portion was more than 0% and 10% or less of the total area of the observation subject.

C: The area of a defect portion was more than 10% and 30% or less of the total area of the observation subject.

D: The area of a defect portion was more than 30% and 90% or less of the total area of the observation subject.

E: The area of a defect portion was more than 90% of the total area of the observation subject.

Testing Example 3: Evaluation of Ion Conductivity

Figure 2:
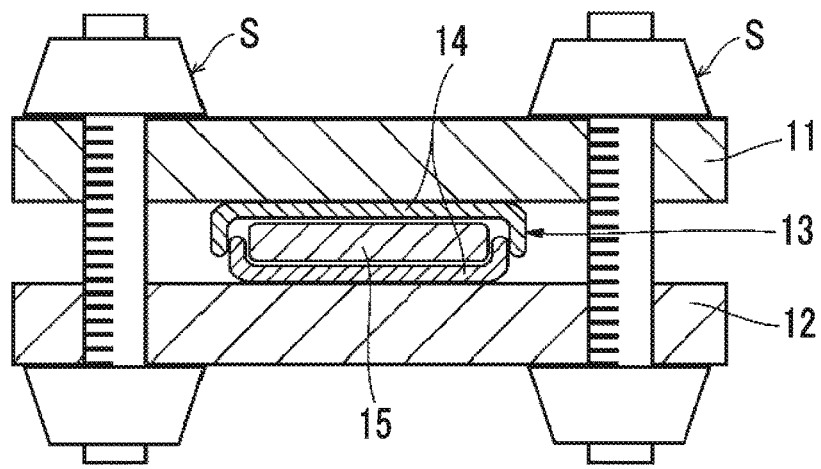
FIG. 2 is a vertical cross-sectional view schematically illustrating a test body for ion conductivity measurement produced in examples.
Figure 3:
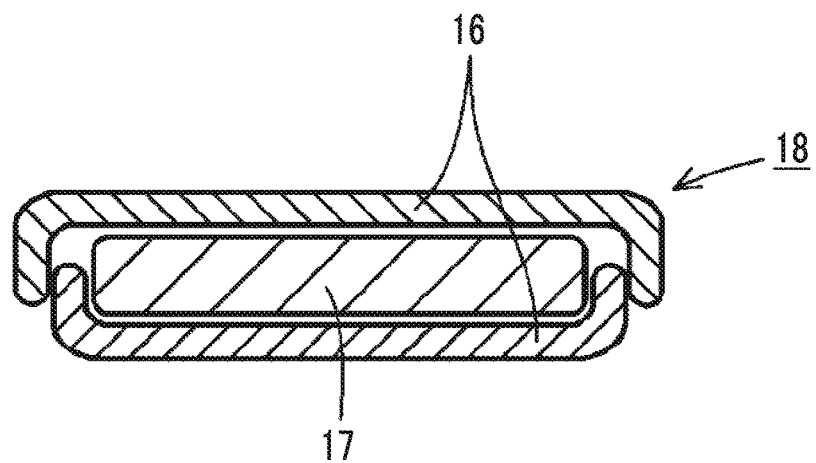
FIG. 3 is a vertical cross-sectional view schematically illustrating an all-solid state secondary battery (coin battery) produced in examples.

Two disc-shaped pieces having a diameter of 14.5 mm was cut out from the solid electrolyte-containing sheet obtained above, the coated surfaces (the surfaces of the solid electrolyte layers) were attached together (indicated by a reference 15 in FIG. 2 and a reference 17 in FIG. 3), a spacer and a washer (both not illustrated) were combined together as illustrated in FIG. 3, and the disc-shaped pieces were put into a 2032-type stainless steel coin case 16 (reference 14 in FIG. 2) (a coin-type all-solid state secondary battery 18 was produced). As illustrated in FIG. 2, the all-solid state secondary battery 13 (18 in FIG. 3) was interposed between a lower supporting plate 12 and an uppering support plate 11, screws S were swaged with a force of eight newtons (N) using a torque wrench, thereby producing each of test bodies for ion conductivity measurement 101 to 117 and c11 to c14.

The ion conductivity was measured using each of the test bodies for ion conductivity measurement obtained above. Specifically, the alternating current impedance was measured at a voltage magnitude of 5 mV and frequencies of 1 MHz to 1 Hz using 1255B FREQUENCY RESPONSE ANALYZER (trade name, manufactured by Solartron Analytical) in a constant-temperature tank (30° C.). Therefore, the resistance of the attached solid electrolyte-containing sheets (specimens) in the film thickness direction was obtained and computed using Expression (I) below, thereby obtaining the ion conductivity.

Ion conductivity (mS/cm)=1,000×film thickness of specimen (cm)/(resistance (Ω)×area of specimen (cm$^2$))     Expression (I)

TABLE 7

| Test body No. | Solid electrolyte composition | Scratch resistance | Bend resistance | Ion conductivity (mS/cm) | Note |
|---|---|---|---|---|---|
| 101 | S-1 | B | B | 0.33 | Present Invention |
| 102 | S-2 | A | A | 0.36 | Present Invention |
| 103 | S-3 | A | A | 0.21 | Present Invention |
| 104 | S-4 | A | B | 0.43 | Present Invention |
| 105 | S-5 | A | A | 0.44 | Present Invention |
| 106 | S-6 | A | A | 0.42 | Present Invention |
| 107 | S-7 | A | A | 0.33 | Present Invention |
| 108 | S-8 | B | B | 0.37 | Present Invention |
| 109 | S-9 | B | A | 0.46 | Present Invention |
| 110 | S-10 | B | A | 0.42 | Present Invention |
| 111 | S-11 | A | A | 0.27 | Present Invention |
| 112 | S-12 | A | B | 0.24 | Present Invention |
| 113 | S-13 | C | B | 0.38 | Present Invention |
| 114 | S-14 | B | A | 0.34 | Present Invention |
| 115 | S-15 | B | B | 0.24 | Present Invention |
| 116 | S-16 | A | A | 0.65 | Present Invention |
| 117 | S-17 | A | A | 0.63 | Present Invention |
| c11 | CS-1 | E | E | 0.48 | Comparative Example |
| c12 | CS-2 | E | D | 0.092 | Comparative Example |
| c13 | CS-3 | D | D | 0.21 | Comparative Example |
| c14 | CS-4 | C | D | 0.37 | Comparative Example |

As is clear from Table 7, the solid electrolyte-containing sheets of Nos. c11 to c14 produced using the solid electrolyte compositions containing the binder not having at least one selected from the constituent component represented by Formula (1) or the constituent component represented by Formula (2) are not a solid electrolyte-containing sheet having all of scratch resistance, bend resistance, and an ion conductivity on a high level in a balanced manner.

In contrast, it is found that the solid electrolyte-containing sheets of Nos. 101 to 117 produced using the solid electrolyte composition of the embodiment of the present invention containing the binder (B) having at least one selected from the constituent component represented by Formula (1) or the constituent component represented by Formula (2) all have scratch resistance, bend resistance, and an ion conductivity on a high level in a balanced manner.

Example 2

In Example 2, electrode sheets for an all-solid state secondary battery were produced, and performance thereof was evaluated.

<Preparation of Compositions for Electrode>

One hundred eighty zirconia beads having a diameter of 5 mm were injected into a 45 mL zirconia container (manufactured by Fritsch Japan Co., Ltd.), and LPS synthesized in Example 1 (2.0 g), a binder (B) (0.1 g), and octane (22 g) as a dispersion medium were injected thereinto. After that, the container was set in a planetary ball mill P-7 manufactured by Fritsch Japan Co., Ltd., and the components were stirred at a temperature of 25° C. and a rotation speed of 300 rpm for two hours. After that, an electrode active material (7.9 g) shown in Table 8 was injected into the container, again, the container was set in the planetary ball mill P-7, and the components were continuously mixed together at a temperature of 25° C. and a rotation speed of 100 rpm for 15 minutes. A composition for an electrode P-1 was obtained as described above.

Compositions for an electrode P-2 to P-17 and CP-1 to CP-4 were prepared respectively in the same manner as in the preparation of the composition for an electrode P-1 except for the fact that, in the preparation of the composition for an electrode P-1, the electrode active material, the binder (B), and/or the dispersion medium and amounts used were changed as shown in Table 8.

<Production of Electrode Sheets for all-Solid State Secondary Battery>

Each of the compositions for an electrode obtained above was applied onto a 20 μm-thick stainless steel foil (collector) using the Baker-type applicator and heated at 80° C. for two hours, thereby drying the composition for an electrode. After that, the dried composition for an electrode was heated (at 120° C.) and pressurized (at 600 MPa for one minute) using a heat pressing machine so as to obtain a predetermined density. Electrode sheets for an all-solid state secondary battery having an electrode active material layer Nos. P-1 to P-17 and CP-1 to CP-4 were produced. The film thickness of the electrode active material layer was 100 μm.

<Testing>

On the electrode sheets for an all-solid state secondary battery produced above, the (evaluation of scratch resistance: Testing Example 1) and the (evaluation of bend resistance: Testing Example 2) were carried out in the same manner as for the solid electrolyte-containing sheets. In addition, the (evaluation of ion conductivity: Testing Example 3) was carried out using coin batteries produced using the obtained respective electrode sheets for an all-solid state secondary battery. The results are summarized in Table 8.

TABLE 8

| Electrode sheet No. | Electrode active material | Sulfide-based inorganic solid electrolyte % | | Binder (B) | | | Dispersion medium | Scratch resistance | Bend resistance | Ion conductivity (mS/cm) | Note |
|---|---|---|---|---|---|---|---|---|---|---|---|
| | | % | | No. | Kind | % | | | | | |
| P-1 | NCA | 79 | LPS | 20 | B-1 | Polyurethane | 1 | Octane | B | B | 0.055 | Present Invention |
| P-2 | NCA | 79 | LPS | 20 | B-3 | Polyurethane | 1 | Octane | A | A | 0.043 | Present Invention |
| P-3 | NCA | 79 | LPS | 20 | B-13 | Polyurethane | 1 | Octane | A | A | 0.078 | Present Invention |
| P-4 | NMC | 79 | LPS | 20 | B-14 | Polyurethane | 1 | Octane | A | B | 0.056 | Present Invention |
| P-5 | NMC | 79 | LPS | 20 | B-19 | Polyurethane | 1 | Octane | A | A | 0.065 | Present Invention |
| P-6 | Graphite | 59 | LPS | 40 | B-23 | Polyurethane | 1 | Octane | A | A | 0.12 | Present Invention |
| P-7 | Graphite | 59 | LPS | 40 | B-24 | Polyurethane | 1 | Octane | A | A | 0.15 | Present Invention |
| P-8 | NMC | 79 | LPS | 20 | B-31 | Polyester | 1 | Toluene | B | C | 0.068 | Present Invention |
| P-9 | NMC | 79 | LPS | 20 | B-38 | Polyamide | 1 | Xylene | B | A | 0.072 | Present Invention |
| P-10 | NMC | 79 | LPS | 20 | B-47 | Polyurea | 1 | Cyclohexane | B | A | 0.054 | Present Invention |
| P-11 | Graphite | 59 | LPS | 40 | B-48 | Polyurea | 1 | Octane | A | A | 0.16 | Present Invention |
| P-12 | Graphite | 59 | LPS | 40 | B-49 | Polyurea | 1 | Octane | A | B | 0.11 | Present Invention |
| P-13 | NMC | 79 | LPS | 20 | B-58 | Polyimide | 1 | Octane | C | B | 0.074 | Present Invention |
| P-14 | Graphite | 59 | LPS | 40 | B-59 | Polyimide | 1 | Octane | B | C | 0.13 | Present Invention |
| P-15 | Graphite | 59 | LPS | 40 | B-60 | Polyimide | 1 | Octane | B | A | 0.11 | Present Invention |
| P-16 | NMC | 79 | LPS | 20 | B-19L | Polyurethane latex | 1 | Octane | A | A | 0.097 | Present Invention |
| P-17 | Graphite | 59 | LPS | 40 | B-24L | Polyurethane latex | 1 | Octane | A | A | 0.23 | Present Invention |
| CP-1 | NMC | 79 | LPS | 20 | BC-1 | Fluorine-based polymer | 1 | Octane | E | E | 0.066 | Comparative Example |
| CP-2 | Graphite | 59 | LPS | 40 | BC-1 | Fluorine-based polymer | 1 | Octane | E | E | 0.089 | Comparative Example |
| CP-3 | NMC | 79 | LPS | 20 | BC-2 | Hydrocarbon polymer | 1 | Octane | E | D | 0.054 | Comparative Example |
| CP-4 | NMC | 79 | LPS | 20 | BC-3 | Acrylic polymer | 1 | Octane | C | D | 0.068 | Comparative Example |

(Notes of Table)
LPS: Li—P—S-Based glass synthesized above
The number of the binder (B) indicates the number of each polymer synthesized above.
NCA: $LiNi_{0.85}Co_{0.10}Al_{0.05}O_2$ (lithium nickel cobalt aluminum oxide)
NMC: $LiNi_{1/3}Co_{1/3}Mn_{1/3}O_2$ (lithium nickel manganese cobalt oxide)

As is clear from Table 8, the electrode sheets for an all-solid state secondary battery of Nos. CP-1 to CP-4 produced using the compositions for an electrode containing the binder (B) not having at least one selected from the constituent component represented by Formula (1) or the constituent component represented by Formula (2) are not an electrode sheet having all of scratch resistance, bend resistance, and an ion conductivity on a high level in a balanced manner.

In contrast, it is found that the electrode sheets for an all-solid state secondary battery of Nos. P-1 to P-17 produced using the composition for an electrode of the embodiment of the present invention containing the binder (B) having at least one selected from the constituent component represented by Formula (1) or the constituent component represented by Formula (2) all have scratch resistance, bend resistance, and an ion conductivity on a high level in a balanced manner even in a case in which the content of the binder (B) is as low as 1% by mass.

From the results of Example 1 and Example 2, it is found that the solid electrolyte-containing sheet or the electrode sheet for an all-solid state secondary battery produced using the solid electrolyte composition of the embodiment of the present invention are capable of imparting a high ion conductivity and, furthermore, an excellent characteristic enabling the suppression of the occurrence of short-circuit to an all-solid state secondary battery in the case of being used in the all-solid state secondary battery. In addition, in the case of using the solid electrolyte-containing sheet or the electrode sheet for an all-solid state secondary battery to produce all-solid state secondary batteries, the production aptitude of all-solid state secondary batteries is excellent, and it is also possible to improve the yield.

The present invention has been described together with the embodiment; however, unless particularly specified, the present inventors do not intend to limit the present invention to any detailed portion of the description and consider that the present invention is supposed to be broadly interpreted within the concept and scope of the present invention described in the claims.

The present application claims priority on the basis of JP2017-024481 filed on Feb. 13, 2017 in Japan, the content of which is incorporated herein by reference.

EXPLANATION OF REFERENCES

1: negative electrode collector
2: negative electrode active material layer
3: solid electrolyte layer
4: positive electrode active material layer
5: positive electrode collector
6: operation portion 10: all-solid state secondary battery
11: upper portion-supporting plate
12: lower portion-supporting plate
13, 18: all-solid state secondary battery
14, 16: 2032-type coin case
15, 17: solid electrolyte-containing sheet or electrode sheet for all-solid state secondary battery
S: screw

What is claimed is:

1. A solid electrolyte composition comprising:
an inorganic solid electrolyte (A) having a conductivity of an ion of a metal belonging to Group I or II of the periodic table; and
a binder (B),
wherein the binder (B) has a constituent component represented by Formula (1),

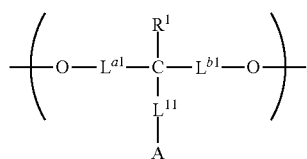  (1)

in Formula (1), $R^1$ represents a hydrogen atom, an alkyl group, or an aryl group, $L^{a1}$ and $L^{b1}$ each independently represent a single bond or an alkylene group, $L^{11}$ represents a divalent organic group, and A represents a group selected from a group of functional groups below,
<group of functional groups>
a carboxylic acid group, a sulfonic acid group, a phosphoric acid group, a cyano group, and a hydrocarbon ring group in which three or more rings are fused.

2. The solid electrolyte composition according to claim 1, wherein one of $L^{a1}$ and $L^{b1}$ is a single bond, a methylene group, or an ethylene group, and the other of $L^{a1}$ and $L^{b1}$ is a methylene group or an ethylene group.

3. The solid electrolyte composition according to claim 1, wherein a partial structure $-L^{11}$-A in Formula (1) is represented by any of Formulae (3) to (7),

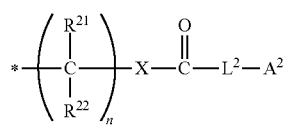  (3)

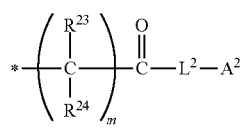  (4)

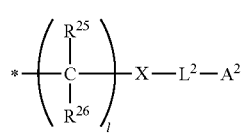  (5)

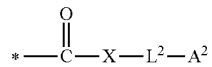  (6)

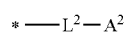  (7)

in Formulae (3) to (7), $R^{21}$ to $R^{26}$ each independently represent a hydrogen atom, an alkyl group, or an aryl group, $L^2$ represents an alkylene group having 1 to 18 carbon atoms, an alkenylene group having 2 to 20 carbon atoms or an arylene group having 6 to 16 carbon atoms, or a combination thereof, $A^2$ represents a carboxylic acid group, n, m, and l each independently represent an integer of 0 to 2, X represents —O—, —S—, or —N($R^2$)—, and $R^2$ represents a hydrogen atom, an alkyl group, or an aryl group, and * represents a bonding portion with a C atom in Formula (1).

4. The solid electrolyte composition according to claim 1, wherein the binder (B) has a hard segment having at least one bond selected from a urethane bond, a urea bond, an amide bond, and an imide bond and a soft segment which has a number-average molecular weight of 300 or more and has at least one chain selected from a polyalkylene ether chain, a polyester chain, a polycarbonate chain, and a silicone chain.

5. The solid electrolyte composition according to claim 1, wherein the binder (B) has a hydrocarbon polymer segment.

6. The solid electrolyte composition according to claim 1, wherein the binder (B) is a particulate polymer having an average particle diameter of 10 to 1,000 nm.

7. The solid electrolyte composition according to claim 1, further comprising:
a dispersion medium (C).

8. The solid electrolyte composition according to claim 1, further comprising:
an active material (D).

9. The solid electrolyte composition according to claim 1, further comprising:
a conductive auxiliary agent (E).

10. The solid electrolyte composition according to claim 1,
wherein the inorganic solid electrolyte (A) is a sulfide-based inorganic solid electrolyte.

11. A solid electrolyte-containing sheet comprising:
an inorganic solid electrolyte (A) having a conductivity of an ion of a metal belonging to Group I or II of the periodic table; and
a binder (B),
wherein the binder (B) has a constituent component represented by Formula (1),

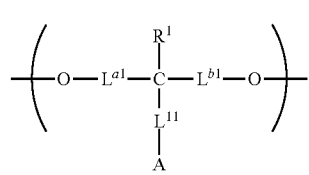  (1)

in Formula (1), $R^1$ represents a hydrogen atom, an alkyl group, or an aryl group, $L^{a1}$ and $L^{b1}$ each independently represent a single bond or an alkylene group, $L^{11}$ represents a divalent organic group, and A represents a group selected from a group of functional groups below, <group of functional groups> a carboxylic acid group, a sulfonic acid group, a phosphoric acid group, a cyano group, and a hydrocarbon ring group in which three or more rings are fused.

12. A method for manufacturing the solid electrolyte-containing sheet according to claim 11, the method comprising:
   a step of applying a solid electrolyte composition containing the inorganic solid electrolyte (A), the binder (B), and a dispersion medium (C) onto a base material; and
   a step of drying the applied solid electrolyte composition.

13. An all-solid state secondary battery comprising:
   a positive electrode active material layer;
   a negative electrode active material layer; and
   a solid electrolyte layer,
   wherein at least one of the positive electrode active material layer, the negative electrode active material layer, and the solid electrolyte layer contains an inorganic solid electrolyte (A) having a conductivity of an ion of a metal belonging to Group I or II of the periodic table; and a binder (B), and the binder (B) has a constituent component represented by Formula (1),

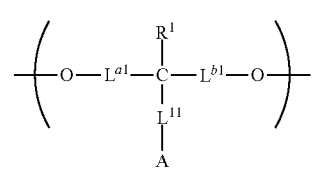

in Formula (1), $R^1$ represents a hydrogen atom, an alkyl group, or an aryl group, $L^{a1}$ and $L^{b1}$ each independently represent a single bond or an alkylene group, $L^{11}$ represents a divalent organic group, and A represents a group selected from a group of functional groups below, <group of functional groups> a carboxylic acid group, a sulfonic acid group, a phosphoric acid group, a cyano group, and a hydrocarbon ring group in which three or more rings are fused.

14. A method for manufacturing an all-solid state secondary battery, the method comprising preparing at least one of a positive electrode active material layer, a negative electrode active material layer, and a solid electrolyte layer by using the solid electrolyte-containing sheet obtained by the method according to claim 12.

* * * * *